US010415067B2

(12) United States Patent
Marliere

(10) Patent No.: US 10,415,067 B2
(45) Date of Patent: Sep. 17, 2019

(54) METHOD FOR THE ENZYMATIC PRODUCTION OF D-ERYTHROSE AND ACETYL PHOSPHATE

(71) Applicant: SCIENTIST OF FORTUNE S.A., Luxembourg (LU)

(72) Inventor: Philippe Marliere, Tournai (BE)

(73) Assignee: Scientist of Fortune, S.A., Luxembourg (LU)

( * ) Notice: Subject to any disclaimer, the term of this patent is extended or adjusted under 35 U.S.C. 154(b) by 140 days.

(21) Appl. No.: 15/313,416

(22) PCT Filed: May 22, 2015

(86) PCT No.: PCT/EP2015/061391
§ 371 (c)(1),
(2) Date: Nov. 22, 2016

(87) PCT Pub. No.: WO2015/181074
PCT Pub. Date: Dec. 3, 2015

(65) Prior Publication Data
US 2017/0191095 A1    Jul. 6, 2017

(30) Foreign Application Priority Data
May 26, 2014  (EP) .................... 14169813

(51) Int. Cl.
*C12P 7/66*  (2006.01)
*C12P 9/00*  (2006.01)
*C12P 19/02*  (2006.01)
*C12P 7/26*  (2006.01)
*C12N 9/10*  (2006.01)
*C12N 9/88*  (2006.01)
*C12N 9/92*  (2006.01)
*C12P 7/24*  (2006.01)
*C12P 19/40*  (2006.01)

(52) U.S. Cl.
CPC .............. *C12P 9/00* (2013.01); *C12N 9/1025* (2013.01); *C12N 9/88* (2013.01); *C12N 9/92* (2013.01); *C12P 7/24* (2013.01); *C12P 7/26* (2013.01); *C12P 19/02* (2013.01); *C12P 19/40* (2013.01); *C12Y 203/01008* (2013.01); *C12Y 203/03015* (2013.01); *C12Y 401/02004* (2013.01); *C12Y 401/02009* (2013.01); *C12Y 503/01005* (2013.01)

(58) Field of Classification Search
CPC ....................................................... C12P 7/66
See application file for complete search history.

(56) References Cited

U.S. PATENT DOCUMENTS

2017/0191095 A1* 7/2017 Marliere ................ C12P 19/02

OTHER PUBLICATIONS

Posthuma et al., Applied and Environmental Microbiology, Feb. 2002, p. 831-837.*
Full examination report for standard patent application dated May 31, 2018.
Wei et al., "Fructose Uptake in Bifidobacterium Longum NCC2705 is Mediated by an ATP-binding Cassette Transporter", The Journal of Biological Chemistry vol. 287, No. 1, pp. 357-367, (2012).
Extended European Search Report from corresponding EP 14169813.4, dated Aug. 19, 2014.
International Search Report and Written Opinion from corresponding PCT/EP2015/061391, dated Aug. 28, 2015.
Bogorad et al., "Synthetic non-oxidative glycolysis enables complete carbon conservation", XP-002743423, Oct. 31, 2013, vol. 502, Nature, pp. 693-698.
Breslow et al., "Transketolase reaction under credible prebiotic conditions", Department of Chemistry, Columbia University, New York, NY, XP-002728183, PNAS, Mar. 12, 2013, vol. 110, No. 11, pp. 4184-4187.
Caescuet al., "Bifidobacterium longum Requires a Fructokinase (Frk: ATP:D-Fructose 6-Phosphotransferase, EC 2.7.1.4) for Fructose Catabolism", XP-002422619, Journal of Bacteriology, Oct. 2004, pp. 6515-6525.
Servinsky et al., "Arabinose is metabolized via a phosphoketolase pathway in Clostridium acetobutylicum ATCC 824", J Ind Microbiol Biotechnol, 2012, vol. 39, pp. 1859-1867.
International Preliminary Report on Patentability and Written Opinion dated Dec. 8, 2016 received in PCT/EP2015/061391.

* cited by examiner

*Primary Examiner* — Tekchand Saidha
(74) *Attorney, Agent, or Firm* — Michele M. Wales; Inhouse Patent Counsel, LLC

(57) ABSTRACT

Described is a method for the production of D-erythrose and acetyl phosphate comprising the enzymatic conversion of D-fructose into D-erythrose and acetyl phosphate by making use of a phosphoketolase. The produced D-erythrose can further be converted into glycolaldehyde by a method for the production of glycolaldehyde comprising the enzymatic conversion of D-erythrose into glycolaldehyde by making use of an aldolase, wherein aldolase is a 2-deoxyribose-5-phosphate aldolase (EC 4.1.2.4) or a fructose-bisphosphate aldolase (EC 4.1.2.13). The produced glycolaldehyde can finally be converted into acetyl phosphate by the enzymatic conversion of the thus produced glycolaldehyde into acetyl phosphate by making use of a phosphoketolase or a sulfoacetaldehyde acetyltransferase.

Figure 1:
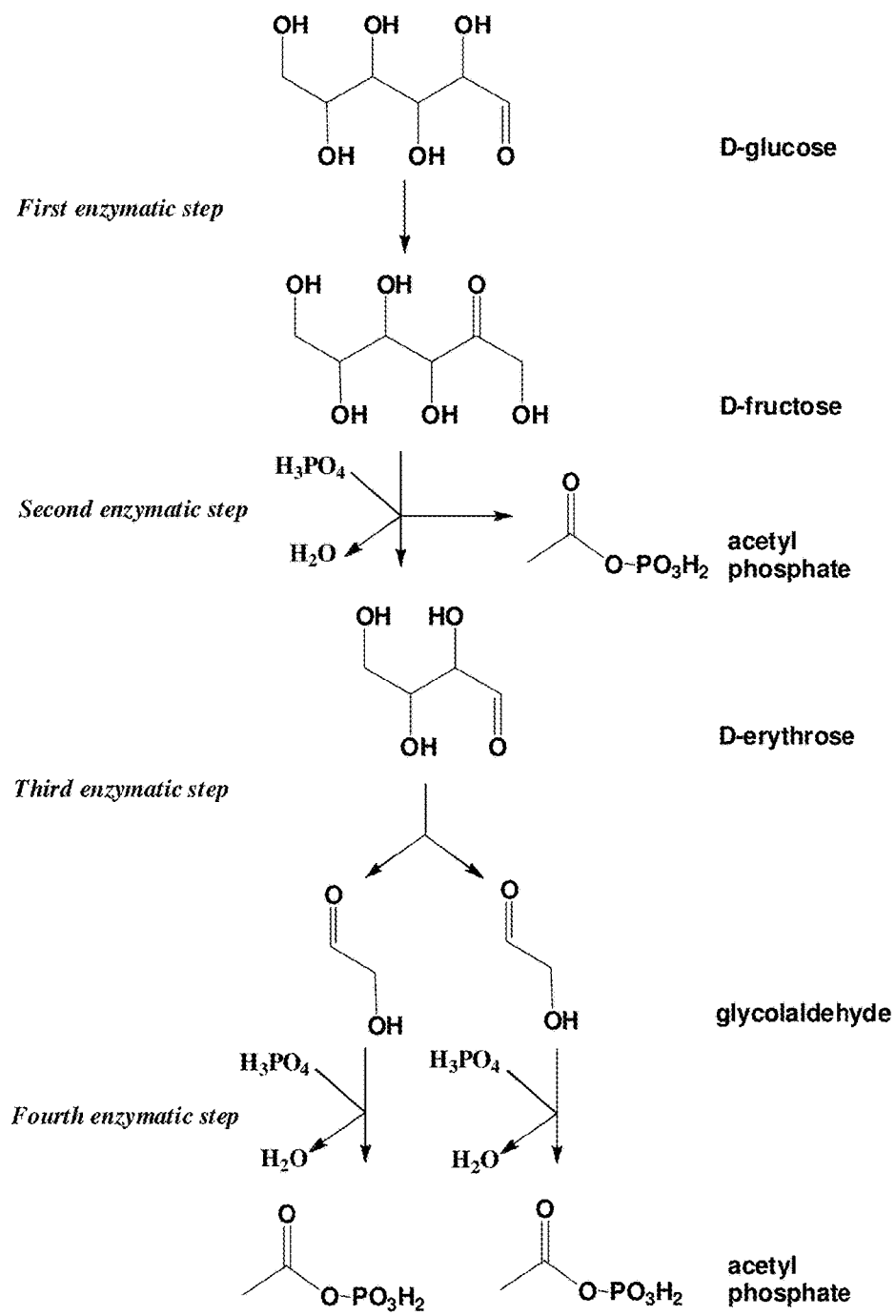

28 Claims, 6 Drawing Sheets
Specification includes a Sequence Listing.

| Assay | 2-deoxyribose-5-phosphate aldolase | Uniprot Accession Number |
|---|---|---|
| A | Acetobacter sp | R5Q5K8 |
| B | Thermus thermophilus | Q5SJ28 |
| C | Lactobacillus acidophilus | Q5FLZ2 |
| D | Clostridium acetobutylicium | Q97IU5 |
| E | Staphylococcus aureus | Q2YUU4 |
| F | Bacteroides fragilis | K1GTP0 |
| G | Hyperthermus butylicus | A2BLE9 |
| H | Acetobacterium woodii | H6LFY1 |
| I | Streptococcus gordonii | A8AX59 |
| J | Shewanella oneidensis | Q8EHK4 |
| K | Aspergillus fumigatus | A4D9G0 |

Figure 6

METHOD FOR THE ENZYMATIC PRODUCTION OF D-ERYTHROSE AND ACETYL PHOSPHATE

The present invention relates to a method for the production of D-erythrose and acetyl phosphate comprising the enzymatic conversion of D-fructose into D-erythrose and acetyl phosphate by making use of a phosphoketolase. The produced D-erythrose can further be converted into glycolaldehyde by a method for the production of glycolaldehyde comprising the enzymatic conversion of D-erythrose into glycolaldehyde by making use of an aldolase, wherein said aldolase is a 2-deoxyribose-5-phosphate aldolase (EC 4.1.2.4) or a fructose-bisphosphate aldolase (EC 4.1.2.13). The produced glycolaldehyde can finally be converted into acetyl phosphate by the enzymatic conversion of the thus produced glycolaldehyde into acetyl phosphate by making use of a phosphoketolase or a sulfoacetaldehyde acetyltransferase.

For the past several decades, practitioners of metabolic engineering have endeavoured to explore biological solutions for the production of chemicals, thus, providing alternatives to more traditional chemical processes. In general, biological solutions allow for the utilization of renewable feedstocks (e.g. sugars) and compete with existing petrochemical based processes. A multi-step, biological solution for the production of a chemical typically comprises a microorganism as the catalyst for the conversion of feedstock to a target molecule. A complete set of enzyme reactions for the production of a particular target molecule can be grouped into those belonging to central carbon pathways and those belonging to the product specific pathway. The reactions belonging to central carbon and product specific pathways are linked in that redox (typically, NAD (P)H) and energetic (typically, ATP) constraints of every enzyme reaction must be accounted for in an overall balance contributing to the competitiveness of the process. Historically, central carbon pathways of heterotrophs growing on sugars have been described as the Embden-Meyerhoff-Parnas pathway (EMPP; i.e., "glycolysis"), the pentose phosphate pathway (PPP), the Entner-Doudoroff pathway (EDP), and the phosphoketolase pathway (PKP) (see Gottschalk (1986), Bacterial Metabolism, $2^{nd}$ Edition, Springer-Verlag, New York). Each central pathway or combinations of central pathways offer advantages and disadvantages with respect to a specific target molecule. In order to provide competitive bioprocesses, recombinant microorganisms with modifications involving the EMPP, PPP and EDP have been described (M. Emmerling et al., Metab. Eng. 1:117 (1999); L. O. Ingram et al., Appl. Environ. Microbiol. 53: 2420 (1987); C. T. Trinh et al., Appl. Environ. Microbiol. 74:3634 (2008)). More recently, recombinant microorganisms with modifications involving the PKP have been described (see Sonderegger et al. Appl. Environ. Microbiol. 70 (2004), 2892-2897, U.S. Pat. No. 7,253,001, Chinen et al. J. Biosci. Bioeng. 103 (2007), 262-269, U.S. Pat. No. 7,785,858; Fleige et al., Appl. Microbiol. Cell Physiol. 91 (2011), 769-776).

The EMPP (glycolysis) converts 1 mol glucose to 2 mol pyruvate (PYR). When acetyl-CoA is desired, 1 mol PYR can be converted to 1 mol of acetyl-CoA (AcCoA) with the concomitant generation of 1 mol $CO_2$ and 1 mol NADH. The sum of the reactions is given in Equation 1.

glucose+2ADP+2$H_3PO_4$+2CoA+4$NAD^+$→2acetyl-CoA+2$CO_2$+2ATP+2$H_2O$+4NADH+4$H^+$   (Equation 1)

The PPP provides a means to convert 1 mol glucose to 1 mol $CO_2$ and 2 mol NADPH, with the concomitant generation of 0.67 mol fructose-6-phosphate (F6P) and 0.33 mol glyceraldehyde-3-phosphate (GAP). The F6P and GAP thus formed must be metabolized by other reaction pathways, e.g. by the EMPP. The EDP converts 1 mol glucose to 1 mol GAP and 1 mol PYR with the concomitant generation of 1 mol NADPH. As with the PPP, the GAP thus formed must be metabolized by other reaction pathways. The PKP provides a means to convert 1 mol glucose to 1 mol GAP and 1.5 mol acetyl phosphate (AcP). When acetyl-CoA is desired, 1 equivalent of AcP plus 1 equivalent coenzyme A (CoA) can be converted to 1 equivalent acetyl-CoA and 1 equivalent inorganic phosphate (Pi) by the action of phosphotransacetylase.

For specific target molecules derived from AcCoA moieties generated through the PKP and near redox neutrality to the AcCoA moieties, there exists a deficiency in the overall energy balance. The PKP (and, similarly, the PPP and EDP) does not generate ATP for the conversion of glucose to glucose-6-phosphate. In the case of phosphoenolpyruvate (PEP)-dependent glucose uptake, PEP must be generated by other means, e.g. through the EMPP. Recycling GAP through the PKP exacerbates the issue, particularly when the product specific pathway provides little ATP.

Sonderegger (loc. cit.) and U.S. Pat. No. 7,253,001 disclose recombinant Saccharomyces cerevisiae strains comprising native or overexpressed phosphoketolase activity together with overexpressed phosphotransacetylase to increase the yield in the conversion of glucose/xylose mixtures to ethanol. These strains feature PEP-independent glucose uptake with both the EMPP and the PPP operative.

Chinen (loc. cit.) and U.S. Pat. No. 7,785,858 disclose a recombinant bacterium selected from the group consisting of the Enterobacteriaceae family, Coryneform bacterium, and Bacillus bacterium comprising increased phosphoketolase activity for the conversion of glucose to target molecules which are produced via the intermediate acetyl-CoA, including the group consisting of L-glutamic acid, L-glutamine, L-proline, L-arginine, L-leucine, L-cysteine, succinate and polyhydroxybutyrate. These strains feature PEP-dependent glucose uptake with the EMPP operative. Notably, the activity of phosphofructokinase in the bacterium of U.S. Pat. No. 7,785,858 is reduced compared to that of a wild-type or non-modified strain (see page 33).

There is a need to provide methods, comprising central carbon and product specific pathways, that maximize the conversion of feedstock to product by best accommodating the redox and energetic constraints of enzyme reactions, thereby allowing the energetically efficient production of precursors of acetyl-CoA, one of the most central metabolites in catabolism of many organisms, in particular of microorganisms which can be used for the production of numerous industrially important compounds from renewable resources. Applicants have addressed this need by providing the embodiments as defined in the claims.

Moreover, in the field of biotechnology, there is not only a need to allowing the energetically efficient production of precursors of acetyl-CoA but also a need for the production of erythritol and its precursor D-erythrose. Erythritol is a four-carbon polyol which is used as a biological sweetener with applications in food and pharmaceutical industry. It is also used as a functional sugar substitute in special foods for people with diabetes and obesity. Moreover, erythritol can be safely used as a noncariogenic sweetener in foods as it cannot be fermented by the bacteria that cause dental caries. Erythritol also serves as a starting material for the production of other sugars. Although erythritol can be produced by a chemical process where dialdehyde starch is converted into erythritol by a high-temperature chemical reaction in the presence of a nickel catalyst, the chemical process did not reach to industrialization due to low yields. Therefore, at present, erythritol is produced commercially by microbial methods using mostly osmophilic yeasts. Erythritol is increasing in popularity and there is a growing demand in the food industry. Thus, it becomes increasingly important to produce large quantities of erythritol and in particular its precursors by using biological processes. D-erythrose is a direct precursor of erythritol which can easily be converted into erythritol as described below; see Moon et al., Appl Microbiol. Biotechnol, 86:1017-1025 (2010) for a review. Accordingly, there is an increasing need for the production of D-erythrose, the precursor of erythritol.

The present invention provides a method for the production of D-erythrose and acetyl phosphate comprising the enzymatic conversion of D-fructose and phosphate into D-erythrose and acetyl phosphate by making use of a phosphoketolase. The produced acetyl phosphate, a precursor of acetyl-CoA, may then beneficially be converted into acetyl-CoA as described further below while the produced D-erythrose can be converted into erythritol by methods utilizing enzymes known in the art. As a matter of fact, eukaryotes contain a erythrose reductase that catalyzes the reduction of erythrose to result erythritol by an NAD(P)H-dependent reduction reaction; see Moon et al., Appl Microbiol. Biotechnol, 86:1017-1025 (2010) for a review.

The produced D-erythrose can further be converted into glycolaldehyde by a method for the production of glycolaldehyde comprising the enzymatic conversion of D-erythrose into glycolaldehyde by making use of an aldolase, wherein said aldolase is a 2-deoxyribose-5-phosphate aldolase or a fructose-bisphosphate aldolase. The produced glycolaldehyde can finally be converted into acetyl phosphate by the enzymatic conversion of the thus produced glycolaldehyde into acetyl phosphate by making use of a phosphoketolase or a sulfoacetaldehyde acetyltransferase (EC 2.3.3.15). Starting from D-glucose, the above D-fructose can be obtained by the enzymatic conversion of D-glucose into D-fructose by making use of a glucose-fructose isomerase. The corresponding reactions are schematically shown in FIG. 1. Thus, by performing the above methods, acetyl phosphate is produced which may then be converted into acetyl-CoA by a phosphotransacetylase which can then beneficially be used for the production of metabolites like, e.g., alkenes or acetone derived from acetyl-CoA. The above artificial metabolic route for acetyl-CoA production has the advantage that the yield of acetyl phosphate (and, accordingly, acetyl-CoA) is increased vis-à-vis the natural metabolic pathways. This is because, in the end, starting from glucose as a substrate, 3 acetyl-CoA molecules (without the expense of ATP) are produced while the natural occurring EMMP pathway (glycolysis) yields 2 acetyl-CoA molecules only.

Thus, in one aspect, the present invention relates to a method for the production of D-erythrose and acetyl phosphate comprising the enzymatic conversion of D-fructose and phosphate into D-erythrose and acetyl phosphate by making use of a phosphoketolase according to the following reaction:

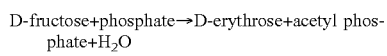

The present inventor surprisingly found that enzymes which are classified as phosphoketolases are capable of catalyzing the enzymatic conversion of D-fructose and phosphate into D-erythrose and acetyl phosphate according to the above reaction. This is surprising since the unphosphorylated form of D-fructose had not been known to be a substrate for phosphoketolases.

Different types of phosphoketolases are known and all of them can be employed in the method according to the invention. Generally, phosphoketolases are classified into two types based on substrate preference as regards their naturally catalyzed reaction: xylulose-5-phosphate (X5P) phosphoketolases, which are classified in EC 4.1.2.9 and which naturally use X5P and fructose-6-phosphate (F6P) as a substrate but which prefer X5P, and X5P/fructose-6-phosphate (F6P) phosphoketolases, which are classified in 4.1.2.22 and which can use both X5P and F6P with comparable activities as substrate (Suzuki et al., J. Biol. Chem. 44 (2010), 34279-34287). In the following, the term "phosphoketolase" always refers to both types.

Thus, X5P phosphoketolases are enzymes which are classified in EC 4.1.2.9 and which are capable of catalyzing the following reaction:

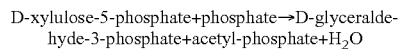

The other type of phosphoketolases which are classified in EC 4.1.2.22 are generally referred to as fructose-6-phosphate phosphoketolases and are naturally capable of catalyzing the following reaction:

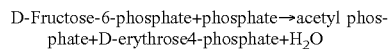

There are also cases in which a phosphoketolase is assigned to both types of phosphoketolases, e.g., in the case of the phosphoketolase from *Nitrolancetus hollandicus* Lb, or where an identified phosphoketolase has not yet been assigned to any of the two types but is simply generally classified as a phosphoketolases. The term "phosphoketolase" when used herein also refers to these phosphoketolases.

Thus, in one embodiment of the method according to the present invention the enzymatic conversion of D-fructose and phosphate into D-erythrose and acetyl phosphate is achieved by making use of a phosphoketolase which is classified as a phosphoketolases in EC 4.1.2.9. This enzyme has been identified in a variety of organisms, in particular microorganisms such as bacteria and fungi. In one preferred embodiment the phosphoketolase (EC 4.1.2.9) originates from a prokaryotic organism, preferably a bacterium. The enzyme has, for example, been described to occur in *Lactococcus lactis*, *Lactobacillus plantarum* (Uniprot Accession numbers: Q88S87; Q88U67), *Lactobacillus pentosus* (Uniprot Accession number: Q937F6), *Lactobacillus reuteri*, *Bifidobacterium animalis* (Uniprot Accession number: A0PAD9), *Bifidobacterium animalis* subsp. *lactis* (Uniprot Accession number: Q9AEM9), *Butyrovibrio fibrisolvens*, *Fibrobacter intestinalis*, *Fibrobacter succinogenes*, *Leuconostoc mesenteroides*, *Oenococcus oeni*, *Starkeya novella*, *Thiobacillus* sp., *Thermobispora bispora* (strain ATCC 19993/DSM 43833/CBS 139.67/JCM 10125/NBRC 14880/R51; Uniprot Accession number D6YAD9), *Thermobaculum terrenum* (strain ATCC BAA-798/YNP1; Uniprot Accession number D1CI63) and *Nitrolancetus hollandicus* Lb (Uniprot Accession number 14EJ52).

In another preferred embodiment the phosphoketolase (EC 4.1.2.9) originates from a eukaryotic organism, preferably a fungus, e.g. a yeast, such as *S. cerevisia*. The enzyme has, for example, been described to occur in *Emericella*

*nidulans* (Uniprot Accession number: Q5B3G7), *Metarhizium anisopliae* (Uniprot Accession number: C1K2N2), *Candida boidinii, Candida curvata, Candida famata, Candida humicola, Candida parapsilosis, Candida parapsilosis* NCYC 926, *Candida tropicalis, Cyberlindnera jadinii, Cyberlindnera saturnus, Debaromyces robertsiae, Fusarium oxysporum, Kluyveromyces marxianus, Kluyveromyces phaseolosporus, Lipomyces starkeyi, Ogataea angusta, Pachysolen tannophilus, Priceomyces medius, Saccharomyces cerevisiae, Rhodospiridium toruloides, Rhodotorula glutinis, Rhodotorula graminis, Penicillium chrysogenum, Trichosporon cutaneum* and *Yarrowia lipolytica*.

The enzymatic activity of a phosphoketolase (EC 4.1.2.9) can be assessed with methods known to a person skilled in the art. Such methods are, e.g., described in Meile et al. (J. Bacteriol. 183 (2001), 2929-2936) and in Suzuki et al (Acta Cryst. F66 (2010), 941-943).

The phosphoketolases (EC 4.1.2.9 and EC 4.1.2.22 generally referred to as xylulose 5-phosphate phosphoketolase and fructose 6-phosphate phosphoketolase, respectively, as described above) are structurally and functionally well defined. For example, as a representative for phosphoketolases of EC 4.1.2.9 and EC 4.1.2.22, Petrareanu et al. (Acta Crystallographica F66 (2010), 805-807) describe the X-ray crystallographic analysis of the xylulose-5-phosphate phosphoketolase from *Lactococcus lactis*, an enzyme which was shown to be active towards both xylulose 5-phosphate and fructose 6-phosphate as substrates.

In another embodiment of the method according to the present invention the enzymatic conversion of D-fructose and phosphate into D-erythrose and acetyl phosphate is achieved by making use of a phosphoketolase which is classified as a fructose-6-phosphate phosphoketolase in EC 4.1.2.22. This enzyme has been identified in a variety of organisms, in particular microorganisms such as bacteria and fungi. In one preferred embodiment the fructose-6-phosphate phosphoketolase (EC 4.1.2.22) originates from a prokaryotic organism, preferably a bacterium. The enzyme has, for example, been described to occur in *Bifidobacterium adolescentis, Bifidobacterium animalis* subsp. *lactis* (Uniprot Accession number: Q9AEM9), *Bifidobacterium longum, Bifidobacterium pseudolongum*, in particular *Bifidobacterium pseudolongum* subsp. *globosum, Bifidobacterium bifidum, Bifidobacterium breve, Bifidobacterium dentium, Bifidobacterium mongoliense, Bifidobacterium bombi, Cupriavidus necator, Gardnerella vaginalis, Gluconacetobacter xylinus, Lactobacillus paraplantarum, Leuconostoc mesenteroides* and *Nitrolancetus hollandicus* Lb (Uniprot Accession number 14EJ52).

In another preferred embodiment the fructose-6-phosphate phosphoketolase (EC 4.1.2.22) originates from a eukaryotic organism, preferably a fungus, e.g. a yeast, such as *S. pastorianus*. The enzyme has, for example, been described to occur in *Candida sp., Candida sp. 107, Candida tropicalis, Rhodotorula glutinis, Rhodotorula graminis* and *Saccharomyces pastorianus*.

The enzyme is structurally and functionally well defined. For example, Suzuki et al. (Acta Crystallographica F66 (2010), 941-943; J. Biol. Chem. 285 (2010), 34279-34287) describe the overexpression, crystallization and X-ray analysis of the phosphoketolase from *Bifidobacterium breve*. The gene encoding the xylulose-5-phosphate/fructose-6-phosphate phosphoketolase from *Bidifobacterium lactis* is e.g. described in Meile et al. (J. Bacteriol. 183 (2001), 2929-2936).

The enzymatic activity of a fructose-6-phosphate phosphoketolase (EC 4.1.2.22) can be assessed with methods known to a person skilled in the art. Such methods are, e.g., described in Meile et al. (J. Bacteriol. 183 (2001), 2929-2936) and in Suzuki et al. (Acta Cryst. F66 (2010), 941-943).

Other phosphoketolases which have not yet been classified into EC 4.2.1.9 or EC 4.2.1.22 and which can be used in the method according to the present invention are, e.g. the phosphoketolase from *Thermosynechococcus elongatus* (strain BP-1; Uniprot Accession number: Q8DJN6), the phosphoketolase from *Bacillus coagulans* 36D1 (Uniprot Accession number: G2TIL0), the phosphoketolase from *Lactococcus lactis* subsp. *lactis* (Strain KF147; Uniprot Accession number: A9QST6), the phosphoketolase from *Bifidobacterium pseudolongum* subsp. *globosum* (Uniprot Accession number: Q6R2Q6) and the phosphoketolase from *Clostridium acetobutylicum* (Strain ATCC 824; Uniprot Accession number: Q97JE3; Servisky et al. (J. Ind. Microbiol. Biotechnol. 39 (2012), 1859-1867); SEQ ID NO: 2).

In the appended Examples, it is shown that the phosphoketolases of *Bifidobacterium pseudolongum* subsp. *globosum* (Uniprot Accession number: Q6R2Q6; SEQ ID NO: 1), of *Clostridium acetobutylicum* (Strain ATCC 824; Uniprot Accession number: Q97JE3; SEQ ID NO: 2) and of *Lactococcus lactis* subsp. *lactis* (Strain KF147; Uniprot Accession number: A9QST6; SEQ ID NO: 3) are capable of converting D-fructose and phosphate into D-erythrose and acetyl phosphate.

In a preferred embodiment, the phosphoketolase employed in the method of the invention has an amino acid sequence as shown in any one of SEQ ID NOs: 1 to 3 or shows an amino acid sequence which is at least x % homologous to any one of SEQ ID NOs: 1 to 3 and has the activity of a phosphoketolase with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting D-fructose and phosphate into D-erythrose and acetyl phosphate as set forth herein above. Preferably, the degree of identity is determined by comparing the respective sequence with the amino acid sequence of any one of the above-mentioned SEQ ID NOs. When the sequences which are compared do not have the same length, the degree of identity preferably either refers to the percentage of amino acid residues in the shorter sequence which are identical to amino acid residues in the longer sequence or to the percentage of amino acid residues in the longer sequence which are identical to amino acid residues in the shorter sequence. The degree of sequence identity can be determined according to methods well known in the art using preferably suitable computer algorithms such as CLUSTAL.

When using the Clustal analysis method to determine whether a particular sequence is, for instance, 80% identical to a reference sequence default settings may be used or the settings are preferably as follows: Matrix: blosum 30; Open gap penalty: 10.0; Extend gap penalty: 0.05; Delay divergent: 40; Gap separation distance: 8 for comparisons of amino acid sequences. For nucleotide sequence comparisons, the Extend gap penalty is preferably set to 5.0.

Preferably, the degree of identity is calculated over the complete length of the sequence.

It has been described that a multiple alignment of phosphoketolase sequences shows several highly conserved regions and two of these regions are used as signature patterns for phosphoketolases (http://prosite.expasy.org/PDOC60002). The first signature pattern is E-G-G-E-L-G-Y and the second signature pattern is G-x(3)-[DN]-x-P-x(2)-[LIVFT]-x(3)-[LIVM]-x-G-D-G-E. The function of the first signature pattern is not yet known while the second signature pattern corresponds to the thiamine pyrophosphate binding site. Thus, in a preferred embodiment, a phosphoketolase as defined herein above has an amino acid sequence which contains at least one of the two above mentioned signature patterns, preferably at least the second signature pattern, and even more preferably both signature patterns.

Sequence comparisons show that the overall sequence identity between phosphoketolases from different origins can be as low as around 26%. For example, Meile et al. (J. Biol. Chem. 183 (2001), 2929-2936) reports that the D-xylulose 5-phosphate/D-fructose 6-phosphate phosphoketolase gene (xfp) of *Bifidobacterium lactis* revealed identities of 26% to 55% to sequences in the genomes of other organisms.

Whether a chosen phosphoketolase is capable of catalyzing the conversion of D-fructose and phosphate into D-erythrose and acetyl phosphate can, e.g., be assessed by an assay as set forth in the appended Examples.

The term "phosphate" as used in connection with the method of the invention refers to a compound which is acceptable as a phosphate source for the enzyme employed in the method for the conversion of D-fructose and phosphate into D-erythrose and acetyl phosphate. One possibility is the provision of phosphate in the form of phosphoric acid, i.e. $H_3PO_4$. However, also other forms are conceivable, in particular salts of phosphoric acid ($H_3PO_4$) in which one, two or three of the hydrogen atoms are replaced by other ions, such as sodium ions.

Phosphoketolases are thiamine diphosphate-dependent enzymes, i.e. they require thiamine diphosphate (also referred to as ThDP or TPP) as a cofactor. Therefore, it is advantageous that in a method according to the invention TPP is provided during the reaction. Moreover, some phosphoketolases require ions, such as $Mg^{2+}$ or $Ca^{2+}$ as cofactors. In such a case, the method according to the invention also includes the presence of such ions during the conversion as described above.

The products of the above-described conversion of D-fructose and phosphate by a phosphoketolase, i.e. D-erythrose and acetyl phosphate, are important metabolites which can be further converted into compounds of interest. The further conversion of acetyl phosphate into compounds of interest will be described further below.

In the following, the conversion of D-erythrose will be further described and, in particular, in a first aspect a conversion of D-erythrose which ultimately leads to two further molecules of acetyl phosphate. In this context, a method is provided which allows converting one molecule of D-erythrose to two molecules of glycolaldehyde. Thus, in another aspect, the present invention also relates to a method for the production of glycolaldehyde comprising the enzymatic conversion of one molecule of D-erythrose into 2 molecules of glycolaldehyde by making use of an aldolase. Examples for suitable aldolases are 2-deoxyribose-5-phosphate aldolase (EC 4.1.2.4) and fructose-bisphosphate aldolase (EC 4.1.2.13).

The present inventor surprisingly found that it is possible to use an aldolase, e.g. a 2-deoxyribose-5-phosphate aldolase (EC 4.1.2.4) or a fructose-bisphosphate aldolase (EC 4.1.2.13), for converting one molecule of D-erythrose into two molecules of glycolaldehyde. This finding is surprising since the reaction which is naturally catalyzed by these enzymes is completely different and involves phosphorylated substrates and it was not known that these enzymes can use D-erythrose as a substrate so as to convert it into glycolaldehyde.

An aldolase which is classified as a 2-deoxyribose-5-phosphate aldolase (EC 4.1.2.4), also referred to as deoxyribose-phosphate aldolase (EC 4.1.2.4), is an enzyme that catalyzes the following reaction:

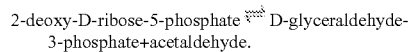
2-deoxy-D-ribose-5-phosphate ⇌ D-glyceraldehyde-3-phosphate+acetaldehyde.

This enzyme belongs to the family of lyases, specifically the aldehyde-lyases, which cleave carbon-carbon bonds. The systematic name of this enzyme class is 2-deoxy-D-ribose-5-phosphate acetaldehyde-lyase (D-glyceraldehyde-3-phosphate-forming). This enzyme is also often referred to as phosphodeoxyriboaldolase, deoxyriboaldolase, deoxyribose-5-phosphate aldolase, 2-deoxyribose-5-phosphate aldolase, and 2-deoxy-D-ribose-5-phosphate acetaldehyde-lyase. This enzyme participates in pentose phosphate pathway.

2-deoxyribose-5-phosphate aldolase (EC 4.1.2.4) has been identified in a variety of organisms, in particular microorganisms such as bacteria. In one preferred embodiment the 2-deoxyribose-5-phosphate aldolase (EC 4.1.2.4) originates from a prokaryotic organism, preferably a bacterium. The enzyme has, for example, been described to occur in *Escherichia coli* (Uniprot Accession number: P0A6L0), *Aeropyrum pernix* (Uniprot Accession number: Q9Y948), *Bacillus subtilis, Klebsiella butylicus* (Uniprot Accession number: A2BLE9), *Klebsiella pneumoniae* (SwissProt Accession number: Q7WT44), *Paenibacillus* sp. (Uniprot Accession number: C7E719), *Streptococcus mutans* (SwissProt Accession number: Q9AIP7), *Thermococcus kodakarensis* (SwissProt Accession number: O87710), and *Yersinia* sp EA015 (Uniprot Accession number: C0LSK9).

In another preferred embodiment the 2-deoxyribose-5-phosphate aldolase (EC 4.1.2.4) originates from a eukaryotic organism. The enzyme has, for example, been described to occur in *Bos Taurus* and *Homo sapiens*.

Moreover, 2-deoxyribose-5-phosphate aldolase (EC 4.1.2.4) has also been identified in *Thermus thermophilus* (strain HB8) (Uniprot Accession Number: Q5SJ28), *Clostridium acetobutylicum* (strain ATCC 824) (Uniprot Accession Number: O97IU5), *Acetobacter* sp. (Uniprot Accession Number: R5Q5K8), *Lactobacillus acidophilus* (strain ATCC 700396) (Uniprot Accession Number: Q5FLZ2), *Staphylococcus aureus* (strain bovine RF122) (Uniprot Accession Number: Q2YUU4), *Bacteroides fragilis* (Uniprot Accession Number: K1GTP0), *Acetobacterium woodii* (strain ATCC 29683) (Uniprot Accession Number: H6LFY1), *Streptococcus gordonii* (strain Challis) (Uniprot Accession Number: A8AX59), *Shewanella oneidensis* (strain MR-1) (Uniprot Accession Number: Q8EHK4), *Neosartorya fumigata* (*Aspergillus fumigatus*) (strain ATCC MYA-4609) (Uniprot Accession Number: A4D9G0), and *Hyperthermus butylicus* (Uniprot Accession Number: A2BLE9).

The enzymatic activity of a 2-deoxyribose-5-phosphate aldolase (EC 4.1.2.4) can be assessed with methods known to a person skilled in the art. Such methods are, e.g., described in DeSantis et al., Biorg. Med. Chem. 11: 43-52 (2003) and Sakuraba et al., Appl. Environ. Microbiol. 73: 7427-7434 (2007). As described therein, the enzymatic activity of a 2-deoxyribose-5-phosphate aldolase may, e.g., be assessed by a 2-deoxyribose-5-phosphate cleavage (retroaldol) assay or an aldol condensation (aldol) assay.

2-deoxyribose-5-phosphate aldolase (EC 4.1.2.4) is structurally and functionally well defined. For example, Heine et al. (J. Mol. Biol. (2004) 343: 1019-1034) describe the crystallographic structure of the bacterial class I 2-deoxyribose-5-phosphate aldolase of *E. coli* by Se-Met multiple anomalous dispersion (MAD) methods at 0.99 Å resolution. Heine et al. and publications therein describe that as it can be expected from primary sequence analysis, the 2-deoxyribose-5-phosphate aldolase from *E. coli* exhibits a typical TIM $(\alpha/\beta)_8$ barrel fold. Structural domain consisting of a TIM beta/alpha barrel found in aldolases is referenced in the InterPro as InterPro IPR013785 (http://www.ebi.ac.uk/interpro/entry/IPR013785).

According to their chemical mechanism, aldolases are divided into two classes. Deoxyribose-5-phosphate aldolase (DERA, EC 4.1.2.4) is one of the class I aldolases. The class I aldolases are cofactor-independent and activate their donor substrates by the formation of a Shiff base with a strictly conserved active site lysine (Dean et al. Adv.Synth.Catal. 349 (2007), p. 1308-1320).

As shown by Heine et al., *E. coli* 2-deoxyribose 5-phosphate aldolase contains two lysine residues in the active site. Lys167 forms the Schiff base intermediate, whereas Lys201, which is in close vicinity to the reactive lysine residue, is responsible for the perturbed pKa of Lys167 and, hence, also a key residue.

Comparison of 2-deoxyribose-5-phosphate aldolase from different organisms with the *E. coli*-2deoxyribose-5-phosphate aldolase revealed the following sequence identity (Heine et al., loc. cit.):

30% with 2-deoxyribose-5-phosphate aldolase from *Thermotoga maritima*, 23% with 2-deoxyribose-5-phosphate aldolase from *Aeropyrum pernix*, 32% with 2-deoxyribose-5-phosphate aldolase from *Thermus thermophilus* and 27% with 2-deoxyribose-5-phosphate aldolase from *Aquifex aeolicus*.

However, despite the low level of sequence identity, active-site environment is similar for all of these enzymes.

Kullartz and Pietruzska (Journal of Biotechnology 161 (2012) p. 174-180) identify a new 2-deoxyribose-5-phosphate aldolase from *Rhodococcus erythropolis* and provide a sequence alignment between this enzyme and 2-deoxyribose 5-phosphate aldolase from *E. coli*. Although the sequences shared low identity (28%) and only 59% similarity, crucial residues of the 2-deoxyribose-5-phosphate aldolase from *E. coli* catalytically active site (DeSantis et al., Biorg. Med. Chem. 11 (2003) p. 43-52) perfectly match the corresponding residues of 2-deoxyribose-5-phosphate aldolase from *R. erythropolis*. Schiff-base-forming residue Lys167 in 2-deoxyribose-5-phosphate aldolase from *E. coli* corresponds to Lys155 in DERA from *R. erythropolis*, whereas the proton shuffling system of Asp102 and Lys176 in *E. coli* matches Asp92 and Lys176 in *R. erythropolis*.

Sequence alignment of representative 2-deoxyribose-5-phosphate aldolase proteins of thermophilic microorganisms, including *A. boonei* (Uniprot Accession Number: B51EU6), *A. pernix* (Uniprot Accession Number: Q9Y948), *P. aerophilum* (Uniprot Accession Number: Q8ZXK7) and *T. maritime* (Uniprot Accession Number: Q9X1P5) showed that the residue Lys127 was highly conserved in the 2-deoxyribose-5-phosphate aldolases, which is essential in forming the Schiff base. Furthermore, the residue Asp92 and Lys185 were also highly conserved in all these enzymes, which were known to be important in proton relays (Yin et al, African journal of Biotechnology, 10 (2011) p. 16260-16266).

The 2-deoxyribose-5-phosphate aldolase (EC 4.1.2.4) employed in the conversion of D-erythrose into glycolaldehyde in a method of the present invention can be any 2-deoxyribose-5-phosphate aldolase (EC 4.1.2.4), from prokaryotic or eukaryotic organisms. In the Example section, a prokaryotic 2-deoxyribose-5-phosphate aldolase is described, i.e., a 2-deoxy-D-ribose-5-phosphate aldolase of *E. coli*, strain K12 (SEQ ID NO:4); Uniprot P0A6L0. As shown in the appended Examples, it was found that 2-deoxyribose-5-phosphate aldolase (EC 4.1.2.4) is capable of using D-erythrose as a substrate and converting it into glycoladehyde. In principle any 2-deoxyribose-5-phosphate aldolase (EC 4.1.2.4) can be employed in the method according to the invention, in particular a 2-deoxyribose-5-phosphate aldolase (EC 4.1.2.4) from prokaryotic or eukaryotic organisms.

In a preferred embodiment, the 2-deoxyribose-5-phosphate aldolase (EC 4.1.2.4) employed in the conversion of D-erythrose into glycolaldehyde in a method of the present invention can be a deoxyribose-phosphate aldolase from *Thermus thermophilus* (strain HB8/ATCC 27634/DSM 579); Uniprot Q5SJ28 (SEQ ID NO:5), a deoxyribose-phosphate aldolase from *Clostridium acetobutylicum* (strain ATCC 824/DSM 792/JCM 1419/LMG 5710/VKM B-1787); Uniprot Q971U5 (SEQ ID NO:6), a deoxyribose-phosphate aldolase from *Acetobacter* sp.; Uniprot R5Q5K8 (SEQ ID NO:7), a deoxyribose-phosphate aldolase from *Lactobacillus acidophilus* (strain ATCC 700396/NCK56/N2/NCFM); Uniprot Q5FLZ2 (SEQ ID NO:8), a deoxyribose-phosphate aldolase from *Hyperthermus butylicus* (strain DSM 5456/JCM 9403); Uniprot A2BLE9 (SEQ ID NO:9), a deoxyribose-phosphate aldolase from *Streptococcus gordonii* (strain Challis/ATCC 35105/CH1/DL1/V288); Uniprot A8AX59 (SEQ ID NO:10), a deoxyribose-phosphate aldolase from *Bacteroides fragilis*; Uniprot K1GTP0 (SEQ ID NO:11), a deoxyribose-phosphate aldolase from *Staphylococcus aureus* (strain bovine RF122/ET3-1); Uniprot Q2YUU4 (SEQ ID NO:12), a deoxyribose-phosphate aldolase from *Acetobacterium woodii* (strain ATCC 29683/DSM 1030/JCM 2381/KCTC 1655); Uniprot H6LFY1 (SEQ ID NO:13 or SEQ ID NO:32), a deoxyribose-phosphate aldolase from *Neosartorya fumigata* (strain ATCC MYA-4609/Af293/CBS 101355/FGSC A1100) (*Aspergillus fumigatus*); Uniprot A4D9G0 (SEQ ID NO:14), or a deoxyribose-phosphate aldolase from *Shewanella oneidensis* (strain MR-1); Uniprot Q8EHK4 (SEQ ID NO:15).

Thus, in a preferred embodiment, the 2-deoxyribose-5-phosphate aldolase (EC 4.1.2.4) employed in the method of the invention for converting D-erythrose into glycolaldehyde has an amino acid sequence as shown in any one of SEQ ID NOs:4 to 15 or shows an amino acid sequence which is at least x % homologous to any of SEQ ID NO:4 to 15 and has the activity of catalyzing the conversion of D-erythrose into glycoladehyde, with x being an integer between 30 and 100, preferably 35, 40, 45, 50, 55, 60, 65, 70, 75, 80, 85, 90, 91, 92, 93, 94, 95, 96, 97, 98 or 99. Preferably, the degree of identity is determined by comparing the respective sequence with the amino acid sequence of any one of the above-mentioned SEQ ID NOs. When the sequences which are compared do not have the same length, the degree of identity preferably either refers to the percentage of amino acid residues in the shorter sequence which are identical to amino acid residues in the longer sequence or to the percentage of amino acid residues in the longer sequence which are identical to amino acid residues in the shorter sequence. The degree of sequence identity can be determined according to methods well known in the art using preferably suitable computer algorithms such as CLUSTAL.

When using the Clustal analysis method to determine whether a particular sequence is, for instance, 80% identical to a reference sequence default settings may be used or the settings are preferably as follows: Matrix: blosum 30; Open gap penalty: 10.0; Extend gap penalty: 0.05; Delay divergent: 40; Gap separation distance: 8 for comparisons of amino acid sequences. For nucleotide sequence comparisons, the Extend gap penalty is preferably set to 5.0.

Preferably, the degree of identity is calculated over the complete length of the sequence.

Whether a chosen 2-deoxyribose-5-phosphate aldolase (EC 4.1.2.4) is capable of catalyzing the conversion of D-erythrose into glycoladehyde can, e.g., be assessed by an assay as set forth in the appended Examples.

As mentioned above, the conversion of one molecule of D-erythrose into two molecules of glycolaldehyde can also be achieved by an enzymatic reaction catalyzed by a fructose-bisphosphate aldolase (EC 4.1.2.13). Fructose-bisphosphate aldolases (EC 4.1.2.13) are enzymes which can catalyze the following reaction:

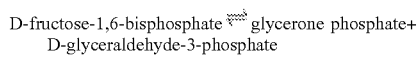

D-fructose-1,6-bisphosphate ⇌ glycerone phosphate+ D-glyceraldehyde-3-phosphate

The enzyme has been identified in a variety of organisms and fructose-1,6-bisphosphate aldolases are divided into two classes, which rely on different reaction mechanisms. Class I fructose-1,6-bisphosphate aldolases are mainly found in animals and higher plants, while Class II fructose-1,6-bisphosphate aldolases are found mainly in algae, bacteria and yeasts. The enzymes belonging to Class II require a bivalent metal ion as a cofactor.

Both type I and type II fructose-1,6-bisphosphate aldolases have been isolated from different prokaryotic and eukaryotic sources and thus, fructose-1,6-bisphosphate aldolase is an ubiquitous glycolytic enzyme that plays a crucial role in glycolysis, gluconeogenesis, and fructose metabolism (Brovetto M. et al. Chem. Rev. 111 (2011), 4346-4403).

Thus, in a preferred embodiment, the fructose-1,6-bisphosphate aldolase (EC 4.1.2.13) originates from a prokaryotic organism, preferably a bacterium. The enzyme has, e.g., been described to occur in *Peptoniphilus asaccharolyticus, Escherichia coli, Thermus aquaticus, Mycobacterium tuberculosis, Aspergillus oryzae, Bacillus cereus, Bacillus subtilis, Clostridium* sp., *Corynebacterium* sp., *Heliobacter pylori, Lactobacillus* sp., *Mycobacterium* sp., *Penicillinum* sp., *Pseudomonas* sp., *Plasmodium falciparum, Saccharomyces* sp. and *Methylococcus cuniculus*.

Moreover, in a preferred embodiment, the fructose 1,6-bisphosphate aldolase (EC 4.1.2.13) originates from a eukaryotic organism. The enzyme has, e.g., been described to occur in *Homo sapiens, Drosophila melanogaster, Oryctolagus cuniculus, Gallus gallus, Zea mays, Bos taurus, Mus musculus,* and *Medicago sativa*.

The study of Siebers et al. firstly revealed that no genes encoding classical Class I and Class II enzymes have been identified in any of the sequenced archaea genomes (Siebers B. et al., J Bol. Chem. 276 (2001), 28710-28718). Later biochemical and structural characterization of aldolases from the two hyperthermophilic archaea, *Thermoproteus tenax* and *Pyrococcus furiosus*, showed that these enzymes use a Schiff-base mechanism and thus belong to the class I aldolases (Siebers et al., loc. cit.; Lorentzen E. et al., Biochem. Soc. Trans. 32 (2004), 259-263).

Class I fructose-1,6-bisphosphate aldolases can be classified into three isoenzyme forms, distinguishable on the basis of immunological reactivity as well as turnover with respect to fructose-1,6-biphosphate and fructose 1-phosphate substrates (Blonski et al., Biochem. J. 323 (1997), 71-77). Isoenzyme A, from rabbit muscle, has been the most extensively studied of the class I fructose-1,6-bisphosphate aldolases (Gefflaut et al., Prog. Biophys. Mol. Biol. 63 (1995), 301-340). Several dozen different isoenzymes have been sequenced and several aldolase isoenzyme structures have been determined, including those from rabbit muscle (Sygusch et al., Proc. Natl. Acad. Sci. 84 (1987), 7846-7850), human muscle (Gamblin et al., FEBS Lett. 262 (1987), 282-286, Arakaki et al., Protein Sci. 13 (2004), 3077-3084) and *Drosophila* (Hester et al., FEBS Lett. 292 (1991), 237-242). With the exception of the 20 amino acid residues comprising the C-terminal region, the molecular architecture of these isoenzymes has been highly conserved. The polypeptide fold of each enzyme subunit of the homotetramer corresponds to that of a β-barrel, with the active site located in the centre of the β-barrel (Sygusch et al., Proc. Natl. Acad. Sci. 84 (1987), 7846-7850). Unlike other β-barrel isoenzymes, the active site is composed of a substantial number of charged amino acid residues, i.e. Asp-33, Lys-107, Lys-146, Glu-187 and Lys-229 (Blonski et al., Biochem. J. 323 (1997), 71-77).

The class II FBP-aldolases require a divalent cation, usually $Zn^{2+}$ and are activated by monovalent cations (Horecker et al., In The Enzymes (Boyer, P. D., ed.), 1972, 3rd edit, vol. 7, 213-258, Academic Press, New York). They share around 15% sequence identity with the class I enzymes (Naismith et al., J. Mol. Biol. 225 (1992), 1137-1141). Hence, in a preferred embodiment, the fructose-1,6-bisphosphate aldolase employed in the method of the invention is provided in the presence of a divalent cation, preferably $Zn^{2+}$ and is activity by monovalent cations.

Class II FBP enzymes can be further categorized into class IIA and class IIB families. Traditionally, class IIA and class IIB FBP enzymes were categorized according to sequence homology and their oligomeric state. Class IIA FBP enzymes were considered dimers, while class IIB FBAs could be dimers, tetramers or octamers. (Izard and Sygush, J. Biol. Chem 279 (2004), 11825-11833; Galkin et al., Biochemistry 48 (2009), 3186-3196; Nakahara et al., Plant Cell Physiol. 44 (2003), 326-333). Alignment of sequences of FBP-proteins showed that members belonging to each family exhibit 40% sequence similarity and amino-acid sequence identity between the type A and B class II FBP aldolases is of the order of 25-30% (Plaumann et al., Curr. Genet. 31 (1997), 430-438). Subsequent sequence alignments of the eight known Class II FBP aldolases showed that Arg-331 is one of the highly conserved residues. Chemical modification and site-directed mutagenesis have confirmed the critical role of this amino acid in the active site (Qamar et al., Protein Sci. 5 (1996), 154-161).

The crystal structure has been determined for several enzymes, i.e. from *E. coli* (Hall et al., J. Mol. Biol. 287 (1999), 383-394), *Thermus aquaticus* (Izard and Sygush; loc. cit.), *Thermus caldophilus* (Lee et al., Biochem. Biophys. Res. Commun. 347 (2006), 616-625), *Giardia lamblia* (Galkin et al.; loc. cit.), *Mycobacterium tuberculosis* (Pegan et al., J. Mol. Biol. 386 (2009), 1038-1053). The secondary structure of *Mycobacterium tuberculosis* FBP aldolase resembles that of the other bacterial class II aldolases (Pegan et al., loc. cit.). The enzyme has an eight-stranded β-sheet core in which each β-strand (β1-β8) is followed in general by an α-helix (α1-α8a), giving rise to an overall (β/α)8-barrel fold, also known as the TIM barrel fold (reference in InterPro database is IPR013785).

In principle, any fructose 1,6-bisphosphate aldolase (EC 4.1.2.13) can be employed in the conversion of D-erythrose into glycolaldehyde according to a method of the invention.

In a preferred embodiment, the fructose-1,6-bisphosphate aldolase (EC 4.1.2.13) employed in a method according to the present invention is the fructose-1,6-bisphosphate aldolase from *Oryctolagus cuniculus* (Uniprot P00883) showing the amino acid sequence as depicted in SEQ ID NO:26 or the fructose-1,6-bisphosphate aldolase from *Escherichia coli* (strain K12) (i.e., a class II fructose-bisphosphate aldolase) (Uniprot P0AB71) showing the amino acid sequence as depicted in SEQ ID NO:27 or the fructose-1,6-bisphosphate aldolase from *Saccharomyces cerevisiae* (strain ATCC 204508/S288c) (Uniprot P14540) showing the amino acid sequence as depicted in SEQ ID NO:28 or the fructose-1,6-bisphosphate aldolase from *Thermus aquaticus* (Uniprot Q9RHA2) showing the amino acid sequence as depicted in SEQ ID NO:29 or the fructose-1,6-bisphosphate aldolase from *Mycobacterium tuberculosis* (Uniprot P67475) showing the amino acid sequence as depicted in SEQ ID NO:30 or the fructose-1,6-bisphosphate aldolase from *Methylococcus capsulatus* (strain ATCC 33009/NCIMB 11132/Bath) (i.e., a class II fructose-bisphosphate aldolase) (Uniprot Q602L6) showing the amino acid sequence as depicted in SEQ ID NO:31.

Thus, in a preferred embodiment, the fructose-1,6-bisphosphate aldolase (EC 4.1.2.13) employed in the method of the invention has the amino acid sequence as shown in any one of SEQ ID NOs: 26 to 31 or shows an amino acid sequence which is at least x % homologous to any one of SEQ ID NOs: 26 to 31 and has the activity of a fructose-1,6-bisphosphate aldolase with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting D-erythrose into glycolaldehyde as set forth herein above. Preferably, the degree of identity is determined as described above.

The enzymatic activity of a fructose-1,6-bisphosphate aldolase (EC 4.1.2.13) can be assessed with methods known to the person skilled in the art. Such methods are, e.g., described in Blonski K. et al., Biochem. J. 323 (1997), 71-77 and Szwergold et al., Arch. Biochem. Biophys. 317 (1995), 244-252.

The present invention also relates to a method wherein the above two enzymatic conversions are combined in subsequent reactions leading to the production of glycolaldehyde and acetyl phosphate from D-fructose. Accordingly, the present invention provides a method for the production of glycolaldehyde and acetyl phosphate from D-fructose comprising (a) the production of D-erythrose and acetyl phosphate from D-fructose and phosphate by making use of a phosphoketolase according to a method of the invention as described above; and further comprising (b) the enzymatic conversion of the thus produced D-erythrose into glycolaldehyde by making use of a 2-deoxyribose-5-phosphate aldolase (EC 4.1.2.4) or a fructose-bisphosphate aldolase (EC 4.1.2.13) according to a method of the invention as described above. As regards the phosphoketolase, the 2-deoxyribose-5-phosphate aldolase (EC 4.1.2.4) and the fructose-bisphosphate aldolase (EC 4.1.2.13), the same applies as has been set forth above in connection with the individual conversions.

The glycolaldehyde produced by the above-described conversion of D-erythrose into glycolaldehyde by making use of a 2-deoxyribose-5-phosphate aldolase or a fructose-bisphosphate aldolase (EC 4.1.2.13) can advantageously be further converted into acetyl phosphate. The overall reaction starting from D-fructose would then yield three molecules of acetyl phosphate.

Thus, in a further aspect of the present invention, the glycolaldehyde produced according to any method as described herein above can be further converted into acetyl phosphate which in itself may serve as a substrate for the production of, e.g., acetyl-CoA, as described further below.

The conversion of glycolaldehyde into acetyl phosphate can be achieved by methods known to the person skilled in the art and, in particular, by an enzymatic reaction catalyzed by a phosphoketolase. The conversion of glycolaldehyde into acetyl phosphate occurs according to the following reaction which is irreversible:

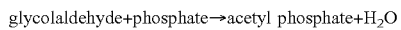

glycolaldehyde+phosphate→acetyl phosphate+H$_2$O

This conversion is described in Melvin et al., J. Biol. Chem. 237: 3841-3842 (1962).

The term "phosphate" as used in connection with the method of the invention refers to a compound which is acceptable as a phosphate source for the enzyme employed in the method for the conversion of glycolaldehyde and phosphate into acetyl phosphate. One possibility is the provision of phosphate in the form of phosphoric acid, i.e. H$_3$PO$_4$. However, also other forms are conceivable, in particular salts of phosphoric acid (H$_3$PO$_4$) in which one, two or three of the hydrogen atoms are replaced by other ions, such as sodium ions.

Thus, a method according to the present invention as described above may further include the step of the enzymatic conversion of the produced glycolaldehyde into acetyl phosphate by making use of a phosphoketolase. Phosphoketolases have already been described above in the context of the enzymatic conversion of D-fructose and phosphate into D-erythrose and acetyl phosphate. The same as set forth above for the phosphoketolases capable of converting D-fructose and phosphate into D-erythrose and acetyl phosphate and for the co-substrate phosphate applies also for the phosphoketolases which can be used for the conversion of glycolaldehyde and phosphate into acetyl phosphate.

Thus, the phosphoketolase employed in the conversion of glycolaldehyde and phosphate into acetyl phosphate can be any phosphoketolase, in particular a phosphoketolase classified as (a) a phosphoketolase (EC 4.1.2.9), or (b) a fructose-6-phosphate phosphoketolase (EC 4.1.2.22). The phosphoketolase employed for converting glycolaldehyde and phosphate into acetyl phosphate can be a phosphoketolase from prokaryotic or eukaryotic organisms. In the Example section, prokaryotic phosphoketolases are described in connection with this conversion, e.g., (a) a phosphoketolase (EC 4.1.2.22) of *Bifidobacterium pseudolongum* subsp. *globosum* (SEQ ID NO:1), or (b) a phosphoketolase from *Clostridium acetobutylicum* (strain ATCC824) (SEQ ID NO:2) or (c) a phosphoketolase of *Lactococcus lactis* subsp. *lactis* (Strain KF147; Uniprot Accession number: A9QST6; SEQ ID NO: 3).

In a preferred embodiment, the phosphoketolase employed in the method of the invention for converting glycolaldehyde and phosphate into acetyl phosphate has an amino acid sequence as shown in any one of SEQ ID NOs:1 to 3 or shows an amino acid sequence which is at least x % homologous to any of SEQ ID NOs:1 to 3 and has the activity of catalyzing the conversion of glycolaldehyde and phosphate into acetyl phosphate, with x being an integer between 30 and 100, preferably 35, 40, 45, 50, 55, 60, 65, 70, 75, 80, 85, 90, 91, 92, 93, 94, 95, 96, 97, 98 or 99. As regards the determination of the degree of identity the same applies as has been set forth above.

Whether a chosen phosphoketolase is capable of catalyzing the conversion of glycolaldehyde and phosphate into acetyl phosphate can, e.g., be determined by an assay as set forth in the appended Examples.

The conversion of glycolaldehyde into acetyl phosphate can also be achieved by an enzymatic reaction catalyzed by a sulfoacetaldehyde acetyltransferase (EC 2.3.3.15) Sulfoacetaldehyde acetyltransferases (EC 2.3.3.15) are enzymes which can catalyze the following reaction:

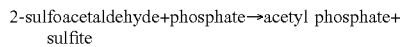

2-sulfoacetaldehyde+phosphate→acetyl phosphate+sulfite

The term "phosphate" as used in connection with the method of the invention refers to a compound which is acceptable as a phosphate source for the enzyme employed in the method for the conversion of 2-sulfoacetaldehyde and phosphate into acetyl phosphate and sulfite. One possibility is the provision of phosphate in the form of phosphoric acid, i.e. $H_3PO_4$. However, also other forms are conceivable, in particular salts of phosphoric acid ($H_3PO_4$) in which one, two or three of the hydrogen atoms are replaced by other ions, such as sodium ions.

The enzyme has been identified in a variety of organisms, in particular bacteria. In one preferred embodiment the sulfoacetaldehyde acetyltransferase (EC 2.3.3.15) originates from a prokaryotic organism, preferably a bacterium. The enzyme has, for example, been described to occur in *Castellaniella defragans* (Uniprot Accession number: Q84H44; previously *Alcaligenes defragans* (Ruff et al., Biochem. J. 369 (2003), 275-285)), *Alcaligenes xylosoxydans* xylosoxydans (Uniprot Accession number: Q84H41), *Desulfonispora thiosulfatigenes* (Uniprot Accession number: Q93PS3), *Rhizobium meliloti* (strain 1021) (Uniprot Accession number: Q92UW6), *Ruegeria pomeroyi* (Uniprot Accession number: Q5LMK2), *Cupriavidus necator* (Uniprot Accession number: Q0K022), *Roseovarius nubinhibens* (Uniprot Accession number: A3SR25), *Acinetobacter* sp. and *Pseudomonas aeruginosa*.

In principle any sulfoacetaldehyde acetyltransferase (EC 2.3.3.15) can be employed in the conversion of glycolaldehyde and phosphate into acetyl phosphate according to a method of the invention.

Sulfoacetaldehyde acetyltransferases are, like phosphoketolases, thiamine pyrophosphate (TPP)-dependent enzymes and therefore are characterized in that they contain a TPP binding domain. Among the sulfoacetaldehyde acetyltransferases known, the TPP binding domain is highly conserved (see, e.g., Ruff et al., Biochem. J. 369 (2003), 275-285). Overall, the known sulfoacetaldehyde acetyltransferases show a high degree of sequence conservation near the N-terminus, including the TPP binding domain (see Ruff et al., loc. cit.). Sequence divergence can be observed in the N-terminus of the enzymes itself and in a region near amino acid 400 of the *C. defragans* enzyme. Ruff et al. (loc. cit.) describe that sulfoacetaldehyde acetyltransferases form 3 subgroups (see FIG. 4 of said publication). Subgroups 2 and 3 are said to show a TPP binding domain conforming with the PROSITE consensus sequence (L/I/V/M/F)(G/S/A)X₅PX₄(L/I/V/M/F/Y/W)X(L/I/V/M/F)XGD(G/S/A)(G/S/A/C), while subgroup slightly deviates from the consensus sequence: (L/I/V/M/F)(G/S/A)X₅PX₄(L/I/V/M/F/Y/W)X(L/I/V/M/F/Y)XGD(G/S/A)(G/S/A/C).

Apart from these regions, the sequence identity between the different sulfoacetaldehyde acetyltransferases can be rather low (down to about 44%).

In a preferred embodiment, the sulfoacetaldehyde acetyltransferase employed in a method according to the present invention is the sulfoacetaldehyde acetyltransferase of *C. defragans* showing the amino acid sequence as depicted in SEQ ID NO:21 or the sulfoacetaldehyde acetyltransferase of *Alcaligenes xylosoxydans xylosoxydans* showing the amino acid sequence as depicted in SEQ ID NO:22 or the sulfoacetaldehyde acetyltransferase of *Desulfonispora thiosulfatigenes* showing the amino acid sequence as depicted in SEQ ID NO:23 or the sulfoacetaldehyde acetyltransferase of *Rhizobium meliloti* (strain 1021) showing the amino acid sequence as depicted in SEQ ID NO:24 or the sulfoacetaldehyde acetyltransferase of *Roseovarius nubinhibens* showing the amino acid sequence as depicted in SEQ ID NO:25 or showing a related amino acid sequence.

Thus, in a preferred embodiment, the sulfoacetaldehyde acetyltransferase employed in the method of the invention has an amino acid sequence as shown in any one of SEQ ID NOs: 21 to 25 or shows an amino acid sequence which is at least x % homologous to any one of SEQ ID NOs: 21 to 25 and has the activity of a sulfoacetaldehyde acetyltransferase with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting glycolaldehyde and phosphate into acetyl phosphate as set forth herein above. Preferably, the degree of identity is determined as described above.

The enzymatic activity of a sulfoacetaldehyde acetyltransferase (EC 2.3.3.15) can be assessed with methods known to a person skilled in the art. Such methods are, e.g., described in Ruff et al. (Biochem. J. 369 (2003), 275-285).

As described above, the present invention relates to the enzymatic conversion of D-fructose into D-erythrose and acetyl phosphate by making use of a phosphoketolase wherein the D-erythrose can optionally be further converted into glycolaldehyde by making use of an aldolase (a 2-deoxyribose-5-phosphate aldolase (EC 4.1.2.4) or a fructose-bisphosphate aldolase (EC 4.1.2.13)) wherein the thus produced glycolaldehyde can optionally be further converted into acetyl phosphate. The D-fructose which is used as a substrate for the production of D-erythrose and acetyl phosphate can be provided externally, i.e. by adding it as a substrate or by using a carbon source which contains D-fructose, or it can itself be provided by an enzymatic conversion. One option in this respect is the enzymatic conversion of D-glucose into D-fructose by methods known to the person skilled in the art. It is, for example, well known that D-glucose can enzymatically be converted into D-fructose by making use of a glucose-fructose isomerase.

Thus, in another embodiment, the present invention also relates to methods as described herein above in which a further step precedes the above step(s) wherein said D-fructose which forms the substrate for the above reaction(s) is itself produced by the enzymatic conversion of D-glucose by making use of a glucose-fructose isomerase. The enzymatic conversion of D-glucose into D-fructose is an enzymatic step which is naturally occurring and utilizes a glucose-fructose isomerase. Glucose-fructose isomerases which may be used in this context are known to the person skilled in the art. Thus, in the present invention, D-glucose can be converted into D-fructose enzymatically, in vitro or in vivo, by making use of a glucose-fructose isomerase.

A "glucose-fructose isomerase" or a "glucose-fructose isomerase activity" as used in the present invention means an enzyme or an enzymatic activity that is capable of converting D-glucose into D-fructose. Such glucose-fructose isomerases are usually classified as a xylose isomerase (EC 5.3.1.5). A xylose isomerase (EC 5.3.1.5) is an enzyme that catalyzes the following reaction:

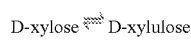

D-xylose ⇌ D-xylulose

Glucose-fructose isomerase (or xylose isomerase) enzymes belong to the family of isomerases, specifically those intramolecular oxidoreductases interconverting aldoses and ketoses. The systematic name of this enzyme class is D-xylose aldose-ketose-isomerase. These enzymes are also referred to as D-xylose isomerase, D-xylose ketoisomerase, and D-xylose ketol-isomerase. This enzyme participates in pentose and glucuronate interconversions and fructose and mannose metabolism. The enzyme is used industrially to convert glucose to fructose in the manufacture of high-fructose corn syrup. It is sometimes also referred to as "glucose isomerase".

The glucose-fructose isomerase (or xylose isomerase) enzyme occurs in a large variety of organism, in particular in prokaryotes, eukaryotes and archae. Thus, in a preferred embodiment of the methods according to the present invention the enzymatic conversion of D-glucose into D-fructose according to the reaction scheme shown above and displayed in FIG. 1 is achieved by making use of a glucose-fructose isomerase (or xylose isomerase) enzyme which is classified as xylose isomerase (EC 5.3.1.5). In one preferred embodiment, the glucose-fructose isomerase originates from a prokaryotic organism, preferably from a bacterium. The enzyme has, for example, been described to occur in *Lactococcus lactis, Bacillus licheniformis, Bacillus* sp. and *E. coli*. In another preferred embodiment, the glucose-fructose isomerase originates from a eukaryotic organism, preferably a fungus, e.g., a yeast such as *Sacharomyces cerevisia*. The enzyme has, for example, been described to occur in *Streptomyces olivochromogenes* (Uniprot Accession number: P15587), *Thermoanaerobacter ethanolicus* (Uniprot Accession number: D2DK62), *Vibrio* sp. (Uniprot Accession number: C7G532), *Actinoplanes missouriensis* (Uniprot Accession number: P12851), *Burkholeria sacchari* (Uniprot Accession number: B6VCW7), *Orpinomyces* sp. (Uniprot Accession number: B7SLY1), *Streptomyces rubiginosus* (Uniprot Accession number: P24300) and *Thermus thermophilus* (P26997).

The glucose-fructose isomerase employed for the conversion of glucose into fructose in a method of the present invention can be any glucose-fructose isomerase, in particular a glucose-fructose isomerase from prokaryotic or eukaryotic organisms. As an example, a glucose-fructose isomerase (or xylose isomerase) from *E. coli* (Uniprot P00944) can be employed having the amino acid sequence of (SEQ ID NO:16).

In a preferred embodiment, glucose-fructose isomerase (or xylose isomerase) employed in the conversion of glucose into fructose in a method of the present invention can be a xylose isomerase from *Bacillus licheniformis* (strain DSM 13/ATCC 14580); Uniprot P77832 (SEQ ID NO:17), a xylose isomerase from *Streptomyces olivochromogenes*; Uniprot P15587 (SEQ ID NO:18), a xylose isomerase from *Thermus thermophilus* (strain HB8/ATCC 27634/DSM 579); Uniprot P26997 (SEQ ID NO:19) or a xylose isomerase from *Candida boidinii*; Uniprot I1VX39 (SEQ ID NO:20).

Thus, in a preferred embodiment, the glucose-fructose isomerase (or xylose isomerase) employed in the method of the invention has an amino acid sequence as shown in any one of SEQ ID NO:16 to 20 or shows an amino acid sequence which is at least x % homologous to any of SEQ ID NO:16 to 20 and has the activity of catalyzing the conversion of D-glucose into D-fructose, with x being an integer between 30 and 100, preferably 35, 40, 45, 50, 55, 60, 65, 70, 75, 80, 85, 90, 91, 92, 93, 94, 95, 96, 97, 98 or 99. As regards the determination of the degree of identity the same applies as has been set forth above.

As mentioned above, the present invention provides a method for the production of D-erythrose. D-erythrose is a direct precursor of erythritol which can be converted into erythritol as described below; see Moon et al., Appl Microbiol. Biotechnol, 86:1017-1025 (2010) for a review. Accordingly, the present invention also provides a method for the production of erythritol from D-erythrose produced by the above methods of the invention. Thus, the present invention provides as a subsequent step a method for the production of erythritol comprising the enzymatic conversion of the produced D-erythrose into erytrhitol by making use of a corresponding enzyme capable of converting D-erythrose into erytrhitol. Enzymes for the conversion of D-erythrose into erythritol are known in the art. As an example, eukaryotes contain a erythrose reductase that catalyzes the reduction of erythrose to result erythritol by an NAD(P)H-dependent reduction reaction; see Moon et al., Appl Microbiol. Biotechnol, 86:1017-1025 (2010) for a review. Such an enzyme may be used in the conversion of D-erythrose into erytrhitol.

The thus produced erythritol may then be used as a biological sweetener with applications in food and pharmaceutical industry. It may also be used as a functional sugar substitute in special foods for people with diabetes and obesity. Moreover, the produced erythritol may be used as a noncariogenic sweetener in foods or may serve as a starting material for the production of other sugars.

As mentioned above, the above described artificial metabolic route (summarized in FIG. 1) may ultimately lead to the production of 3 acetyl phosphate molecules starting from one glucose molecule as a substrate. According to the present invention, the thus produced acetyl phospate according to a method of the present invention can be further converted into desired molecules such as acetate or acetyl-Coenzyme A (also referred to as acetyl-CoA) which is a central metabolite in most organisms.

Thus, in a preferred embodiment, the present invention relates to a method for the production of acetate comprising the production of acetyl phosphate according to any of the methods of the present invention as described above and further comprising the conversion of the thus produced acetyl phosphate into acetate.

The hydrolysis of acetyl phosphate into acetate in vitro occurs spontaneously since acetyl phosphate is rather instable. Acetyl phosphate can also be converted, in vitro or in vivo, enzymatically into acetate, e.g. by making use of an acetate kinase (EC 2.7.2.1), a propionate kinase (EC 2.7.2.15), a butyrate kinase (EC 2.7.2.7) or an acetate kinase (diphosphate) (EC 2.7.2.12).

Acetate kinase is an enzyme which catalyzes the following reaction:

ATP+acetate ⇌ ADP+acetyl phosphate.

Since this reaction is reversible, the enzyme can be employed to convert acetyl phosphate into acetate. The reaction may be pushed into the direction of acetate by continuously removing ATP from the reaction, e.g. by further enzymatic conversion or by removal from the reaction by means and methods known to the person skilled in the art. This enzyme occurs in a large variety of organism, in particular in prokaryotes, eukaryotes and archae. It is an important enzyme in glycolysis and the enzyme levels are normally increased in the presence of excess glucose. In principle any acetate kinase (EC 2.7.2.1) can be used to convert acetyl phosphate into acetate in a method according to the invention.

Also propionate kinase (EC 2.7.2.15) has been described to be able to convert acetyl phosphate into acetate according to the reaction scheme:

ATP+acetate ⇌ ADP+acetyl phosphate.

This enzyme is found in Enterobacteriaceae, such as *E. coli* or *Salmonella enteric* subsp. *enterica serovar. thyphimurium*.

The conversion of acetyl phosphate into acetate can also be achieved by making use of a butyrate kinase (EC 2.7.2.7). Butyrate kinases are enzymes which catalyze the following reaction:

ATP+butanoate ⇌ a ADP+butanoyl phosphate

However, it has been shown for some butyrate kinases, e.g. for those from *Clostridium butyricum* and from *Clostridium acetobutylicum*, that they can also catalyze the reaction:

ATP+acetate ⇌ ADP+acetyl phosphate

Thus, any butyrate kinase which is also capable of catalyzing the reversible conversion of ATP+acetate into ADP+acetyl phosphate can be employed in a method of the present invention for converting acetyl phosphate into acetate.

Moreover, the conversion of acetyl phosphate into acetate can also be achieved by making use of an acetate kinase (diphosphate) (EC 2.7.2.12). Acetate kinases (diphosphate) (EC 2.7.2.12) are enzymes which catalyze the following reaction:

Diphosphate+acetate ⇌ $H_3PO_4$+acetyl phosphate.

This enzyme has been described to occur in *Entamoeba histolytica*.

The enzymatic hydrolysis of acetyl phosphate into acetate and $H_3PO_4$ can also be achieved by making use of an acylphosphatase (EC 3.6.1.7). Acylphosphatase (AcP; EC 3.6.1.7) is a cytosolic enzyme (with a molecular weight of about 10 kDa) widely expressed in eukaryotic and prokaryotic organisms (both mesophilic and extremophilic). AcP can be found in many tissues of vertebrate species in the skeletal muscles and in the heart as muscle-type AcP (MT-AcP) and in erythrocytes, brain and testis as (organ) common-type AcP (CT-AcP) (Zuccotti et al., Acta Cryst. 61 (2005), 144-146). Acylphosphatases catalyze the following reaction:

Acetyl phosphate+$H_2O$→acetate+$H_3PO_4$

This enzyme has been described in a large variety of organisms. Preferably, an acylphosphatase employed in a method according to the present invention is derived from *Gallus gallus, Cavia porcellus* (Liguri et al., Biochem. J. 217 (1984), 499-505), *Homo sapiens, Sus scrofa, Bos taurus, Oryctolagus cuniculus, Equus acallus* or *Pyrococcus hirokoshii* (Miyazoo et al., Acta Crystallographica D60 (2004), 1135-1136).

The structural and functional characteristics of these enzymes have already been studied in detail and are described, e.g., in Liguri et al. (Biochem. J. 217 (1984), 499-505), Miyazoo et al. (Acta Crystallographica D60 (2004), 1135-1136) and in Taddei et al. (FEBS Letters 362 (1995), 175-179).

In another preferred embodiment, the produced acetyl phosphate can also be converted into acetyl-CoA by a phosphotransacetylase while acetyl-CoA may serve as a starting point for the production of many further metabolites like, e.g., alkenes or acetone derived from acetyl-CoA. Accordingly, the present invention relates to a method for the production of acetyl-CoA comprising the production of acetyl phosphate according to any of the methods of the present invention as described above and further comprising (b) the enzymatic conversion of the thus produced acetyl phosphate into acetyl-CoA by making use of a phosphotransacetylase in the presence of a co-enzyme A (CoA).

The conversion of acetyl phosphate into acetyl-CoA (in vitro or in vivo) can be achieved enzymatically, e.g. by the use of phosphate acetyltransferase (EC 2.3.1.8). This enzyme is also referred to as phosphotransacetylase, phosphoacylase or PTA. This enzyme naturally catalyzes the following reaction:

acetyl-CoA+$H_3PO_4$ ⇌ CoA+acetyl phosphate

The enzyme occurs in a multitude of organisms, i.e. in prokayotes, eukaryotes and archae. In principle any known phosphate acetyltransferase (EC 2.3.1.8) can be employed for this conversion.

When referring to "homology" in connection with amino acid or nucleotide sequences, reference is preferably made to sequence identity. The degree of sequence identity can be determined according to methods well known in the art using preferably suitable computer algorithms such as CLUSTAL.

When using the Clustal analysis method to determine whether a particular sequence is, for instance, at least 60% identical to a reference sequence default settings may be used or the settings are preferably as follows: Matrix: blosum 30; Open gap penalty: 10.0; Extend gap penalty: 0.05; Delay divergent: 40; Gap separation distance: 8 for comparisons of amino acid sequences. For nucleotide sequence comparisons, the Extend gap penalty is preferably set to 5.0.

In a preferred embodiment ClustalW2 is used for the comparison of amino acid sequences. In the case of pairwise comparisons/alignments, the following settings are preferably chosen: Protein weight matrix: BLOSUM 62; gap open: 10; gap extension: 0.1. In the case of multiple comparisons/alignments, the following settings are preferably chosen: Protein weight matrix: BLOSUM 62; gap open: 10; gap extension: 0.2; gap distance: 5; no end gap.

Preferably, the degree of identity is calculated over the complete length of the sequence. When the sequences which are compared do not have the same length, the degree of identity either refers to the percentage of residues in the shorter sequence which are identical to residues in the longer sequence or to the percentage of residues in the longer sequence which are identical to residues in the shorter sequence. Preferably, it refers to the percentage of residues in the shorter sequence which are identical to residues in the longer sequence The methods according to the present invention may be carried out in vitro or in vivo. An in vitro reaction is understood to be a reaction in which no cells are employed, i.e. an acellular reaction. Thus, in vitro preferably means in a cell-free system. The term "in vitro" in one embodiment means in the presence of isolated enzymes (or enzyme systems optionally comprising possibly required cofactors). In one embodiment, the enzymes employed in the method are used in purified form.

For carrying out the method in vitro the substrates for the reaction and the enzymes are incubated under conditions (buffer, temperature, cosubstrates, cofactors etc.) allowing the enzymes to be active and the enzymatic conversion to occur. The reaction is allowed to proceed for a time sufficient to produce the respective product. The production of the respective products can be measured by methods known in the art, such as High-Performance Liquid Chromatography (HPLC) possibly linked to Mass Spectrometry (MS) detection.

The enzymes may be in any suitable form allowing the enzymatic reaction to take place. They may be purified or partially purified or in the form of crude cellular extracts or partially purified extracts. It is also possible that the enzymes are immobilized on a suitable carrier.

The Examples illustrate in vitro reactions according to the invention using phosphoketolases and/or aldolases from different origins.

The in vitro method according to the invention may be carried out in a one-pot-reaction, i.e. the substrate is combined in one reaction mixture with the above described enzyme(s) necessary for the desired conversion and the reaction is allowed to proceed for a time sufficient to produce the respective product. Alternatively, the method may also be carried out by effecting one or more enzymatic steps in a consecutive manner, i.e. by first mixing the substrate with one or more enzymes and allowing the reaction to proceed to an intermediate and then adding one or more further enzymes to convert the intermediate further either into an intermediate or into the final product.

The in vitro method according to the invention furthermore may comprise the step of collecting the desired product by recovering it employing methods known in the art.

In another embodiment the method according to the invention is carried out in culture, in the presence of an organism, preferably a microorganism, producing at least one of the enzymes described above which are necessary to produce D-fructose, and/or D-erythrose, and/or glycolaldehyde and/or acetyl phosphate or for further converting the produced acetyl phosphate into other compounds such as acetate or acetyl-CoA, as described herein above. Thus, in another embodiment, the method according to the invention is carried out in culture, in the presence of an organism, preferably a microorganism, producing at least an enzyme described above which is necessary to produce D-fructose according to one of the methods of the invention. Moreover, in another embodiment the method according to the invention is carried out in culture, in the presence of an organism, preferably a microorganism, producing an enzyme described above which is necessary to produce D-erythrose and acetyl phosphate according to one of the methods of the invention. Moreover, in another embodiment the method according to the invention is carried out in culture, in the presence of an organism, preferably a microorganism, producing an enzyme described above which is necessary to produce glycolaldehyde according to one of the methods of the invention. Further, in another embodiment the method according to the invention is carried out in culture, in the presence of an organism, preferably a microorganism, producing at least one of the enzymes described above which are necessary to produce acetyl phosphate according to one of the methods of the invention. A method which employs a microorganism for carrying out a method according to the invention is referred to as "in vivo" method.

The respective substrate may either be provided externally or may be produced by the employed microorganism expressing the corresponding enzyme for the production of the respective substrate as described above. Such a microorganism expresses at least one enzyme for one of the above described enzymatic conversions.

Thus, in such embodiments of the invention, an organism, preferably a microorganism, that produces at least one of the enzymes specified in the description, above, is used. It is possible to use a (micro)organism which naturally produces one or more of the required enzymes and to genetically modify such a (micro)organism so that it expresses also those enzymes which it does not naturally express.

If a (micro)organism is used which naturally expresses one of the required enzyme activities, it is possible to modify such a (micro)organism so that this activity is overexpressed in the (micro)organism. This can, e.g., be achieved by effecting mutations in the promoter region of the corresponding gene so as to lead to a promoter which ensures a higher expression of the gene. Alternatively, it is also possible to mutate the gene as such so as to lead to an enzyme showing a higher activity.

By using (micro)organisms which express the enzymes which are necessary for achieving the enzymatic conversions as described above, it is possible to carry out the method according to the invention directly in the culture medium, without the need to separate or purify the enzymes.

In one embodiment the organism employed in the method according to the invention is an organism, preferably a microorganism, which has been genetically modified to contain one or more foreign nucleic acid molecules encoding one or more of the enzymes as described above. The term "foreign" in this context means that the nucleic acid molecule does not naturally occur in said organism/microorganism. This means that it does not occur in the same structure or at the same location in the organism/microorganism. In one preferred embodiment, the foreign nucleic acid molecule is a recombinant molecule comprising a promoter and a coding sequence encoding the respective enzyme in which the promoter driving expression of the coding sequence is heterologous with respect to the coding sequence. Heterologous in this context means that the promoter is not the promoter naturally driving the expression of said coding sequence but is a promoter naturally driving expression of a different coding sequence, i.e., it is derived from another gene, or is a synthetic promoter or a chimeric promoter. Preferably, the promoter is a promoter heterologous to the organism/microorganism, i.e. a promoter which does naturally not occur in the respective organism/microorganism. Even more preferably, the promoter is an inducible promoter. Promoters for driving expression in different types of organisms, in particular in microorganisms, are well known to the person skilled in the art.

In a further embodiment the nucleic acid molecule is foreign to the organism/microorganism in that the encoded enzyme is not endogenous to the organism/microorganism, i.e. is naturally not expressed by the organism/microorganism when it is not genetically modified. In other words, the encoded enzyme is heterologous with respect to the organism/microorganism. The foreign nucleic acid molecule may be present in the organism/microorganism in extrachromosomal form, e.g. as a plasmid, or stably integrated in the chromosome. A stable integration is preferred. Thus, the genetic modification can consist, e.g. in integrating the corresponding gene(s) encoding the enzyme(s) into the chromosome, or in expressing the enzyme(s) from a plasmid containing a promoter upstream of the enzyme-coding sequence, the promoter and coding sequence preferably originating from different organisms, or any other method known to one of skill in the art.

The organisms used in the invention can be prokaryotes or eukaryotes, preferably, they are microorganisms such as bacteria, yeasts, fungi or molds, or plant cells or animal cells. In a particular embodiment, the microorganisms are bacteria, preferably of the genus *Escherichia* or *Bacillus* and even more preferably of the species *Escherichia coli* or *Bacillus subtilis*.

It is also possible to employ an extremophilic bacterium such as *Thermus thermophilus*, or anaerobic bacteria from the family Clostridiae.

In one embodiment the microorganism is a fungus, more preferably a fungus of the genus *Saccharomyces, Schizosaccharomyces, Aspergillus, Trichoderma, Pichia* or *Kluyveromyces* and even more preferably of the species *Saccharomyces cerevisiae, Schizosaccharomyces pombe, Aspergillus niger, Trichoderma reesei, Pichia pastoris* or of the species *Kluyveromyces lactis*.

In another embodiment, the method according to the invention makes use of a photosynthetic microorganism expressing at least the enzymes which are necessary for achieving the enzymatic conversions as described above. Preferably, the microorganism is a photosynthetic bacterium, or a microalgae. In a further embodiment the microorganism is an algae, more preferably an algae belonging to the diatomeae.

It is also conceivable to use in the method according to the invention a combination of (micro)organisms wherein different (micro)organisms express different enzymes as described above.

In another embodiment the method according to the invention makes use of a multicellular organism expressing at least one of the enzymes which are necessary for achieving the enzymatic conversions as described above. Examples for such organisms are plants or animals.

In a particular embodiment, the method according to the invention involves culturing microorganisms in standard culture conditions (30-37° C. at 1 atm, in a fermenter allowing aerobic growth of the bacteria) or non-standard conditions (higher temperature to correspond to the culture conditions of thermophilic organisms, for example).

When the method according to the invention is carried out in vivo by using an organism/microorganism providing the respective enzyme activities, the organism, preferably microorganism, is cultivated under suitable culture conditions allowing the occurrence of the enzymatic reaction. The specific culture conditions depend on the specific organism/microorganism employed but are well known to the person skilled in the art. The culture conditions are generally chosen in such a manner that they allow the expression of the genes encoding the enzymes for the respective reactions. Various methods are known to the person skilled in the art in order to improve and fine-tune the expression of certain genes at certain stages of the culture such as induction of gene expression by chemical inducers or by a temperature shift.

In another embodiment the organism employed in the method according to the invention is a plant. In principle any possible plant can be used, i.e. a monocotyledonous plant or a dicotyledonous plant. It is preferable to use a plant which can be cultivated on an agriculturally meaningful scale and which allows to produce large amounts of biomass. Examples are grasses like *Lolium*, cereals like rye, wheat, barley, oat, millet, maize, other starch storing plants like potato or sugar storing plants like sugar cane or sugar beet. Conceivable is also the use of tobacco or of vegetable plants such as tomato, pepper, cucumber, egg plant etc. Another possibility is the use of oil storing plants such as rape seed, olives etc. Also conceivable is the use of trees, in particular fast growing trees such as *eucalyptus*, poplar or rubber tree (*Hevea brasiliensis*).

In another embodiment, the method of the invention comprises the step of providing the organism, preferably the microorganism carrying the respective enzyme activity or activities in the form of a (cell) culture, preferably in the form of a liquid cell culture, a subsequent step of cultivating the organism, preferably the microorganism in a fermenter (often also referred to a bioreactor) under suitable conditions allowing the expression of the respective enzyme and further comprising the step of effecting an enzymatic conversion of a method of the invention as described herein above. Suitable fermenter or bioreactor devices and fermentation conditions are known to the person skilled in the art. A bioreactor or a fermenter refers to any manufactured or engineered device or system known in the art that supports a biologically active environment. Thus, a bioreactor or a fermenter may be a vessel in which a chemical/biochemical process like the method of the present invention is carried out which involves organisms, preferably microorganisms and/or biochemically active substances, i.e., the enzyme(s) described above derived from such organisms or organisms harboring the above described enzyme(s). In a bioreactor or a fermenter, this process can either be aerobic or anaerobic. These bioreactors are commonly cylindrical, and may range in size from liters to cubic meters, and are often made of stainless steel. In this respect, without being bound by theory, the fermenter or bioreactor may be designed in a way that it is suitable to cultivate the organisms, preferably microorganisms, in, e.g., a batch-culture, feed-batch-culture, perfusion culture or chemostate-culture, all of which are generally known in the art.

The culture medium can be any culture medium suitable for cultivating the respective organism or microorganism. In a preferred embodiment the culture medium contains fructose or a compound which contains fructose (such as sucrose) and from which fructose can be set free or a compound which can be converted into fructose, such as other hexoses, like e.g. glucose.

As described above, it is possible to use in the method according to the invention a (micro)organism which is genetically modified so as to contain a nucleic acid molecule encoding at least one of the enzymes which are necessary for achieving the enzymatic conversions as described above. Such a nucleic acid molecule encoding an enzyme as described above can be used alone or as part of a vector. The nucleic acid molecules can further comprise expression control sequences operably linked to the polynucleotide comprised in the nucleic acid molecule. The term "operatively linked" or "operably linked", as used throughout the present description, refers to a linkage between one or more expression control sequences and the coding region in the polynucleotide to be expressed in such a way that expression is achieved under conditions compatible with the expression control sequence.

Expression comprises transcription of the heterologous DNA sequence, preferably into a translatable mRNA. Regulatory elements ensuring expression in fungi as well as in bacteria, are well known to those skilled in the art. They encompass promoters, enhancers, termination signals, targeting signals and the like. Examples are given further below in connection with explanations concerning vectors.

Promoters for use in connection with the nucleic acid molecule may be homologous or heterologous with regard to its origin and/or with regard to the gene to be expressed. Suitable promoters are for instance promoters which lend themselves to constitutive expression. However, promoters which are only activated at a point in time determined by external influences can also be used. Artificial and/or chemically inducible promoters may be used in this context.

The vectors can further comprise expression control sequences operably linked to said polynucleotides contained in the vectors. These expression control sequences may be suited to ensure transcription and synthesis of a translatable RNA in bacteria or fungi.

The enzyme(s) used in the methods according to the invention can be a naturally occurring enzyme (i.e., a phosphoketolase, an aldolase, a glucose-fructose isomerase and/or a phosphotransacetylase) or an enzyme which is derived from a naturally occurring enzyme, e.g., be the introduction of mutations or other alterations which, e.g., alter or improve the enzymatic activity, the stability etc.

Methods for modifying and/or improving the desired enzymatic activities of proteins are well-known to the person skilled in the art and include, e.g., random mutagenesis or site-directed mutagenesis and subsequent selection of enzymes having the desired properties or approaches of the so-called "directed evolution".

In addition, it is possible to insert different mutations into the polynucleotides by methods usual in molecular biology (see for instance Sambrook and Russell (2001), Molecular Cloning: A Laboratory Manual, CSH Press, Cold Spring Harbor, N.Y., USA), leading to the synthesis of polypeptides possibly having modified biological properties. The introduction of point mutations is conceivable at positions at which a modification of the amino acid sequence for instance influences the biological activity or the regulation of the polypeptide.

Moreover, mutants possessing a modified substrate or product specificity can be prepared. Preferably, such mutants show an increased activity. Furthermore, the introduction of mutations into the polynucleotides encoding an enzyme as defined above allows the gene expression rate and/or the activity of the enzymes encoded by said polynucleotides to be optimized.

For genetically modifying bacteria or fungi, the polynucleotides encoding an enzyme as defined above or parts of these molecules can be introduced into plasmids which permit mutagenesis or sequence modification by recombination of DNA sequences. Standard methods (see Sambrook and Russell (2001), Molecular Cloning: A Laboratory Manual, CSH Press, Cold Spring Harbor, N.Y., USA) allow base exchanges to be performed or natural or synthetic sequences to be added. DNA fragments can be connected to each other by applying adapters and linkers to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods.

In the context of the present invention, an "increased activity" means that the expression and/or the activity of an enzyme, in particular of the phosphoketolase, the aldolase, the glucose-fructose isomerase and/or the phosphotransacetylase in the genetically modified microorganism is at least 10%, preferably at least 20%, more preferably at least 30% or 50%, even more preferably at least 70% or 80% and particularly preferred at least 90% or 100% higher than in the corresponding non-modified microorganism. In even more preferred embodiments the increase in expression and/or activity may be at least 150%, at least 200% or at least 500%. In particularly preferred embodiments the expression is at least 10-fold, more preferably at least 100-fold and even more preferred at least 1000-fold higher than in the corresponding non-modified microorganism.

The term "increased" expression/activity also covers the situation in which the corresponding non-modified microorganism does not express a corresponding enzyme so that the corresponding expression/activity in the non-modified microorganism is zero.

Methods for measuring the level of expression of a given protein in a cell are well known to the person skilled in the art. In one embodiment, the measurement of the level of expression is done by measuring the amount of the corresponding protein. Corresponding methods are well known to the person skilled in the art and include Western Blot, ELISA etc. In another embodiment the measurement of the level of expression is done by measuring the amount of the corresponding RNA. Corresponding methods are well known to the person skilled in the art and include, e.g., Northern Blot.

Methods for measuring the enzymatic activity of the enzymes employed in the methods according to the invention are known in the art and have already been described above.

The polynucleotide introduced into a (micro)organism is expressed so as to lead to the production of a polypeptide having any of the activities described above. An overview of different expression systems is for instance contained in Methods in Enzymology 153 (1987), 385-516, in Bitter et al. (Methods in Enzymology 153 (1987), 516-544) and in Sawers et al. (Applied Microbiology and Biotechnology 46 (1996), 1-9), Billman-Jacobe (Current Opinion in Biotechnology 7 (1996), 500-4), Hockney (Trends in Biotechnology 12 (1994), 456-463), Griffiths et al., (Methods in Molecular Biology 75 (1997), 427-440). An overview of yeast expression systems is for instance given by Hensing et al. (Antonie van Leuwenhoek 67 (1995), 261-279), Bussineau et al. (Developments in Biological Standardization 83 (1994), 13-19), Gellissen et al. (Antonie van Leuwenhoek 62 (1992), 79-93, Fleer (Current Opinion in Biotechnology 3 (1992), 486-496), Vedvick (Current Opinion in Biotechnology 2 (1991), 742-745) and Buckholz (Bio/Technology 9 (1991), 1067-1072).

Expression vectors have been widely described in the literature. As a rule, they contain not only a selection marker gene and a replication-origin ensuring replication in the host selected, but also a bacterial or viral promoter, and in most cases a termination signal for transcription. Between the promoter and the termination signal there is in general at least one restriction site or a polylinker which enables the insertion of a coding DNA sequence. The DNA sequence naturally controlling the transcription of the corresponding gene can be used as the promoter sequence, if it is active in the selected host organism. However, this sequence can also be exchanged for other promoter sequences. It is possible to use promoters ensuring constitutive expression of the gene and inducible promoters which permit a deliberate control of the expression of the gene. Bacterial and viral promoter sequences possessing these properties are described in detail in the literature. Regulatory sequences for the expression in microorganisms (for instance E. coli, S. cerevisiae) are sufficiently described in the literature. Promoters permitting a particularly high expression of a downstream sequence are for instance the T7 promoter (Studier et al., Methods in Enzymology 185 (1990), 60-89), lacUV5, trp, trp-lacUV5 (DeBoer et al., in Rodriguez and Chamberlin (Eds), Promoters, Structure and Function; Praeger, New York, (1982), 462-481; DeBoer et al., Proc. Natl. Acad. Sci. USA (1983), 21-25), lp1, rac (Boros et al., Gene 42 (1986), 97-100). Inducible promoters are preferably used for the synthesis of polypeptides. These promoters often lead to higher polypeptide yields than do constitutive promoters. In order to obtain an optimum amount of polypeptide, a two-stage process is often used. First, the host cells are cultured under optimum conditions up to a relatively high cell density. In the second step, transcription is induced depending on the type of promoter used. In this regard, a tac promoter is particularly suitable which can be induced by lactose or IPTG (=isopropyl-β-D-thiogalactopyranoside) (deBoer et al., Proc. Natl. Acad. Sci. USA 80 (1983), 21-25). Termination signals for transcription are also described in the literature.

The transformation of the host cell with a polynucleotide or vector according to the invention can be carried out by standard methods, as for instance described in Sambrook and Russell (2001), Molecular Cloning: A Laboratory Manual, CSH Press, Cold Spring Harbor, N.Y., USA; Methods in Yeast Genetics, A Laboratory Course Manual, Cold Spring Harbor Laboratory Press, 1990. The host cell is cultured in nutrient media meeting the requirements of the particular host cell used, in particular in respect of the pH value, temperature, salt concentration, aeration, antibiotics, vitamins, trace elements etc.

The present invention also relates to the use of a phosphoketolase or of a (micro)organism expressing a phosphoketolase for the production of D-erythrose and/or acetyl phosphate from D-fructose. As regards the phosphoketolase and the (micro)organism, the same applies as has been set forth above in connection with a method according to the invention.

The present invention also relates to the use of a 2-deoxyribose-5-phosphate aldolase (EC 4.1.2.4) or a fructose-bisphosphate aldolase (EC 4.1.2.13) or a (micro)organism expressing a 2-deoxyribose-5-phosphate aldolase (EC 4.1.2.4) or expressing a fructose-bisphosphate aldolase (EC 4.1.2.13) as described above for the production of glycolaldehyde from D-erythrose. As regards the 2-deoxyribose-5-phosphate aldolase (EC 4.1.2.4), the fructose-bisphosphate aldolase (EC 4.1.2.13) and the (micro)organism, the same applies as has been set forth above in connection with a method according to the invention.

In a preferred embodiment, the present invention also relates to the use of an organism or microorganism for the production of acetyl phosphate from D-fructose. Thus, in a preferred embodiment, the present invention also relates to the use of an organism or microorganism for the production of acetyl phosphate from D-fructose, wherein said organism or microorganism expresses (i) a phosphoketolase as defined above; and (ii) a 2-deoxyribose-5-phosphate aldolase (EC 4.1.2.4) or a fructose-bisphosphate aldolase (EC 4.1.2.13) as defined above. As regards the phosphoketolase, the 2-deoxyribose-5-phosphate aldolase (EC 4.1.2.4), the fructose-bisphosphate aldolase (EC 4.1.2.13) and the (micro)organism, the same applies as has been set forth above in connection with a method according to the invention.

It is also preferred that the present invention relates to the use of an organism or microorganism for the production of acetyl phosphate from D-glucose. Thus, in a preferred embodiment, the present invention also relates to the use of an organism or microorganism for the production of acetyl phosphate from D-glucose, wherein said organism or microorganism expresses (i) a phosphoketolase as defined above; and (ii) a 2-deoxyribose-5-phosphate aldolase (EC 4.1.2.4) or a fructose-bisphosphate aldolase (EC 4.1.2.13), and wherein said organism or microorganism further expresses (iii) a fructose-glucose isomerase, preferably a xylose isomerase (EC 5.3.1.5). As regards the phosphoketolase, the 2-deoxyribose-5-phosphate aldolase (EC 4.1.2.4), the fructose-bisphosphate aldolase (EC 4.1.2.13), the fructose-glucose isomerase and the (micro)organism, the same applies as has been set forth above in connection with a method according to the invention.

The present invention not only relates to the use of a phosphoketolase or of a (micro)organism expressing a phosphoketolase for the production of D-erythrose and/or acetyl phosphate from D-fructose but also to the use of a combination of a phosphoketolase or of a (micro)organism expressing a phosphoketolase as described above and a 2-deoxyribose-5-phosphate aldolase (EC 4.1.2.4) or a fructose-bisphosphate aldolase (EC 4.1.2.13) or of a (micro)organism expressing a 2-deoxyribose-5-phosphate aldolase (EC 4.1.2.4) or expressing a fructose-bisphosphate aldolase (EC 4.1.2.13) as described above for the production of glycolaldehyde and acetyl phosphate from D-fructose. As regards the phosphoketolase, the 2-deoxyribose-5-phosphate aldolase (EC 4.1.2.4), the fructose-bisphosphate aldolase (EC 4.1.2.13) and the (micro)organism, the same applies as has been set forth above in connection with a method according to the invention.

The present invention also relates to the use of a combination of a phosphoketolase or a (micro)organism expressing a phosphoketolase as described above and a glucose-fructose isomerase or a (micro)organism expressing a glucose-fructose isomerase as described above for the production of acetyl phosphate and D-erythrose from D-glucose. As regards the phosphoketolase, the glucose-fructose isomerase and the (micro)organism, the same applies as has been set forth above in connection with a method according to the invention.

The present invention also relates to the use of a combination of a phosphoketolase or of a (micro)organism expressing a phosphoketolase as described above and a 2-deoxyribose-5-phosphate aldolase (EC 4.1.2.4) or a fructose-bisphosphate aldolase (EC 4.1.2.13) or of a (micro)organism expressing a 2-deoxyribose-5-phosphate aldolase (EC 4.1.2.4) or expressing a fructose-bisphosphate aldolase (EC 4.1.2.13) as described above for the production of acetyl phosphate from D-fructose. As regards the phosphoketolase, the 2-deoxyribose-5-phosphate aldolase (EC 4.1.2.4), the fructose-bisphosphate aldolase (EC 4.1.2.13) and the (micro)organism, the same applies as has been set forth above in connection with a method according to the invention.

The present invention also relates to the use of a combination of a phosphoketolase or of a (micro)organism expressing a phosphoketolase as described above, a 2-deoxyribose-5-phosphate aldolase (EC 4.1.2.4) or a fructose-bisphosphate aldolase (EC 4.1.2.13) or of a (micro)organism expressing a 2-deoxyribose-5-phosphate aldolase (EC 4.1.2.4) or expressing a fructose-bisphosphate aldolase (EC 4.1.2.13) as described above and an glucose-fructose isomerase or of a (micro)organism expressing a glucose-fructose isomerase as described above for the production of acetyl phosphate from D-glucose. As regards the phosphoketolase, the 2-deoxyribose-5-phosphate aldolase (EC 4.1.2.4), the fructose-bisphosphate aldolase (EC 4.1.2.13), the glucose-fructose isomerase and the (micro)organism, the same applies as has been set forth above in connection with a method according to the invention.

The present invention also relates to a composition comprising D-fructose and a phosphoketolase. The present invention also relates to a composition comprising D-fructose and a phosphoketolase and a 2-deoxyribose-5-phosphate aldolase (EC 4.1.2.4) or a fructose-bisphosphate aldolase (EC 4.1.2.13).

The present invention also relates to a composition comprising D-erythrose and a 2-deoxyribose-5-phosphate aldolase (EC 4.1.2.4) or a fructose-bisphosphate aldolase (EC 4.1.2.13). The present invention furthermore relates to a composition comprising D-erythrose and a 2-deoxyribose-5-phosphate aldolase (EC 4.1.2.4) or a fructose-bisphosphate aldolase (EC 4.1.2.13) and a phosphoketolase.

The present invention also relates to a composition comprising D-glucose, a glucose-fructose isomerase and a phosphoketolase and, optionally, also comprising a 2-deoxyribose-5-phosphate aldolase (EC 4.1.2.4) or a fructose-bisphosphate aldolase (EC 4.1.2.13).

Moreover, the present invention also relates to a composition comprising
(i) D-fructose; and
(ii) an organism or microorganism expressing a phosphoketolase as described above.

Preferably, the organism or microorganism also expresses a 2-deoxyribose-5-phosphate aldolase (EC 4.1.2.4) or a fructose-bisphosphate aldolase (EC 4.1.2.13).

Furthermore, the present invention also relates to a composition comprising
(i) D-erythrose; and
(ii) an organism or microorganism expressing a 2-deoxyribose-5-phosphate aldolase (EC 4.1.2.4) or a fructose-bisphosphate aldolase (EC 4.1.2.13) as described above.

Preferably, the organism or microorganism also expresses a phosphoketolase or a sulfoacetaldehyde acetyltransferase (EC 2.3.3.15) as defined above.

The present invention also relates to a composition comprising
(i) D-glucose; and
(ii) an organism or microorganism expressing a glucose-fructose isomerase and expressing a phosphoketolase as described above.

Preferably, the organism or microorganism also expresses a 2-deoxyribose-5-phosphate aldolase (EC 4.1.2.4), a fructose-bisphosphate aldolase (EC 4.1.2.13), and even more preferably also a sulfoacetaldehyde acetyltransferase (EC 2.3.3.15).

As regards preferred embodiments of the components of the above compositions, the same applies as has been set forth above in connection with the method according to the invention.

FIG. 1: shows an artificial metabolic pathway for acetyl phosphate production from D-glucose (or D-fructose) via D-erythrose and glycolaldehyde by making use of a (naturally occurring) glucose-fructose isomerase ("first enzymatic step"), a phosphoketolase ("second enzymatic step"), an aldolase ("third enzymatic step") and a phosphoketolase ("fourth enzymatic step").

Figure 2:
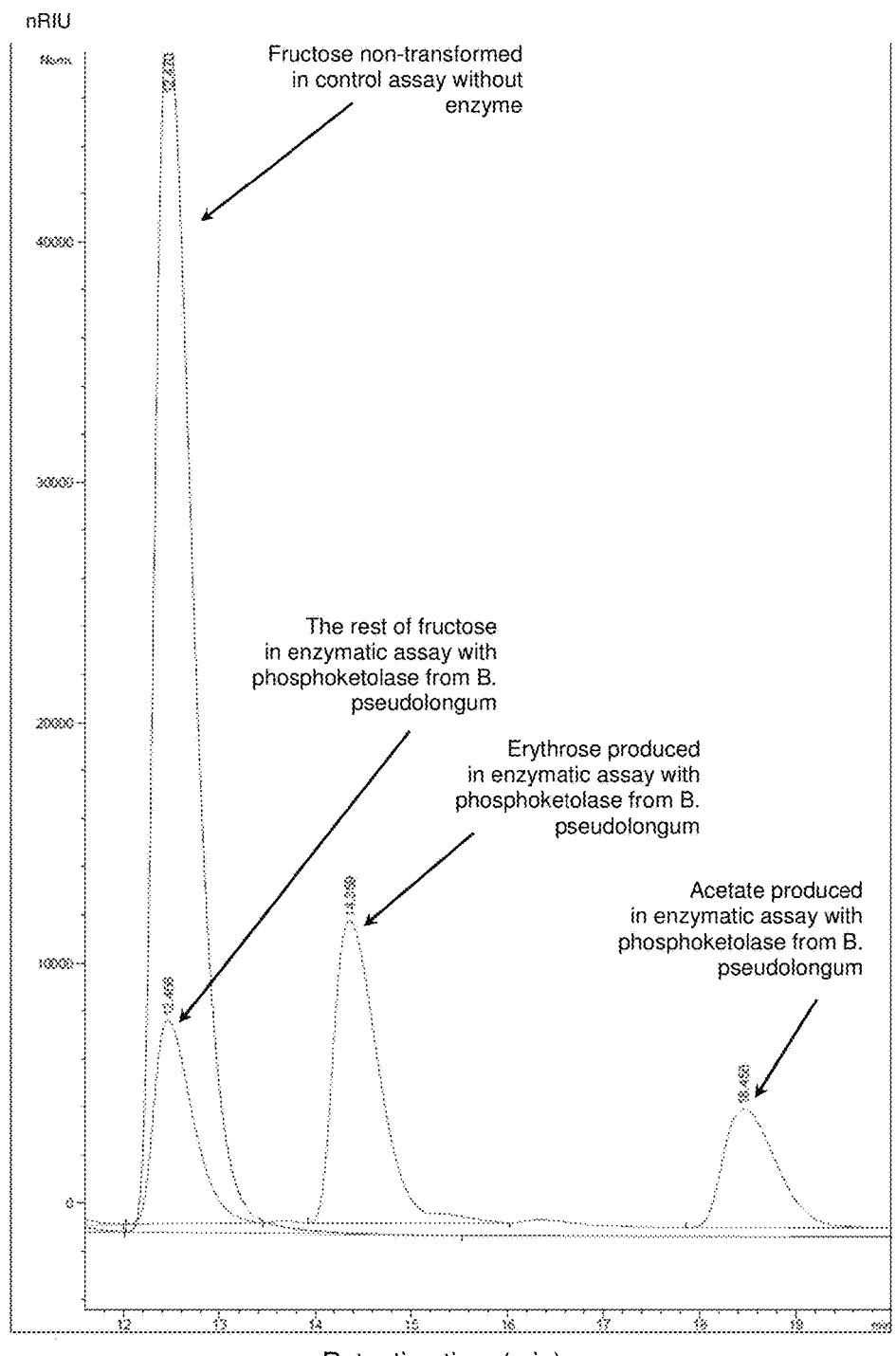

FIG. 2: shows HPLC chromatograms
a) of the reaction mixture in a phosphoketolase assay with a phosphoketolase from *Bifidobacterium pseudolongum* and D-fructose as substrate;
b) of the reaction mixture without enzyme.

Figure 3:
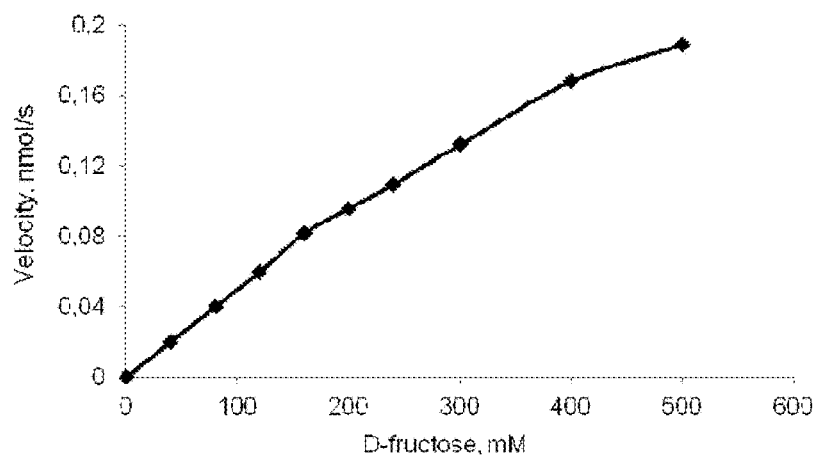

FIG. 3: shows a plot of the velocity as a function of substrate concentration for the phoshoketolase reaction catalyzed by the phosphoketolase of *Bifidobacterium pseudolongum*. Initial rates were computed from the kinetics over 100 minutes of the reaction.

Figure 4:
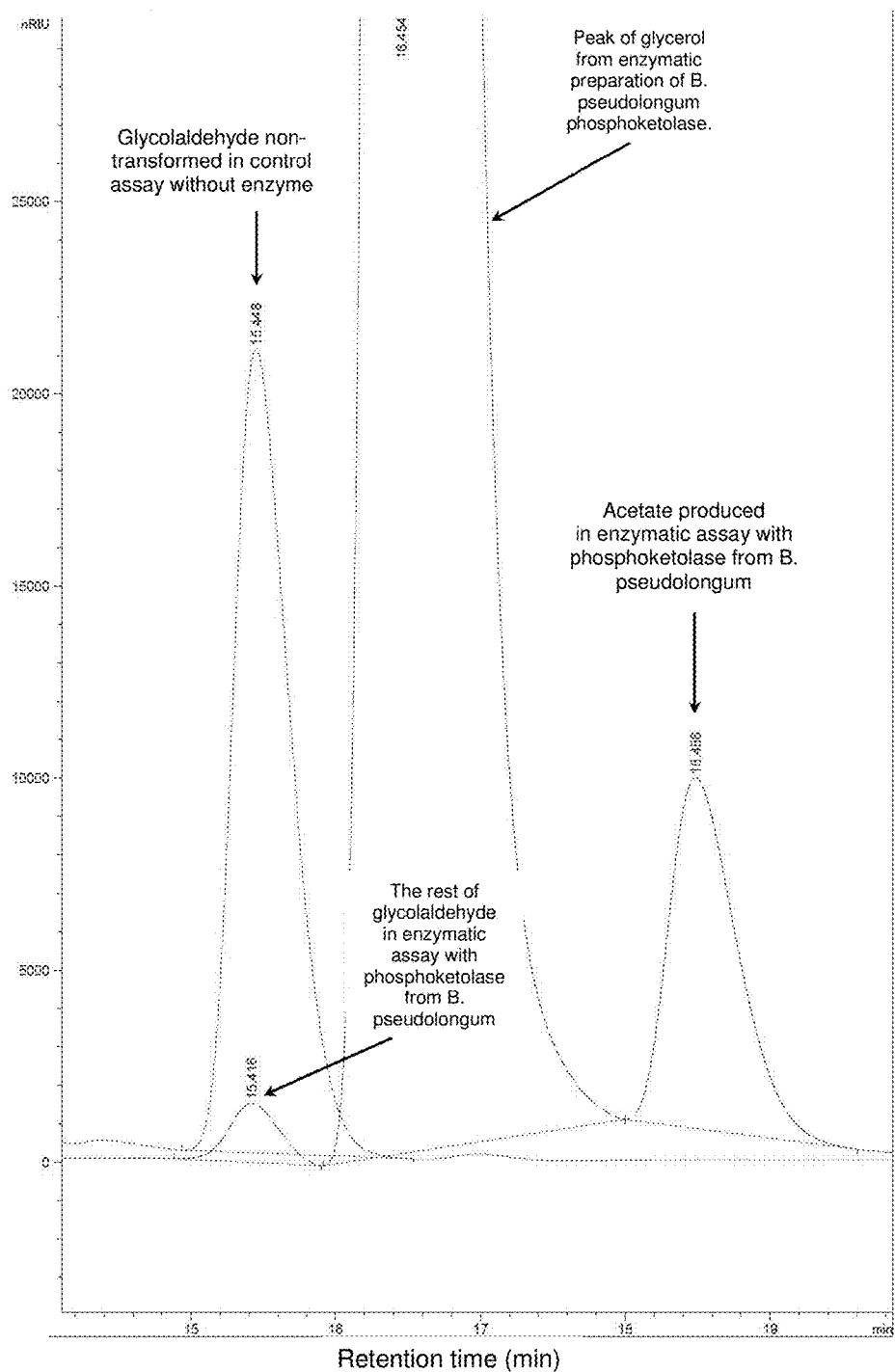

FIG. 4: shows HPLC chromatograms
a) of the reaction mixture in a phosphoketolase assay with the phosphoketolase from *Bifidobacterium pseudolongum* and glycolaldehyde as substrate;
b) of the reaction mixture without enzyme.

Figure 5:
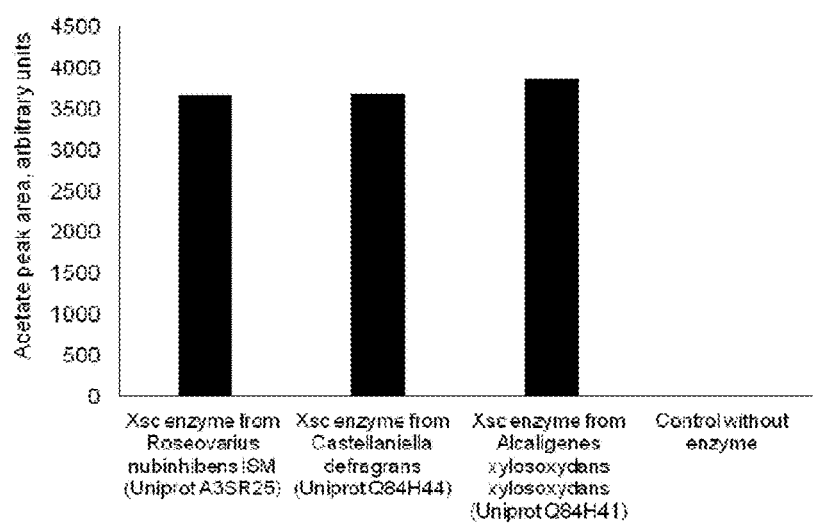

FIG. 5: shows the production of acetate by the hydrolysis of acetyl phosphate, which itself was produced from glycolaldehyde in the presence of phosphate catalyzed by sulfoacetaldehyde acetyltransferases (Xsc).

FIG. 6: shows the production of glycolaldehyde produced from D-erythrose catalyzed by different 2-deoxyribose-5-phosphate aldolases as indicated.

Other aspects and advantages of the invention will be described in the following examples, which are given for purposes of illustration and not by way of limitation. Each publication, patent, patent application or other document cited in this application is hereby incorporated by reference in its entirety.

EXAMPLES

Example 1: Cloning, Expression and Purification of Phosphoketolases

Gene Synthesis, Cloning and Expression of Recombinant Enzymes

The sequences of phosphoketolases inferred from the genomes of prokaryotic organisms were generated by oligonucleotide concatenation to fit the codon usage of *E. coli* (genes were commercially synthesized by GeneArt®). A stretch of 6 histidine codons was inserted after the methionine initiation codon to provide an affinity tag for purification. The genes thus synthesized were cloned in a modified pUC18 expression vector (New England Biolabs) containing a modified Multiple Cloning Sites (MCS). The genes of interest were cloned at PacI and NotI restriction sites. Competent MG1655 *E. coli* cells were transformed with these vectors using standard heat shock procedure. The transformed cells were grown in LB-ampicillin medium for 24 h at 30° C., 160 rpm shaking.

The cells were collected by centrifugation at 4° C., 10,000 rpm for 20 min and the pellets were stored at −80° C.

Protein Purification and Concentration

The pellets from 200 ml of cultured cells were thawed on ice and resuspended in 3 ml of 50 mM Tris-HCl pH 7.5 containing 300 mM NaCl, 5 mM $MgCl_2$, 1 mM DTT and 10 mM Imidazole. 10 µl of lysonase (Merck) was added. Cells were incubated 10 minutes at room temperature and then returned to ice for 20 minutes. Cell lysis was completed by sonication for 2×30 seconds. The bacterial extracts were then clarified by centrifugation at 4° C., 10,000 rpm for 20 min. The clarified bacterial lysates were loaded on PROTINO-1000 Ni-TED column (Macherey-Nagel) allowing adsorption of 6-His tagged proteins. Columns were washed and the enzymes of interest were eluted with 4 ml of 50 mM Tris-HCl pH 7.5 containing 300 mM NaCl, 5 mM $MgCl_2$, 1 mM DTT, 250 mM Imidazole. Eluates were then concentrated, desalted on Amicon Ultra-4 10 kDa filter unit (Millipore) and enzymes were resuspended in 50 mM Tris-HCl pH 7.5. Enzyme preparation was complemented with 10% glycerol prior to long-term storage. Protein concentrations were quantified by direct UV 280 nm measurement on the NanoDrop 1000 spectrophotometer (Thermo Scientific). The purity of proteins thus purified varied from 70% to 90%.

Example 2: Study of Activity of Phosphoketolases with D-Fructose as Substrate Enzymatic Reactions The enzymatic reactions were carried out under the following conditions:
50 mM Tris-HCl pH 7.5
50 mM Sodium phosphate pH 7.5
5 mM Thiamine pyrophosphate (TPP)
5 mM $MgCl_2$
23 mM Sodium fluoride
1.9 mM L-Cysteine hydrochloride
50 mM Fructose (Sigma)
The pH was adjusted to 7.5
Enzyme concentration ranged from 3 to 5 mg/ml.

Control assays were performed in which either no enzyme was added, or no substrate was added.

The ability of phosphoketolase to use D-fructose as substrate was confirmed through the use of up to three analytical methods: the detection of acetate and D-erythrose using HPLC-based analysis and the chemical determination of acetyl phosphate.

HPLC-Based Method

The formation of acetate and D-erythrose from D-fructose in the presence of phosphoketolase was monitored using HPLC-based method. Acetyl phosphate is particularly unstable to hydrolysis, releasing acetate. Therefore, the monitoring of the acetate was chosen as a part of analytical method.

The enzymatic reactions (see description above) were run in total volume of 0.15 ml for 18 hours with shaking at 37° C. and stopped by a 5-min incubation at 80° C. The assays tubes were then centrifuged and 100 µl of the clarified supernatant was transferred into a clean vial. Commercial sodium acetate, D-fructose and D-erythrose (Sigma-Aldrich) were used as references. HPLC analyses were performed using a 1260 Inifinity LC System (Agilent), equipped with a refractometer detector and a column heating module. 10 µl sample was separated on Hi-Plex H column (300×7.7 mm, 8 µm particle size, column temp. 65° C.) equipped with a PL Hi-Plex H Guard Column (50×7.7 mm). The mobile phase consisted of aqueous sulfuric acid (5.5 mM) and was run with a flow rate of 0.6 ml/min. Retention time of D-fructose, D-erythrose and sodium acetate under these conditions was 12.5, 14.4 and 18.5 min, respectively. A typical chromatogram obtained with recombinant phosphoketolase from *Bifidobacterium pseudolongum* is shown in FIG. 2.

The results of HPLC analysis are shown in Table 1. The yields of acetate and D-erythrose indicate the quantitative recovery of the carbon moiety of the D-fructose.

TABLE 1

The products formed from the transformation of 50 mM D-fructose by phosphoketolase (PKT) from different sources.
(The precision and accuracy of HPLC measurement were about 20% and 80-120%, respectively.)

| Reaction | D-fructose, mM (unconsumed) | D-erythrose formed, mM | Acetate formed, mM |
| --- | --- | --- | --- |
| Control without enzyme | 48 mM | 0 mM | 0 mM |
| In the presence of PKT from *Lactococcus lactis* subsp. *lactis* (strain KF147) (Uniprot A9QST6) | 11 mM | 46 mM | 35 mM |

TABLE 1-continued

The products formed from the transformation of 50 mM D-fructose by phosphoketolase (PKT) from different sources.
(The precision and accuracy of HPLC measurement were about 20% and 80-120%, respectively.)

| Reaction | D-fructose, mM (unconsumed) | D-erythrose formed, mM | Acetate formed, mM |
| --- | --- | --- | --- |
| In the presence of PKT from *Bifidobacterium pseudolongum* subsp. *globosum* (Uniprot Q6R2Q6) | 8 mM | 44 mM | 46 mM |
| In the presence of PKT from *Clostridium acetobutylicum* (strain ATCC 824) (Uniprot Q97JE3) | 13 mM | 45 mM | 37 mM |

Kinetics Analysis of Acetyl Phosphate Formation from D-Fructose Using a Hydroxamate-Based Colorimetric Assay The composition of enzymatic reactions was identical to that described above. Kinetic parameters were determined using a range of D-fructose concentrations (0-500 mM) and a constant concentration of sodium phosphate (50 mM).

Each enzymatic reaction was started by adding 3 mg/ml of purified phosphoketolase. Incubations were run for 20, 40, 60, 80, 100 min with shaking at 37° C. Acetyl phosphate concentration was determined through the detection of iron (III) acetyl-hydroxamate using the following procedure (Racker E., Methods Enzymol. 5, 1962, 276-280):

0.1 ml of hydroxylamine hydrochloride (2 M, pH 6.5) was added to 0.1 ml of reaction mixture. After 10 min of incubation at room temperature the samples were acidified with 35 µl of 30% trichloroacetic acid. 35 µl of 8 M HCl and 35 µl of $FeCl_3$ reagent (10% $FeCl_3$ in 0.1 M HCl) were then added. The samples were further clarified by centrifugation and the absorbance of ferric acetyl-hydroxamate complex was measured at 505 nm. A calibration curve was prepared using commercial acetyl phosphate (Sigma-Aldrich). Kinetic parameters obtained for purified recombinant phosphoketolases are presented in Table 2.

TABLE 2

Kinetic parameters of phosphoketolases from different sources with D-fructose as substrate.

| Phosphoketolase | $K_m$, mM | $k_{cat}$, $s^{-1}$ |
| --- | --- | --- |
| *Lactococcus lactis* subsp. *lactis* (strain KF147) (Uniprot A9QST6) | ≈0.25M | 0.11 ± 0.04 |
| *Bifidobacterium pseudolongum* subsp. *globosum* (Uniprot Q6R2Q6) | higher than 0.3M | 0.10 ± 0.02 |

FIG. 3 shows an example of a Michaelis-Menten plot corresponding to the data collecting for phosphoketolase from *Bifidobacterium pseudolongum*.

Example 3: Analysis of Activity of Phosphoketolases with Glycolaldehyde as Substrate Enzymatic Reactions The enzymatic reactions were carried out under the following conditions:
50 mM Tris-HCl pH 7.5
50 mM Sodium phosphate pH 7.5
5 mM Thiamine pyrophosphate (TPP)
5 mM $MgCl_2$
23 mM Sodium fluoride
1.9 mM L-Cysteine hydrochloride 50 mM Glycolaldehyde (Sigma)

The pH was adjusted to 7.5

Enzyme concentration ranged from 3 to 5 mg/ml.

Control assays were performed in which either no enzyme was added, or no substrate was added.

The ability of phosphoketolase to use glycolaldehyde as substrate was confirmed through the use of up to two analytical methods: the detection of acetate using HPLC-based analysis and the chemical determination of acetyl phosphate.

HPLC-Based Method

The enzymatic reactions (see description above) were run for 48 hours with shaking at 37° C. and stopped by a 5-min incubation at 80° C. The assays tubes were then centrifuged and 100 µl of the clarified supernatant was transferred into a clean vial. HPLC analyses were performed on Hi-Plex H column according to the procedure described in Example 2. Commercial sodium acetate and glycolaldehyde (Sigma-Aldrich) were used as references. Retention time of glycolaldehyde under these conditions was 15.4 min.

A significant amount of acetate was produced in the enzymatic assay in the presence of phosphoketolase, no acetate signal was detected in the enzyme-free control reaction.

A typical chromatogram obtained with phosphoketolase from *Bifidobacterium pseudolongum* is showed in FIG. 4.

Analysis of Kinetics of Acetyl Phosphate Formation from Glycolaldehyde Using a Hydroxamate-Based Colorimetric Assay The composition of enzymatic reactions was identical to that described above. Kinetic parameters were determined using a range of glycolaldehyde concentrations (0-100 mM) and a constant concentration of sodium phosphate (50 mM).

Each assay was started by adding 3 mg/ml of purified phosphoketolase. Incubations were run for 20, 40, 60, 80, 100 min with shaking at 37° C. The concentration of acetyl phosphate was determined chemically through the detection of iron (III) acetyl-hydroxamate according to the procedure described in Example 2.

Kinetic parameters obtained for purified recombinant phosphoketolases are presented in Table 3.

TABLE 3

Kinetic parameters of phosphoketolases from different sources with glycolaldehyde as substrate.

| Phosphoketolase | $K_m$, mM | $k_{cat}$, s$^{-1}$ |
| --- | --- | --- |
| *Clostridium acetobutylicum* (strain ATCC 824) (Q97JE3) | ≈30 mM | 0.08 |
| *Bifidobacterium pseudolongum* subsp. *globosum* (Q6R2Q6) | ≈20 mM | 0.07 |
| *Lactococcus lactis* subsp. *lactis* (strain KF147) (Uniprot A9QST6) | ≈25 mM | 0.05 |

Example 4: Expression, and Purification of *E. coli* 2-Deoxy-D-Ribose-5-Phosphate Aldolase Protein Expression The vector pCAN containing the gene coding for *E. coli* 2-deoxy-D-ribose-5-phosphate aldolase (Uniprot P0A6L0) was purchased from NAIST (Nara Institute of Science and Technology, Japan, ASKA collection). Provided vector contained a stretch of 6 histidine codons after the methionine initiation codon.

Competent *E. coli* BL21(DE3) cells (Novagen) were transformed with this vector using standard heat shock procedure. The transformed cells were grown with shaking (160 rpm) on ZYM-5052 auto-induction medium (Studier F W, Prot. Exp. Pur. 41 (2005), 207-234), supplemented with chloramphenicol (25 µg/ml) for 7 hours at 37° C. Protein expression was continued at 18° C. overnight (approximately 12 hours). The cells were collected by centrifugation at 4° C., 10,000 rpm for 20 min and the pellets were frozen at −80° C.

Protein Purification

The pellet from 200 ml of cultured cells was thawed on ice and resuspended in 6 ml of 50 mM Tris-HCl containing 0.5 M NaCl, 5 mM MgCl$_2$, 1 mM DTT and 10 mM Imidazole. 10 µl of lysonase (Merck) was added. Cells were incubated 10 minutes at room temperature and then returned to ice for 20 minutes. Cell lysis was completed by sonication for 2×30 seconds. The bacterial extracts were then clarified by centrifugation at 4° C., 10,000 rpm for 20 min.

2-deoxy-D-ribose-5-phosphate aldolase was purified on PROTINO-1000 Ni-TED column (Macherey-Nagel) according to the manufacturer's recommendations. Eluates, containing the enzyme of interest were then concentrated, desalted on Amicon Ultra-4 10 kDa filter unit (Millipore) and enzyme were resuspended in 50 mM Tris-HCl pH 7.5, complemented with 50 mM NaCl and 10% glycerol. Protein concentrations were quantified by direct UV 280 nm measurement on the NanoDrop 1000 spectrophotometer (Thermo Scientific). The purity of protein thus purified varied from 70% to 90%.

Example 5: Study of Enzymatic Production of Glycolaldehyde from D-Erythrose

The enzymatic reactions were carried out under the following conditions:

50 mM Tris-HCl pH 7.5

50 mM NaCl 10 mM MgCl$_2$ 1 mM DTT 50 mM D-erythrose (Sigma-Aldrich)

The pH was adjusted to 7.5

1 mg of purified 2-deoxy-D-ribose-5-phosphate aldolase was added to 0.2 ml of reaction mixture. Control assays were performed in which either no enzyme was added, or no substrate was added. The reaction mixtures were incubated for overnight (approximately 18 hours) at 37° C. and the reaction was stopped by a 10-min incubation at 80° C.

The assays tubes were then centrifuged and filtered and 100 µl of the clarified supernatant was transferred into a clean vial. HPLC analyses were performed on Hi-Plex H column according to the procedure described in Example 2.

No formation of glycolaldehyde was observed without substrate. The HPLC analysis of reaction without enzyme showed only traces of glycolaldehyde, probably resulted from the spontaneous decomposition of the D-erythrose. The catalytic tests showed a significant increase of glycolaldehyde production in the presence of purified 2-deoxy-D-ribose-5-phosphate aldolase from *E. coli*. The ratio of glycolaldehyde produced after 18 hours incubation in the presence of enzyme versus glycolaldehyde produced in the absence of enzyme is about 9 fold judging from glycolaldehyde peak areas (Table 4). These results clearly indicate that a 2-deoxy-D-ribose-5-phosphate aldolase catalyzes the conversion of D-erythrose to glycolaldehyde.

TABLE 4

Production of glycolaldehyde from D-erythrose.

| Assay | Glycolaldehyde peak area, arbitrary units |
|---|---|
| Without enzyme | $2 \times 10^{-3}$ |
| Enzymatic assay in the presence of 2-deoxy-D-ribose-5-phosphate aldolase from E. coli | $18 \times 10^{-3}$ |

Example 6: Study of the Activity of Sulfoacetaldehyde Acetyltransferases with Glycolaldehyde as a Substrate Gene Cloning and Protein Expression The sequences of sulfoacetaldehyde acetyltransferases (Xsc) inferred from the genome of prokaryotic organisms were generated by oligonucleotide concatenation to fit the codon usage of *E. coli* (genes were commercially synthesized by GeneArt®). A stretch of 6 histidine codons was inserted after the methionine initiation codon to provide an affinity tag for purification. The genes thus synthesized were cloned in a pET-25b(+) expression vector (vectors were constructed by GeneArt®).

Competent *E. coli* BL21 (DE3) cells (Novagen) were transformed with these vectors according to standard heat shock procedure. The transformed cells were grown with shaking (160 rpm) using ZYM-5052 auto-induction medium (Studier F W, Prot. Exp. Pur. 41, (2005), 207-234) for 7 h at 30° C. and protein expression was continued at 18° C. overnight (approximately 16 h). The cells were collected by centrifugation at 4° C., 10,000 rpm for 20 min and the pellets were stored at −80° C.

Protein Purification

Sulfoacetaldehyde acetyltransferases were purified using PROTINO-1000 Ni-TED column (Macherey-Nagel) according to the procedure specified in Example 1 and using 50 mM sodium phosphate pH 7.5 instead of Tris-HCl buffer. Protein concentrations were quantified by direct UV 280 nm measurement on the NanoDrop 1000 spectrophotometer (Thermo Scientific). The purity of proteins thus purified varied from 75% to 90% as estimated by SDS-PAGE analysis.

Enzymatic Assays

The enzymatic assays were carried out under the following conditions:
  50 mM Sodium phosphate pH 7.5
  1 mM Thiamine pyrophosphate (TPP)
  5 mM $MgCl_2$
  50 mM Glycolaldehyde (Sigma-Aldrich)
  The pH was adjusted to 7.5

Each assay was started by adding 5 mg/ml of purified enzyme. Incubations were run for 1 h with shaking at 37° C. Control assays were performed in which either no enzyme was added, or no substrate was added.

The ability of sulfoacetaldehyde acetyltransferases (Xsc) to use glycolaldehyde as a substrate was confirmed through the use of two analytical methods: the chemical determination of acetyl phosphate and the detection of acetate using HPLC-based analysis.

Hydroxamate-Based Colorimetric Assay

Acetyl phosphate was determined through the detection of iron acetyl-hydroxamate according to the procedure described in Example 2.

The concentration of acetyl phosphate produced in enzymatic assays with different sulfoacetaldehyde acetyltransferases is shown in Table 5.

TABLE 5

Production of acetyl phosphate from glycolaldehyde and phosphate catalyzed by different sulfoacetaldehyde acetyltransferases.

| Enzyme | Acetyl phosphate, mM |
|---|---|
| Sulfoacetaldehyde acetyltransferase from *Castellaniella defragrans* (Uniprot Acession Number: Q84H44) | 0.75 |
| Sulfoacetaldehyde acetyltransferase from *Alcaligenes xylosoxydans xylosoxydans* (Uniprot Acession Number: Q84H41) | 1.03 |
| Sulfoacetaldehyde acetyltransferase from *Roseovarius nubinhibens* ISM (Uniprot Acession Number: A3SR25) | 0.85 |

HPLC-Based Method

The enzymatic reactions were run for 1 hour with shaking at 37° C. (see description above) and stopped by a 5-min incubation at 80° C. The assays tubes were then centrifuged and an aliquot of the clarified supernatant was transferred into a clean vial. HPLC analyses were performed on Hi-Plex H column according to the procedure described in Example 2. A significant amount of acetate was produced in the assays with sulfoacetaldehyde acetyltransferases (Xsc) (FIG. 5), no acetate signal was observed neither in the enzyme-free control nor in the assays without substrate.

Overall, these data indicate that sulfoacetaldehyde acetyltransferases from different origins were able to catalyze the formation of acetyl phosphate from glycolaldehyde and phosphate.

Example 7: Conversion of D-Erythrose into Glycolaldehyde Catalyzed by Different 2-Deoxy-D-Ribose-5-Phosphate Aldolases A library of 11 genes encoding representatives of the 2-deoxyribose-5-phosphate aldolases (DeoC, DERA) family from various prokaryotic and eukaryotic organisms was constructed and tested.

Gene Cloning, Protein Expression and Purification

The genes encoding 2-deoxy-D-ribose-5-phosphate aldolases EC 4.1.2.4 were synthesized and cloned in the pET-25b(+) expression vector (vectors were constructed by GeneArt®) as described in Example 6.

The corresponding enzymes were expressed in *E. coli* and purified as specified in Example 4. Each enzyme was tested for its ability to catalyze the production of glycolaldehyde from D-erythrose using the following assay:
  50 mM Tris-HCl pH 7.5
  50 mM D-Erythrose (Sigma-Aldrich)
  10 mM $MgCl_2$
  50 mM NaCl
  1 mM DTT
  Enzyme 5 mg/ml Control assays were performed in which either no enzyme was added, or no substrate was added. The assays were run for 4 h at 37° C. (see description above) and stopped by a 10-min incubation at 95° C. The assay tubes were then centrifuged and an aliquot of clarified supernatant was transferred into a clean vial. HPLC analyses were performed using 1260 Infinity LC System (Agilent), equipped with a refractometer detector and a column heating module. 10 µl of samples were separated using 3 columns connected in series as follows:

1. Hi-Plex guard column (50×7.7 mm, 8 µm particle size) (Agilent)
2. Hi-Plex column (100×7.7 mm, 8 µm particle size) (Agilent)
3. Hi-Plex column (300×7.7 mm, 8 µm particle size, column temp. 70° C.) (Agilent).

The mobile phase consisted of aqueous sulfuric acid (8.4 mM) and was run at 0.5 ml/min. The analyses were performed at 70° C.

Commercial glycolaldehyde (Sigma-Aldrich) was used as a reference. Retention time of erythrose and glycolaldehyde under these conditions were 20.2 and 22 min, respectively.

No glycolaldehyde signal was observed in the assays without substrate. A certain amount of glycolaldehyde was found in commercially provided D-erythrose (see, e.g., FIG. 6, bar "no enzyme"). The 2-deoxy-D-ribose-5-phosphate aldolases assays showed an enzyme-dependent increase of glycolaldehyde production from erythrose judging from glycolaldehyde peak areas (FIG. 6). These data indicate that the cleavage of D-erythrose into glycolaldehyde can be catalyzed by 2-deoxy-D-ribose-5-phosphate aldolases.

The invention claimed is:

1. A method of producing D-erythrose and acetyl phosphate comprising enzymatically converting D-fructose and phosphate into D-erythrose and acetyl phosphate by a phosphoketolase (EC 4.1.2.9) or a fructose-6-phosphate phosphoketolase (EC 4.1.2.22) wherein the phosphoketolase or fructose-6-phosphate phosphoketolase is obtained from fungi or bacteria.

2. The method of claim 1, further comprising enzymatically converting D-erythrose into glycolaldehyde by an aldolase, wherein said aldolase is a 2-deoxyribose-5-phosphate aldolase (EC 4.1.2.4) or a fructose-bisphosphate aldolase (EC 4.1.2.13).

3. The method of claim 2, wherein the method further comprises: enzymatically converting glycolaldehyde into acetyl phosphate by a phosphoketolase (EC 4.1.2.9), a fructose-6-phosphate phosphoketolase (EC 4.1.2.22), or a sulfoacetaldehyde acetyltransferase (EC 2.3.3.15).

4. The method of claim 1, wherein the method further comprises enzymatically converting D-glucose into said D-fructose by a glucose-fructose isomerase.

5. The method of claim 4, wherein said glucose-fructose isomerase is a xylose isomerase (EC 5.3.1.5).

6. The method of claim 1, wherein said method is carried out in vitro.

7. The method of claim 2, wherein said method is carried out in vitro).

8. The method of claim 1, wherein the method is carried out in a microorganism expressing the phosphoketolase (EC 4.1.2.9) or the fructose-6-phosphate phosphoketolase (EC 4.1.2.22).

9. The method of claim 2, wherein the method is carried out in a microorganism expressing the 2-deoxyribose-5-phosphate aldolase (EC 4.1.2.4) or the fructose-bisphosphate aldolase (EC 4.1.2.13).

10. The method of claim 1, wherein the method further comprises enzymatically converting the acetyl phosphate into acetyl-CoA by a phosphotransacetylase in the presence of co-enzyme A (CoA).

11. The method of claim 2, wherein the method further comprises enzymatically converting the acetyl phosphate into acetyl-CoA by a phosphotransacetylase in the presence of co-enzyme A (CoA).

12. The method of claim 3, wherein the method further comprises enzymatically converting the acetyl phosphate into acetyl-CoA by a phosphotransacetylase in the presence of co-enzyme A (CoA).

13. The method of claim 6, wherein the method further comprises enzymatically converting the acetyl phosphate into acetyl-CoA by a phosphotransacetylase in the presence of co-enzyme A (CoA).

14. The method of claim 4, wherein the method further comprises enzymatically converting the acetyl phosphate into acetyl-CoA by a phosphotransacetylase in the presence of co-enzyme A (CoA).

15. The method of claim 5, wherein the method further comprises enzymatically converting the acetyl phosphate into acetyl-CoA by a phosphotransacetylase in the presence of co-enzyme A (CoA).

16. The method of claim 7, wherein the method further comprises enzymatically converting glycolaldehyde into acetyl phosphate by a phosphoketolase (EC 4.1.2.9) or the fructose-6-phosphate phosphoketolase (EC 4.1.2.22) or a sulfoacetaldehyde acetyltransferase (EC 2.3.3.15).

17. The method of claim 4, wherein said method is carried out in vitro.

18. The method of claim 9, wherein the method is carried out in a recombinant microorganism expressing:
  (a) a recombinant phosphoketolase (EC 4.1.2.9) or the fructose-6-phosphate phosphoketolase (EC 4.1.2.22) and/or a recombinant sulfoacetaldehyde acetyltransferase (EC 2.3.3.15); and
  (b) a recombinant 2-deoxyribose-5-phosphate aldolase (EC 4.1.2.4) or a recombinant fructose-bisphosphate aldolase (EC 4.1.2.13);
  and optionally
  (c) a recombinant glucose-fructose isomerase.

19. The method of claim 18, wherein the recombinant microorganism expresses both the recombinant phosphoketolase (EC 4.1.2.9) or the fructose-6-phosphate phosphoketolase (EC 4.1.2.22) and the recombinant sulfoacetaldehyde acetyltransferase (EC 2.3.3.15).

20. The method of claim 4, wherein said method is carried out in a microorganism expressing the recombinant glucose-fructose isomerase.

21. The method of claim 4, wherein said glucose-fructose isomerase is a xylose isomerase (EC 5.3.1.5).

22. The method of claim 18, wherein the recombinant microorganism is genetically modified to overexpress the recombinant phosphoketolase, the recombinant sulfoacetaldehyde acetyltransferase (EC 2.3.3.15), the recombinant 2-deoxyribose-5-phosphate aldolase (EC 4.1.2.4), the recombinant fructose-bisphosphate aldolase (EC 4.1.2.13) and/or the recombinant glucose-fructose isomerase, wherein the genetic modification is selected from:
  (a) operably associating a heterologous promoter with a polynucleotide encoding the phosphoketolase, the sulfoacetaldehyde acetyltransferase (EC 2.3.3.15), the 2-deoxyribose-5-phosphate aldolase (EC 4.1.2.4), the fructose-bisphosphate aldolase (EC 4.1.2.13) and/or the glucose-fructose isomerase;
  (b) transforming a heterologous polynucleotide encoding the phosphoketolase, the sulfoacetaldehyde acetyltransferase (EC 2.3.3.15), the 2-deoxyribose-5-phosphate aldolase (EC 4.1.2.4), the fructose-bisphosphate aldolase (EC 4.1.2.13) and/or the glucose-fructose isomerase into the recombinant microorganism; and/or
  (c) introducing a mutation in the promoter of a polynucleotide encoding the phosphoketolase, the sulfoacetaldehyde acetyltransferase (EC 2.3.3.15), the 2-deoxyribose-5-phosphate aldolase (EC 4.1.2.4), the fructose-bisphosphate aldolase (EC 4.1.2.13), and/or the glucose-fructose isomerase wherein said mutation results in overexpression of the polynucleotide.

23. The method of claim 18, wherein the recombinant microorganism is genetically modified to alter or improve the enzymatic activity of the recombinant phosphoketolase, the recombinant sulfoacetaldehyde acetyltransferase (EC 2.3.3.15), the recombinant 2-deoxyribose-5-phosphate aldolase (EC 4.1.2.4), the recombinant fructose-bisphosphate aldolase (EC 4.1.2.13) and/or the recombinant glucose-fructose isomerase, wherein the genetic modification is selected from:

(a) transforming a heterologous polynucleotide encoding the phosphoketolase, the sulfoacetaldehyde acetyltransferase (EC 2.3.3.15), the 2-deoxyribose-5-phosphate aldolase (EC 4.1.2.4), the fructose-bisphosphate aldolase (EC 4.1.2.13), and/or the glucose-fructose isomerase into the recombinant microorganism; and/or (b) introducing a mutation into a polynucleotide encoding the phosphoketolase, the sulfoacetaldehyde acetyltransferase (EC 2.3.3.15), the 2-deoxyribose-5-phosphate aldolase (EC 4.1.2.4), the fructose-bisphosphate aldolase (EC 4.1.2.13), and/or the glucose-fructose isomerase wherein said mutation alters or improves enzymatic activity.

24. The method of claim 3, wherein the phosphoketolase is different than the phosphoketolase used in converting D-fructose into D-erythrose and acetyl phosphate.

25. The method of claim 10, wherein the method is carried out in vitro.

26. The method of claim 10, wherein the method is carried out in a recombinant microorganism.

27. The method of claim 3, wherein the method is carried out in vitro.

28. The method of claim 3, wherein the method is carried out in a recombinant microorganism.

* * * * *

SEQUENCE LISTING

<160> NUMBER OF SEQ ID NOS: 32

<210> SEQ ID NO 1
<211> LENGTH: 825
<212> TYPE: PRT
<213> ORGANISM: Bifidobacterium pseudolongum
<220> FEATURE:
<223> OTHER INFORMATION: Subspecies globosum

<400> SEQUENCE: 1

```
Met Thr Asn Pro Val Ile Gly Thr Pro Trp Gln Lys Leu Asp Arg Pro
1               5                   10                  15

Val Ser Glu Glu Ala Ile Glu Gly Met Asp Lys Tyr Trp Arg Val Thr
            20                  25                  30

Asn Tyr Met Ser Ile Gly Gln Ile Tyr Leu Arg Ser Asn Pro Leu Met
        35                  40                  45

Lys Glu Pro Phe Thr Arg Asp Val Lys His Arg Leu Val Gly His
    50                  55                  60

Trp Gly Thr Thr Pro Gly Leu Asn Phe Leu Leu Ala His Ile Asn Arg
65                  70                  75                  80

Leu Ile Ala Asp His Gln Gln Asn Thr Val Phe Ile Met Gly Pro Gly
                85                  90                  95

His Gly Gly Pro Ala Gly Thr Ser Gln Ser Tyr Val Asp Gly Thr Tyr
            100                 105                 110

Thr Glu Tyr Tyr Pro Asn Ile Thr Lys Asp Glu Ala Gly Leu Gln Lys
        115                 120                 125

Phe Phe Arg Gln Phe Ser Tyr Pro Gly Gly Ile Pro Ser His Phe Ala
    130                 135                 140

Pro Glu Thr Pro Gly Ser Ile His Glu Gly Gly Glu Leu Gly Tyr Ala
145                 150                 155                 160

Leu Ser His Ala Tyr Gly Ala Val Met Asn Asn Pro Ser Leu Phe Val
                165                 170                 175

Pro Cys Ile Ile Gly Asp Gly Glu Ala Glu Thr Gly Pro Leu Ala Thr
            180                 185                 190

Gly Trp Gln Ser Asn Lys Leu Val Asn Pro Arg Thr Asp Gly Ile Val
        195                 200                 205

Leu Pro Ile Leu His Leu Asn Gly Tyr Lys Ile Ala Asn Pro Thr Ile
    210                 215                 220

Leu Ala Arg Ile Ser Asp Glu Glu Leu His Asp Phe Phe Arg Gly Met
225                 230                 235                 240

Gly Tyr His Pro Tyr Glu Phe Val Ala Gly Phe Asp Asn Glu Asp His
                245                 250                 255

Met Ser Ile His Arg Arg Phe Ala Glu Leu Phe Glu Thr Ile Phe Asp
            260                 265                 270
```

-continued

```
Glu Ile Cys Asp Ile Lys Ala Ala Gln Thr Asp Asp Met Thr Arg
    275                 280                 285
Pro Phe Tyr Pro Met Leu Ile Phe Arg Thr Pro Lys Gly Trp Thr Cys
290                 295                 300
Pro Lys Phe Ile Asp Gly Lys Lys Thr Glu Gly Ser Trp Arg Ala His
305                 310                 315                 320
Gln Val Pro Leu Ala Ser Ala Arg Asp Thr Glu Glu His Phe Glu Val
                325                 330                 335
Leu Lys Gly Trp Leu Glu Ser Tyr Lys Pro Glu Glu Leu Phe Asn Ala
            340                 345                 350
Asp Gly Ser Ile Lys Asp Val Thr Ala Phe Met Pro Lys Gly Asp
        355                 360                 365
Leu Arg Ile Gly Ala Asn Pro Asn Ala Asn Gly Gly Val Ile Arg Glu
    370                 375                 380
Asp Leu Lys Leu Pro Glu Leu Asp Gln Tyr Glu Val Thr Gly Val Lys
385                 390                 395                 400
Glu Tyr Gly His Gly Trp Gly Gln Val Glu Ala Pro Arg Ser Leu Gly
                405                 410                 415
Ala Tyr Cys Arg Asp Ile Ile Lys Asn Asn Pro Asp Ser Phe Arg Ile
            420                 425                 430
Phe Gly Pro Asp Glu Thr Ala Ser Asn Arg Leu Asn Ala Thr Tyr Glu
        435                 440                 445
Val Thr Asp Lys Gln Trp Asp Asn Gly Tyr Leu Ser Ser Leu Val Asp
    450                 455                 460
Glu His Met Ala Val Thr Gly Gln Val Thr Glu Gln Leu Ser Glu His
465                 470                 475                 480
Gln Cys Glu Gly Phe Leu Glu Ala Tyr Leu Leu Thr Gly Arg His Gly
                485                 490                 495
Ile Trp Ser Ser Tyr Glu Ser Phe Val His Val Ile Asp Ser Met Leu
            500                 505                 510
Asn Gln His Ala Lys Trp Leu Glu Ala Thr Val Arg Glu Ile Pro Trp
        515                 520                 525
Arg Lys Pro Ile Ser Ser Val Asn Leu Leu Val Ser Ser His Val Trp
    530                 535                 540
Arg Gln Asp His Asn Gly Phe Ser His Gln Asp Pro Gly Val Thr Ser
545                 550                 555                 560
Val Leu Ile Asn Lys Thr Phe Asn Asn Asp His Val Thr Asn Ile Tyr
                565                 570                 575
Phe Ala Thr Asp Ala Asn Met Leu Leu Ala Ile Ser Glu Lys Cys Phe
            580                 585                 590
Lys Ser Thr Asn Lys Ile Asn Ala Ile Phe Ala Gly Lys Gln Pro Ala
        595                 600                 605
Pro Thr Trp Ile Thr Leu Asp Glu Ala Arg Ala Glu Leu Glu Ala Gly
    610                 615                 620
Ala Ala Glu Trp Lys Trp Ala Ser Asn Ala Glu Asn Asp Glu Val
625                 630                 635                 640
Gln Val Val Leu Ala Ala Gly Asp Val Pro Thr Gln Glu Ile Met
                645                 650                 655
Ala Ala Ser Asp Ala Leu Asn Lys Met Gly Ile Lys Phe Lys Val Val
            660                 665                 670
Asn Val Val Asp Leu Leu Lys Leu Gln Ser Arg Glu Asn Asn Asp Glu
        675                 680                 685
```

```
Ala Leu Thr Asp Glu Glu Phe Thr Asp Leu Phe Thr Ala Asp Lys Pro
    690                 695                 700

Val Leu Phe Ala Tyr His Ser Tyr Ala Gln Asp Val Arg Gly Leu Ile
705                 710                 715                 720

Tyr Asp Arg Pro Asn His Asp Asn Phe Asn Val Val Gly Tyr Lys Glu
                725                 730                 735

Gln Gly Ser Thr Thr Thr Pro Phe Asp Met Val Arg Val Asn Asp Met
            740                 745                 750

Asp Arg Tyr Ala Leu Gln Ala Ala Leu Lys Met Ile Asp Ala Asp
        755                 760                 765

Lys Tyr Ala Asp Lys Ile Asp Glu Leu Asn Ala Phe Arg Gln Lys Ala
    770                 775                 780

Phe Gln Phe Ala Val Asp Asn Gly Tyr Asp Ile Pro Glu Phe Thr Asp
785                 790                 795                 800

Trp Val Tyr Pro Asp Val Lys Val Asp Glu Thr Gln Met Leu Ser Ala
                805                 810                 815

Thr Ala Ala Thr Ala Gly Asp Asn Glu
            820                 825

<210> SEQ ID NO 2
<211> LENGTH: 796
<212> TYPE: PRT
<213> ORGANISM: Clostridium acetobutylicum

<400> SEQUENCE: 2

Met Gln Ser Ile Ile Gly Lys His Lys Asp Glu Gly Lys Ile Thr Pro
1               5                   10                  15

Glu Tyr Leu Lys Lys Ile Asp Ala Tyr Trp Arg Ala Ala Asn Phe Ile
                20                  25                  30

Ser Val Gly Gln Leu Tyr Leu Leu Asp Asn Pro Leu Leu Arg Glu Pro
            35                  40                  45

Leu Lys Pro Glu His Leu Lys Arg Lys Val Val Gly His Trp Gly Thr
    50                  55                  60

Ile Pro Gly Gln Asn Phe Ile Tyr Ala His Leu Asn Arg Val Ile Lys
65                  70                  75                  80

Lys Tyr Asp Leu Asp Met Ile Tyr Val Ser Gly Pro Gly His Gly Gly
                85                  90                  95

Gln Val Met Val Ser Asn Ser Tyr Leu Asp Gly Thr Tyr Ser Glu Val
            100                 105                 110

Tyr Pro Asn Val Ser Arg Asp Leu Asn Gly Leu Lys Lys Leu Cys Lys
        115                 120                 125

Gln Phe Ser Phe Pro Gly Gly Ile Ser Ser His Met Ala Pro Glu Thr
    130                 135                 140

Pro Gly Ser Ile Asn Glu Gly Gly Glu Leu Gly Tyr Ser Leu Ala His
145                 150                 155                 160

Ser Phe Gly Ala Val Phe Asp Asn Pro Asp Leu Ile Thr Ala Cys Val
                165                 170                 175

Val Gly Asp Gly Glu Ala Glu Thr Gly Pro Leu Ala Thr Ser Trp Gln
            180                 185                 190

Ala Asn Lys Phe Leu Asn Pro Val Thr Asp Gly Ala Val Leu Pro Ile
        195                 200                 205

Leu His Leu Asn Gly Tyr Lys Ile Ser Asn Pro Thr Val Leu Ser Arg
    210                 215                 220

Ile Pro Lys Asp Glu Leu Glu Lys Phe Phe Glu Gly Asn Gly Trp Lys
225                 230                 235                 240
```

```
Pro Tyr Phe Val Glu Gly Glu Asp Pro Glu Thr Met His Lys Leu Met
            245                 250                 255

Ala Glu Thr Leu Asp Ile Val Thr Glu Ile Leu Asn Ile Gln Lys
            260                 265                 270

Asn Ala Arg Glu Asn Asn Asp Cys Ser Arg Pro Lys Trp Pro Met Ile
            275                 280                 285

Val Leu Arg Thr Pro Lys Gly Trp Thr Gly Pro Lys Phe Val Asp Gly
            290                 295                 300

Val Pro Asn Glu Gly Ser Phe Arg Ala His Gln Val Pro Leu Ala Val
305                 310                 315                 320

Asp Arg Tyr His Thr Glu Asn Leu Asp Gln Leu Glu Glu Trp Leu Lys
                    325                 330                 335

Ser Tyr Lys Pro Glu Glu Leu Phe Asp Glu Asn Tyr Arg Leu Ile Pro
                    340                 345                 350

Glu Leu Glu Glu Leu Thr Pro Lys Gly Asn Lys Arg Met Ala Ala Asn
                    355                 360                 365

Leu His Ala Asn Gly Gly Leu Leu Arg Glu Leu Arg Thr Pro Asp
            370                 375                 380

Phe Arg Asp Tyr Ala Val Asp Val Pro Thr Pro Gly Ser Thr Val Lys
385                 390                 395                 400

Gln Asp Met Ile Glu Leu Gly Lys Tyr Val Arg Asp Val Val Lys Leu
                    405                 410                 415

Asn Glu Asp Thr Arg Asn Phe Arg Ile Phe Gly Pro Asp Glu Thr Met
                    420                 425                 430

Ser Asn Arg Leu Trp Ala Val Phe Glu Gly Thr Lys Arg Gln Trp Leu
            435                 440                 445

Ser Glu Ile Lys Glu Pro Asn Asp Glu Phe Leu Ser Asn Asp Gly Arg
            450                 455                 460

Ile Val Asp Ser Met Leu Ser Glu His Leu Cys Glu Gly Trp Leu Glu
465                 470                 475                 480

Gly Tyr Leu Leu Thr Gly Arg His Gly Phe Phe Ala Ser Tyr Glu Ala
                    485                 490                 495

Phe Leu Arg Ile Val Asp Ser Met Ile Thr Gln His Gly Lys Trp Leu
                    500                 505                 510

Lys Val Thr Ser Gln Leu Pro Trp Arg Lys Asp Ile Ala Ser Leu Asn
            515                 520                 525

Leu Ile Ala Thr Ser Asn Val Trp Gln Gln Asp His Asn Gly Tyr Thr
            530                 535                 540

His Gln Asp Pro Gly Leu Leu Gly His Ile Val Asp Lys Lys Pro Glu
545                 550                 555                 560

Ile Val Arg Ala Tyr Leu Pro Ala Asp Ala Asn Thr Leu Leu Ala Val
                    565                 570                 575

Phe Asp Lys Cys Leu His Thr Lys His Lys Ile Asn Leu Leu Val Thr
                    580                 585                 590

Ser Lys His Pro Arg Gln Gln Trp Leu Thr Met Asp Gln Ala Val Lys
            595                 600                 605

His Val Glu Gln Gly Ile Ser Ile Trp Asp Trp Ala Ser Asn Asp Lys
            610                 615                 620

Gly Gln Glu Pro Asp Val Val Ile Ala Ser Cys Gly Asp Thr Pro Thr
625                 630                 635                 640

Leu Glu Ala Leu Ala Ala Val Thr Ile Leu His Glu His Leu Pro Glu
                    645                 650                 655
```

-continued

Leu Lys Val Arg Phe Val Asn Val Val Asp Met Met Lys Leu Leu Pro
                660                 665                 670

Glu Asn Glu His Pro His Gly Leu Ser Asp Lys Asp Tyr Asn Ala Leu
            675                 680                 685

Phe Thr Thr Asp Lys Pro Val Ile Phe Ala Phe His Gly Phe Ala His
        690                 695                 700

Leu Ile Asn Gln Leu Thr Tyr His Arg Glu Asn Arg Asn Leu His Val
705                 710                 715                 720

His Gly Tyr Met Glu Gly Thr Ile Thr Thr Pro Phe Asp Met Arg
                725                 730                 735

Val Gln Asn Lys Leu Asp Arg Phe Asn Leu Val Lys Asp Val Val Glu
            740                 745                 750

Asn Leu Pro Gln Leu Gly Asn Arg Gly Ala His Leu Val Gln Leu Met
        755                 760                 765

Asn Asp Lys Leu Val Glu His Asn Gln Tyr Ile Arg Glu Val Gly Glu
        770                 775                 780

Asp Leu Pro Glu Ile Thr Asn Trp Gln Trp His Val
785                 790                 795

<210> SEQ ID NO 3
<211> LENGTH: 822
<212> TYPE: PRT
<213> ORGANISM: Lactococcus lactis
<220> FEATURE:
<223> OTHER INFORMATION: Subspecies lactis

<400> SEQUENCE: 3

Met Thr Glu Tyr Asn Ser Glu Ala Tyr Leu Lys Lys Leu Asp Lys Trp
1               5                   10                  15

Trp Arg Ala Ala Thr Tyr Leu Gly Ala Gly Met Ile Phe Leu Lys Glu
                20                  25                  30

Asn Pro Leu Phe Ser Val Thr Gly Thr Pro Ile Lys Ala Glu Asn Leu
            35                  40                  45

Lys Ala Asn Pro Ile Gly His Trp Gly Thr Val Ser Gly Gln Thr Phe
        50                  55                  60

Leu Tyr Ala His Ala Asn Arg Leu Ile Asn Lys Tyr Asn Gln Lys Met
65                  70                  75                  80

Phe Tyr Met Gly Gly Pro Gly His Gly Gln Ala Met Val Val Pro
                85                  90                  95

Ser Tyr Leu Asp Gly Ser Tyr Thr Glu Ala Tyr Pro Glu Ile Thr Gln
                100                 105                 110

Asp Leu Glu Gly Met Ser Arg Leu Phe Lys Arg Phe Ser Phe Pro Gly
            115                 120                 125

Gly Ile Gly Ser His Met Thr Ala Gln Thr Pro Gly Ser Leu His Glu
        130                 135                 140

Gly Gly Glu Leu Gly Tyr Val Leu Ser His Ala Thr Gly Ala Ile Leu
145                 150                 155                 160

Asp Gln Pro Glu Gln Ile Ala Phe Ala Val Val Gly Asp Gly Glu Ala
                165                 170                 175

Glu Thr Gly Pro Leu Met Thr Ser Trp His Ser Ile Lys Phe Ile Asn
            180                 185                 190

Pro Lys Asn Asp Gly Ala Ile Leu Pro Ile Leu Asp Leu Asn Gly Phe
        195                 200                 205

Lys Ile Ser Asn Pro Thr Leu Phe Ala Arg Thr Ser Asp Val Asp Ile
        210                 215                 220

-continued

Arg Lys Phe Phe Glu Gly Leu Gly Tyr Ser Pro Arg Tyr Ile Glu Asn
225                 230                 235                 240

Asp Asp Ile His Asp Tyr Met Ala Tyr His Lys Leu Ala Ala Glu Val
            245                 250                 255

Phe Asp Lys Ala Ile Glu Asp Ile His Gln Ile Gln Lys Asp Ala Arg
            260                 265                 270

Glu Asp Asn Arg Tyr Gln Asn Gly Glu Ile Pro Ala Trp Pro Ile Val
        275                 280                 285

Ile Ala Arg Leu Pro Lys Gly Trp Gly Pro Arg Tyr Asn Asp Trp
290                 295                 300

Ser Gly Pro Lys Phe Asp Gly Lys Gly Met Pro Ile Glu His Ser Phe
305                 310                 315                 320

Arg Ala His Gln Val Pro Leu Pro Leu Ser Ser Lys Asn Met Gly Thr
            325                 330                 335

Leu Pro Glu Phe Val Lys Trp Met Thr Ser Tyr Gln Pro Glu Thr Leu
            340                 345                 350

Phe Asn Ala Asp Gly Ser Leu Lys Glu Leu Arg Asp Phe Ala Pro
        355                 360                 365

Lys Gly Glu Met Arg Met Ala Ser Asn Pro Val Thr Asn Gly Gly Val
370                 375                 380

Asp Tyr Ser Asn Leu Val Leu Pro Asp Trp Gln Glu Phe Ala Asn Pro
385                 390                 395                 400

Ile Ser Glu Asn Asn Arg Gly Lys Leu Leu Pro Asp Thr Asn Asp Asn
            405                 410                 415

Met Asp Met Asn Val Leu Ser Lys Tyr Phe Ala Glu Ile Val Lys Leu
        420                 425                 430

Asn Pro Thr Arg Phe Arg Leu Phe Gly Pro Asp Glu Thr Met Ser Asn
        435                 440                 445

Arg Phe Trp Glu Met Phe Lys Val Thr Asn Arg Gln Trp Met Gln Val
    450                 455                 460

Ile Lys Asn Pro Asn Asp Glu Phe Ile Ser Pro Glu Gly Arg Ile Ile
465                 470                 475                 480

Asp Ser Gln Leu Ser Glu His Gln Ala Glu Gly Trp Leu Glu Gly Tyr
            485                 490                 495

Thr Leu Thr Gly Arg Thr Gly Val Phe Ala Ser Tyr Glu Ser Phe Leu
            500                 505                 510

Arg Val Val Asp Ser Met Leu Thr Gln His Phe Lys Trp Ile Arg Gln
        515                 520                 525

Ala Ala Asp Gln Lys Trp Arg His Asp Tyr Pro Ser Leu Asn Val Ile
530                 535                 540

Ser Thr Ser Thr Val Phe Gln Gln Asp His Asn Gly Tyr Thr His Gln
545                 550                 555                 560

Asp Pro Gly Met Leu Thr His Leu Ala Glu Lys Lys Ser Asp Phe Ile
            565                 570                 575

Arg Gln Tyr Leu Pro Ala Asp Gly Asn Thr Leu Leu Ala Val Phe Asp
        580                 585                 590

Arg Ala Phe Gln Asp Arg Ser Lys Ile Asn His Ile Val Ala Ser Lys
        595                 600                 605

Gln Pro Arg Gln Gln Trp Phe Thr Lys Glu Ala Glu Lys Leu Ala
    610                 615                 620

Thr Asp Gly Ile Ala Thr Ile Asp Trp Ala Ser Thr Ala Lys Asp Gly
625                 630                 635                 640

Glu Ala Val Asp Leu Val Phe Ala Ser Ala Gly Ala Glu Pro Thr Ile

```
                    645                 650                 655
Glu Thr Leu Ala Ala Leu His Leu Val Asn Glu Val Phe Pro Gln Ala
                660                 665                 670
Lys Phe Arg Tyr Val Asn Val Val Glu Leu Gly Arg Leu Gln Lys Lys
            675                 680                 685
Lys Gly Ala Leu Asn Gln Glu Arg Glu Leu Ser Asp Glu Glu Phe Glu
        690                 695                 700
Lys Tyr Phe Gly Pro Ser Gly Thr Pro Val Ile Phe Gly Phe His Gly
705                 710                 715                 720
Tyr Glu Asp Leu Ile Glu Ser Ile Phe Tyr Gln Arg Gly His Asp Gly
                725                 730                 735
Leu Ile Val His Gly Tyr Arg Glu Asp Gly Asp Ile Thr Thr Thr Tyr
                740                 745                 750
Asp Met Arg Val Tyr Ser Glu Leu Asp Arg Phe His Gln Ala Ile Asp
                755                 760                 765
Ala Met Gln Val Leu Tyr Val Asn Arg Lys Val Asn Gln Gly Leu Ala
            770                 775                 780
Lys Ala Phe Ile Asp Arg Met Glu Arg Thr Leu Val Lys His Phe Glu
785                 790                 795                 800
Val Thr Arg Asn Glu Gly Val Asp Ile Pro Glu Phe Thr Glu Trp Val
                805                 810                 815
Trp Ser Asp Leu Lys Lys
            820

<210> SEQ ID NO 4
<211> LENGTH: 259
<212> TYPE: PRT
<213> ORGANISM: Escherichia coli
<220> FEATURE:
<223> OTHER INFORMATION: Deoxyribose-phosphate aldolase Escherichia coli
      (strain K12)

<400> SEQUENCE: 4

Met Thr Asp Leu Lys Ala Ser Ser Leu Arg Ala Leu Lys Leu Met Asp
1               5                   10                  15
Leu Thr Thr Leu Asn Asp Asp Thr Asp Glu Lys Val Ile Ala Leu
                20                  25                  30
Cys His Gln Ala Lys Thr Pro Val Gly Asn Thr Ala Ala Ile Cys Ile
            35                  40                  45
Tyr Pro Arg Phe Ile Pro Ile Ala Arg Lys Thr Leu Lys Glu Gln Gly
        50                  55                  60
Thr Pro Glu Ile Arg Ile Ala Thr Val Thr Asn Phe Pro His Gly Asn
65                  70                  75                  80
Asp Asp Ile Asp Ile Ala Leu Ala Glu Thr Arg Ala Ala Ile Ala Tyr
                85                  90                  95
Gly Ala Asp Glu Val Asp Val Val Phe Pro Tyr Arg Ala Leu Met Ala
                100                 105                 110
Gly Asn Glu Gln Val Gly Phe Asp Leu Val Lys Ala Cys Lys Glu Ala
            115                 120                 125
Cys Ala Ala Ala Asn Val Leu Leu Lys Val Ile Glu Thr Gly Glu
        130                 135                 140
Leu Lys Asp Glu Ala Leu Ile Arg Lys Ala Ser Glu Ile Ser Ile Lys
145                 150                 155                 160
Ala Gly Ala Asp Phe Ile Lys Thr Ser Thr Gly Lys Val Ala Val Asn
                165                 170                 175
```

```
Ala Thr Pro Glu Ser Ala Arg Ile Met Met Glu Val Ile Arg Asp Met
                180                 185                 190

Gly Val Glu Lys Thr Val Gly Phe Lys Pro Ala Gly Val Arg Thr
            195                 200                 205

Ala Glu Asp Ala Gln Lys Tyr Leu Ala Ile Ala Asp Glu Leu Phe Gly
210                 215                 220

Ala Asp Trp Ala Asp Ala Arg His Tyr Arg Phe Gly Ala Ser Ser Leu
225                 230                 235                 240

Leu Ala Ser Leu Leu Lys Ala Leu Gly His Gly Asp Gly Lys Ser Ala
                245                 250                 255

Ser Ser Tyr

<210> SEQ ID NO 5
<211> LENGTH: 220
<212> TYPE: PRT
<213> ORGANISM: Thermus thermophilus HB8
<220> FEATURE:
<223> OTHER INFORMATION: Deoxyribose-phosphate aldolase Thermus
      thermophilus (strain HB8)

<400> SEQUENCE: 5

Met Asp Leu Ala Ala His Ile Asp His Thr Leu Leu Lys Pro Thr Ala
1               5                   10                  15

Thr Leu Glu Glu Val Ala Lys Ala Ala Glu Glu Ala Leu Glu Tyr Gly
            20                  25                  30

Phe Tyr Gly Leu Cys Ile Pro Pro Ser Tyr Val Ala Trp Val Arg Ala
        35                  40                  45

Arg Tyr Pro His Ala Pro Phe Arg Leu Val Thr Val Val Gly Phe Pro
    50                  55                  60

Leu Gly Tyr Gln Glu Lys Glu Val Lys Ala Leu Glu Ala Ala Leu Ala
65                  70                  75                  80

Cys Ala Arg Gly Ala Asp Glu Val Asp Met Val Leu His Leu Gly Arg
                85                  90                  95

Ala Lys Ala Gly Asp Leu Asp Tyr Leu Glu Ala Glu Val Arg Ala Val
            100                 105                 110

Arg Glu Ala Val Pro Gln Ala Val Leu Lys Val Ile Leu Glu Thr Gly
        115                 120                 125

Tyr Phe Ser Pro Glu Glu Ile Ala Arg Leu Ala Glu Ala Ala Ile Arg
    130                 135                 140

Gly Gly Ala Asp Phe Leu Lys Thr Ser Thr Gly Phe Gly Pro Arg Gly
145                 150                 155                 160

Ala Ser Leu Glu Asp Val Ala Leu Leu Val Arg Val Ala Gln Gly Arg
                165                 170                 175

Ala Gln Val Lys Ala Ala Gly Gly Ile Arg Asp Arg Glu Thr Ala Leu
            180                 185                 190

Arg Met Leu Lys Ala Gly Ala Ser Arg Leu Gly Thr Ser Ser Gly Val
        195                 200                 205

Ala Leu Val Ala Gly Glu Gly Gly Thr Leu Gly Tyr
    210                 215                 220

<210> SEQ ID NO 6
<211> LENGTH: 215
<212> TYPE: PRT
<213> ORGANISM: Clostridium acetobutylicum
<220> FEATURE:
<223> OTHER INFORMATION: Deoxyribose-phosphate aldolase Clostridium
      acetobutylicum (strain ATCC 824 / DSM 792 / JCM 1419 / LMG 5710 /
      VKM B-1787)
```

<400> SEQUENCE: 6

```
Met Asn Ile Ala Lys Ile Ile Asp His Thr Ala Leu Lys Pro Asp Thr
1               5                   10                  15

Thr Lys Glu Gln Ile Leu Lys Leu Ile Glu Glu Ala Lys Gln Asn Asn
            20                  25                  30

Phe Ala Ser Val Cys Val Asn Pro Lys Trp Val Lys Glu Ala Ser Cys
                35                  40                  45

Ala Leu Lys Asp Ser Ser Val Lys Val Cys Thr Val Ile Gly Phe Pro
    50                  55                  60

Leu Gly Ala Asn Thr Thr Ala Thr Lys Val Phe Glu Thr Gln Asp Ala
65                  70                  75                  80

Ile Lys Asn Gly Ala Glu Val Asp Met Val Val Ser Ile Gly Glu
                85                  90                  95

Leu Lys Asp Lys Asn Asp Asp Tyr Val Glu Lys Asp Ile Glu Glu Val
                100                 105                 110

Val Lys Ala Ala Ser Gly Lys Ala Leu Val Lys Val Ile Ile Glu Thr
            115                 120                 125

Cys Leu Leu Thr Glu Glu Glu Lys Ile Arg Ala Cys Lys Leu Ala Lys
130                 135                 140

Lys Ala Gly Ala Asp Phe Val Lys Thr Ser Thr Gly Phe Ser Thr Gly
145                 150                 155                 160

Gly Ala Lys Ala Glu Asp Ile Lys Leu Met Arg Lys Thr Val Gly Ala
                165                 170                 175

Gly Met Gly Val Lys Ala Ser Gly Gly Ile His Thr Arg Glu Glu Ala
            180                 185                 190

Ile Lys Leu Ile Glu Ala Gly Ala Thr Arg Ile Gly Ala Ser Ala Ser
        195                 200                 205

Ile Asp Ile Ile Ser Glu Asn
        210                 215
```

<210> SEQ ID NO 7
<211> LENGTH: 254
<212> TYPE: PRT
<213> ORGANISM: Unknown
<220> FEATURE:
<223> OTHER INFORMATION: Deoxyribose-phosphate aldolase from Acetobacter, species unknown.

<400> SEQUENCE: 7

```
Met Asp Thr Ile Leu Lys Glu Gln Ala Ala Arg Ala Leu Ala Leu Leu
1               5                   10                  15

Asp Leu Thr Ser Leu Asn Asp Thr Asp Thr Glu Glu Thr Val Lys Thr
            20                  25                  30

Leu Cys Ala Lys Ser His Gly Glu Phe Gly His Thr Ala Ala Val Cys
                35                  40                  45

Ile Trp Pro Arg Phe Val Lys Leu Ala Lys Glu Glu Leu Lys Gly Thr
    50                  55                  60

Pro Val Arg Val Ala Thr Val Val Asn Phe Pro His Gly Gly Thr Asp
65                  70                  75                  80

Ile Glu Ala Thr Val Ala Glu Thr Lys Gln Ala Val Ala Asp Gly Ala
                85                  90                  95

Asp Glu Ile Asp Val Val Leu Pro Tyr Lys Ala Phe Met Asp Gly Asp
                100                 105                 110

Thr Ala Ser Ala Lys Ala Leu Leu Asp Ala Thr Arg Lys Ala Cys Ala
            115                 120                 125
```

Gly Lys Thr Met Lys Val Ile Ile Glu Ser Gly Val Leu Ala His Ala
              130                 135                 140

Asn Thr Ile Ala Glu Ala Ser Arg Leu Ser Ile Ala Cys Gly Ala Asp
145                 150                 155                 160

Phe Ile Lys Thr Ser Thr Gly Lys Thr Pro Val Ser Ala Thr Leu Glu
              165                 170                 175

Ala Ala Asn Val Met Leu Glu Val Ile Arg Glu Ser Gly Lys Pro Val
              180                 185                 190

Gly Phe Lys Ala Ser Gly Gly Val Arg Ser Thr Glu Gln Ala Ala Asp
              195                 200                 205

Tyr Met Thr Leu Ala Asp Lys Ile Met Gly Pro Lys Trp Ile Ser Leu
              210                 215                 220

Met Thr Phe Arg Phe Gly Ala Ser Gly Leu Arg Asp Ser Leu Leu Ala
225                 230                 235                 240

Ser Met Gly Tyr Gly Gln Ala Pro Ala Asp Asn Lys Gly Tyr
              245                 250

<210> SEQ ID NO 8
<211> LENGTH: 237
<212> TYPE: PRT
<213> ORGANISM: Lactobacillus acidophilus
<220> FEATURE:
<223> OTHER INFORMATION: Deoxyribose-phosphate aldolase Lactobacillus
      acidophilus (strain ATCC 700396 / NCK56 / N2 / NCFM)

<400> SEQUENCE: 8

Met Lys Tyr Thr Leu Asp Asp Phe Ala Arg Leu Ile Asp His Thr Asn
1               5                   10                  15

Leu His Ala Asp Ala Thr Glu Ala Asp Met Lys Lys Leu Cys Asp Glu
              20                  25                  30

Ala Lys Lys Tyr His Phe Lys Met Val Ala Ile Asn Gln Val Gln Ser
              35                  40                  45

Lys Phe Cys Ser Glu Gln Leu Lys Gly Thr Asp Ile Asp Thr Gly Ala
50                  55                  60

Ala Ile Ala Phe Pro Leu Gly Gln Gln Thr Ile Glu Ser Lys Val Phe
65                  70                  75                  80

Asp Thr Arg Asp Ala Ile Lys Asn Gly Ala Asn Glu Ile Asp Tyr Val
              85                  90                  95

Ile Asn Ile Thr Gln Leu Lys Ala Lys Asp Tyr Asp Tyr Ile Lys Gln
              100                 105                 110

Glu Met Gln Glu Met Val Asn Ala Cys His Glu Asn His Val Pro Cys
              115                 120                 125

Lys Val Ile Phe Glu Asn Cys Tyr Leu Thr Lys Asp Glu Ile Lys Lys
              130                 135                 140

Leu Ala Glu Ile Ala Lys Glu Val Lys Pro Asp Phe Ile Lys Thr Ser
145                 150                 155                 160

Thr Gly Phe Gly Ser Ser Gly Ala Lys Val Glu Asp Val Lys Leu Met
              165                 170                 175

Lys Ser Ile Val Gly Asp Glu Val Lys Val Ala Ala Gly Gly Ile
              180                 185                 190

Arg Asn Ser Asp Asp Phe Leu Ala Met Val Arg Ala Gly Ala Asp Arg
              195                 200                 205

Ile Gly Cys Ser Ala Gly Val Lys Ile Tyr Gln Ala Leu Lys Cys Arg
              210                 215                 220

Met Lys Asp Asp His Val Asp Ser Ile Glu Ile Ala Arg

```
                    225                 230                 235

<210> SEQ ID NO 9
<211> LENGTH: 237
<212> TYPE: PRT
<213> ORGANISM: Hyperthermus butylicus
<220> FEATURE:
<223> OTHER INFORMATION: Deoxyribose-phosphate aldolase Hyperthermus
      butylicus (strain DSM 5456 / JCM 9403)

<400> SEQUENCE: 9

Met Ser Glu Ser Phe Phe Cys Arg Phe Gly Val Ser Glu Ile Ala Ser
1               5                   10                  15

Arg Ile Asp His Ala Val Leu Lys Pro Trp Ser Ser Val Ser Glu Leu
            20                  25                  30

Glu Lys Ala Ile Arg Glu Leu Glu Leu Asn Leu Arg Cys Leu Ile
        35                  40                  45

Ile Ser Pro Thr His Leu Arg Leu Ala Arg Glu Lys Thr Asn Lys Cys
50                  55                  60

Leu Gly Val Val Val Gly Phe Pro Phe Gly Tyr Ser Thr Ile Glu Ala
65                  70                  75                  80

Lys Ile Lys Glu Leu Glu Asp Ser Ile Ala Leu Gly Ala Gln Glu Ile
                85                  90                  95

Asp Tyr Val Ala Asn Thr Gln Leu Leu Leu Ala Gly Arg Thr Glu Glu
            100                 105                 110

Tyr Leu Asn Glu Ile Arg Ala Ala Ile Thr Ile Cys Arg Asp Ser Gly
        115                 120                 125

Val Lys Cys Lys Val Ile Ile Glu Ala Pro Ala Leu Pro Arg Asn Leu
130                 135                 140

Leu Val Glu Ile Val Glu Lys Ile Ala Met Met Asp Pro His Pro Asp
145                 150                 155                 160

Tyr Ile Lys Thr Ser Thr Gly Tyr Gly Pro Arg Pro Thr Tyr Val Glu
                165                 170                 175

Asp Val Tyr Leu Ile Asp Gln Thr Leu Arg Arg Ile Gly Lys Arg Asp
            180                 185                 190

Glu Ile Gly Ile Lys Ala Ala Gly Gly Ile Arg Glu Gly Leu Gln Ala
        195                 200                 205

Ala Ala Met Leu Leu Ala Gly Ala Asp Val Ile Gly Thr Ser Thr Pro
210                 215                 220

Arg Gln Val Ile Glu Thr Tyr Lys Glu Leu Cys Arg Ile
225                 230                 235

<210> SEQ ID NO 10
<211> LENGTH: 220
<212> TYPE: PRT
<213> ORGANISM: Streptococcus gordonii
<220> FEATURE:
<223> OTHER INFORMATION: Deoxyribose-phosphate aldolase Streptococcus
      gordonii (strain Challis / ATCC 35105 / CH1 / DL1 /V288)

<400> SEQUENCE: 10

Met Lys Leu Asn Lys Tyr Ile Asp His Thr Leu Leu Lys Pro Glu Ala
1               5                   10                  15

Thr Lys Glu Gln Ile Glu Lys Val Ile Glu Glu Ala Lys Glu Tyr Asp
            20                  25                  30

Phe Ala Ser Val Cys Val Asn Pro Thr Trp Val Lys Leu Ala Ala Glu
        35                  40                  45

Gly Leu Ser Gly Ser Asp Val Lys Val Cys Thr Val Ile Gly Phe Pro
```

```
                 50                  55                  60
Leu Gly Ala Thr Thr Pro Glu Val Lys Ala Phe Glu Thr Lys Asn Ala
 65                  70                  75                  80

Ile Glu Asn Gly Ala Asp Glu Ile Asp Met Val Ile Asn Ile Gly Ala
                 85                  90                  95

Leu Lys Ser Gly Asn Leu Asp Leu Leu Glu Arg Asp Ile Gln Ala Val
                100                 105                 110

Val Glu Ala Ser Gly Glu Lys Leu Val Lys Val Ile Glu Thr Cys
                115                 120                 125

Leu Leu Thr Asp Gln Glu Lys Val Leu Ala Cys Gln Val Ser Gln Lys
                130                 135                 140

Ala Gly Ala Asp Phe Val Lys Thr Ser Thr Gly Phe Ser Thr Gly Gly
145                 150                 155                 160

Ala Thr Val Glu Asp Val Ala Leu Met Arg Gln Thr Val Gly Pro Asp
                165                 170                 175

Met Gly Val Lys Ala Ser Gly Gly Ala Arg Ser Tyr Asp Asp Ala Gln
                180                 185                 190

Ala Phe Ile Lys Ala Gly Ala Thr Arg Ile Gly Ala Ser Ser Gly Val
                195                 200                 205

Ala Ile Met Lys Gly Glu Thr Ala Ser Gly Asn Tyr
                210                 215                 220

<210> SEQ ID NO 11
<211> LENGTH: 300
<212> TYPE: PRT
<213> ORGANISM: Bacteroides fragilis
<220> FEATURE:
<223> OTHER INFORMATION: Deoxyribse-phosphate aldolase Bacteroides
      fragilis

<400> SEQUENCE: 11

Met Glu Met Asn Asp Thr Pro Gln Asp Lys Tyr Leu Thr Ala Leu Ala
  1               5                  10                  15

Lys Tyr Asp Thr Gln Leu Asn Asp Ala Asp Val Gln Val Gln Val Ala
                 20                  25                  30

Ala Leu Ile Glu Lys Lys Val Pro Glu Asn Asn Thr Glu Glu Val Lys
                 35                  40                  45

Lys Phe Leu Phe Asn Cys Ile Asp Leu Thr Thr Leu Asn Thr Thr Asp
 50                  55                  60

Ser Asp Glu Ser Val Met Arg Phe Thr Glu Lys Val Asn Arg Phe Asp
 65                  70                  75                  80

Asp Glu Phe Pro Asp Leu Lys Asn Val Ala Ala Ile Cys Val Tyr Pro
                 85                  90                  95

Asn Phe Ala Gln Val Val Lys Asp Thr Leu Glu Val Glu Gly Ile Asn
                100                 105                 110

Ile Ala Cys Val Ser Gly Gly Phe Pro Ser Ser Gln Thr Phe Thr Glu
                115                 120                 125

Val Lys Ile Ala Glu Thr Ala Met Ala Leu Ala Asp Gly Ala Asp Glu
                130                 135                 140

Ile Asp Ile Val Ile Pro Val Gly Ala Phe Leu Ser Gly Asp Tyr Glu
145                 150                 155                 160

Thr Met Cys Glu Glu Ile Met Glu Leu Lys Glu Thr Cys Lys Glu His
                165                 170                 175

His Leu Lys Val Ile Leu Glu Thr Gly Ala Leu Lys Thr Ala Ser Asn
                180                 185                 190
```

```
Ile Lys Lys Ala Ser Ile Leu Ser Met Tyr Ser Gly Ala Asp Phe Ile
            195                 200                 205

Lys Thr Ser Thr Gly Lys Gln Gln Pro Ala Ala Thr Pro Glu Ala Ala
    210                 215                 220

Tyr Val Met Cys Gln Ala Ile Lys Glu Tyr Tyr Glu Gln Thr Gly Asn
225                 230                 235                 240

Lys Val Gly Phe Lys Pro Ala Gly Gly Ile Asn Thr Val Asn Asp Ala
                245                 250                 255

Leu Ile Tyr Tyr Thr Ile Val Lys Glu Val Leu Gly Lys Glu Trp Leu
            260                 265                 270

Ser Asn Glu Leu Phe Arg Leu Gly Thr Ser Arg Leu Ala Asn Leu Leu
    275                 280                 285

Leu Ser Glu Ile Lys Gly Glu Glu Leu Lys Phe Phe
    290                 295                 300

<210> SEQ ID NO 12
<211> LENGTH: 220
<212> TYPE: PRT
<213> ORGANISM: Staphylococcus aureus
<220> FEATURE:
<223> OTHER INFORMATION: Deoxyribose-phosphate aldolase Staphylococcus
      aureus (strain bovine RF122 / ET3-1)

<400> SEQUENCE: 12

Met Lys Phe Glu Lys Tyr Ile Asp His Thr Leu Leu Lys Pro Glu Ser
1               5                   10                  15

Thr Arg Thr Gln Ile Asp Gln Ile Ile Asp Glu Ala Lys Ala Tyr Asn
            20                  25                  30

Phe Lys Ser Val Cys Val Asn Pro Thr His Val Lys Tyr Ala Ala Glu
        35                  40                  45

Arg Leu Ala Asp Ser Glu Val Leu Val Cys Thr Val Ile Gly Phe Pro
    50                  55                  60

Leu Gly Ala Ser Thr Thr Ala Thr Lys Ala Phe Glu Thr Glu Asp Ala
65                  70                  75                  80

Ile Gln Asn Gly Ala Asp Glu Ile Asp Met Val Ile Asn Ile Gly Ala
                85                  90                  95

Leu Lys Asp Gly Arg Phe Asp Val Gln Gln Asp Ile Glu Ala Val
            100                 105                 110

Val Lys Ala Ala Lys Gly His Thr Val Lys Val Ile Ile Glu Thr Ile
        115                 120                 125

Leu Leu Asp His Asp Glu Ile Val Lys Ala Ser Glu Leu Thr Lys Ala
    130                 135                 140

Ala Gly Ala Asp Phe Val Lys Thr Ser Thr Gly Phe Ala Gly Gly Gly
145                 150                 155                 160

Ala Thr Ala Glu Asp Val Lys Leu Met Lys Asp Thr Val Gly Ala Asp
                165                 170                 175

Val Glu Val Lys Ala Ser Gly Gly Val Arg Asn Leu Glu Asp Phe Asn
            180                 185                 190

Lys Met Val Glu Ala Gly Ala Thr Arg Ile Gly Ala Ser Ala Gly Val
        195                 200                 205

Gln Ile Met Gln Gly Leu Glu Ala Asp Ser Asp Tyr
    210                 215                 220

<210> SEQ ID NO 13
<211> LENGTH: 180
<212> TYPE: PRT
<213> ORGANISM: Acetobacterium woodii
```

<220> FEATURE:
<223> OTHER INFORMATION: Deoxyribose-phosphate aldolase Acetobacterium
      woodii (strain ATCC 29683 / DSM 1030 / JCM 2381 / KCTC 1655)

<400> SEQUENCE: 13

Met Leu Lys Gly Thr Asp Val Lys Ala Cys Val Val Ile Asp Tyr Pro
1               5                   10                  15

Phe Gly Thr Gly Ser Ile Glu Asp Lys Val Asn Gln Ala Lys Val Ala
            20                  25                  30

Ile Glu His Gly Val Glu Ile Asp Phe Val Ile Asp Tyr Gly His
        35                  40                  45

Leu Lys Ser Gly Asn Lys Asp His Leu Leu Lys Glu Ile Lys Ala Cys
50                  55                  60

Val Ala Ala Asn Gly Arg Glu Thr Arg Phe Ile Ile Glu Val Cys
65                  70                  75                  80

Tyr Leu Thr Pro Glu Glu Ile Val Thr Ala Cys Glu Cys Val Ile Asp
                85                  90                  95

Gly Gly Gly Asp Phe Val Lys Thr Ser Thr Gly Arg Phe Gly Gly Pro
            100                 105                 110

Asp Met Glu Ile Ile Asp Leu Leu Val Lys Thr Cys Lys Gly Arg Cys
        115                 120                 125

Lys Leu Lys Val Ala Gly Thr Gly Gln Phe Trp Thr Ala Asn Ile Ala
130                 135                 140

Leu Met Cys Ile Ala Ala Gly Val Asp Ile Ile Gly Thr Arg Ser Ala
145                 150                 155                 160

Lys Lys Ile Val Asp Ala Leu Glu Ile Phe Glu Arg Phe Ala Lys Gly
                165                 170                 175

Ile Glu Val Lys
            180

<210> SEQ ID NO 14
<211> LENGTH: 265
<212> TYPE: PRT
<213> ORGANISM: Aspergillus fumigatus
<220> FEATURE:
<223> OTHER INFORMATION: Deoxyribose-phosphate aldolase Neosartorya
      fumigata (strain ATCC MYA-4609 / Af293 / CBS 101355 / FGSC A1100)

<400> SEQUENCE: 14

Met Thr Leu Pro Thr Asn Asn Ala Glu Trp Gly Ala Val Ile Ser Ser
1               5                   10                  15

Tyr Lys Asp Gln Leu Pro Glu Val Tyr Pro Val Tyr Gln Thr Pro Leu
            20                  25                  30

Pro Ser Ser Val Asn Arg Tyr Ile Asp His Thr Gln Leu Ser Leu Asp
        35                  40                  45

Ala Thr Asp Glu Asp Ile Asp Lys Leu Cys Ala Glu Ala Ala Lys His
    50                  55                  60

Asn Phe Ser Ala Val Cys Val Arg Leu Arg His Val Arg Arg Ala Val
65                  70                  75                  80

Thr Asn Leu Gln Gly Ser Pro Glu Cys Thr Val Ala Cys Val Val Gly
                85                  90                  95

Phe Pro Glu Gly Thr His Asp Thr Met Glu Lys Glu Lys Glu Ala Leu
            100                 105                 110

Asp Ala Ala Glu Leu Gly Ala Ser Glu Leu Asp Met Val Ile Asn Trp
        115                 120                 125

Pro Lys Leu Lys Glu Gly Gln Tyr Met Asp Val Tyr Thr Asp Val Leu
    130                 135                 140

```
Glu Val Arg Lys Gly Ala Pro Ser Pro Val Lys Leu Lys Val Ile Leu
145                 150                 155                 160

Glu Thr Ser Gln Leu Thr Lys Asp Glu Ile Ile Ala Gly Ser Val Ile
                165                 170                 175

Ser Ser Met Ala Gly Ala Asp Phe Val Lys Thr Ser Thr Gly Phe Lys
            180                 185                 190

Gly Ala Gly Ala Asn Val Asp Asp Val Ala Met Met Arg Ala Ile Val
            195                 200                 205

Glu Leu Val Gly Arg Gly Thr Lys Val Lys Ala Ser Gly Gly Val Arg
210                 215                 220

Ser Ala Glu Asp Cys Ile Lys Met Leu Lys Ala Gly Ala Asp Arg Ile
225                 230                 235                 240

Gly Thr Ser Ser Gly Val Asn Ile Ile Asn Gln Leu Ala Gly Lys Glu
                245                 250                 255

Thr Gln Pro Thr Thr Pro Ala Ala Tyr
            260                 265

<210> SEQ ID NO 15
<211> LENGTH: 256
<212> TYPE: PRT
<213> ORGANISM: Shewanella oneidensis
<220> FEATURE:
<223> OTHER INFORMATION: Deoxyribose-phosphate aldolase Shewanella
      oneidensis (strain MR-1)

<400> SEQUENCE: 15

Met Thr Asp Leu Lys Lys Ala Ala Gln Arg Ala Ile Glu Leu Met Asp
1               5                   10                  15

Leu Thr Thr Leu Asn Asp Asp Thr Asp Gln Lys Val Ile Asp Leu
            20                  25                  30

Cys His Lys Ala Val Thr Pro Ala Gly Asn Thr Ala Ala Ile Cys Ile
                35                  40                  45

Tyr Pro Arg Phe Ile Pro Ile Ala Arg Lys Thr Leu Asp Glu Leu Gly
50                  55                  60

Ala Glu Asp Ile Gln Ile Ala Thr Val Thr Asn Phe Pro His Gly Asn
65                  70                  75                  80

Asp Asp Ile Ala Ile Ala Val Leu Glu Thr Arg Ala Ala Val Ala Tyr
                85                  90                  95

Gly Ala Asp Glu Val Asp Val Val Phe Pro Tyr Arg Ala Leu Met Glu
            100                 105                 110

Gly Asn Glu Thr Val Gly Tyr Glu Leu Val Lys Ala Cys Lys Glu Ala
            115                 120                 125

Cys Gly Glu Val Leu Leu Lys Val Ile Ile Glu Ser Gly Val Leu Ala
        130                 135                 140

Asp Pro Val Leu Ile Arg Arg Ala Ser Glu Leu Ser Ile Glu Ala Gly
145                 150                 155                 160

Ala Asp Phe Ile Lys Thr Ser Thr Gly Lys Val Pro Val Asn Ala Thr
                165                 170                 175

Leu Glu Ala Ala Glu Ile Met Leu Thr Val Ile Ser Glu Lys Asn Thr
            180                 185                 190

Lys Val Gly Phe Lys Pro Ala Gly Gly Val Arg Asp Ala Ala Gln Ala
        195                 200                 205

Ala Glu Phe Leu Gly Val Ala Glu Arg Ile Leu Gly Ala Asp Trp Val
210                 215                 220

Ser Pro Arg Thr Phe Arg Phe Gly Ala Ser Ser Leu Leu Asn Ser Leu
```

```
                225                 230                 235                 240
Leu His Thr Leu Glu Leu Ala Asp Ala Pro Lys Arg Thr Gln Gly Tyr
            245                 250                 255

<210> SEQ ID NO 16
<211> LENGTH: 440
<212> TYPE: PRT
<213> ORGANISM: Escherichia coli
<220> FEATURE:
<223> OTHER INFORMATION: Xylose isomerase Escherichia coli (strain K12)

<400> SEQUENCE: 16

Met Gln Ala Tyr Phe Asp Gln Leu Asp Arg Val Arg Tyr Glu Gly Ser
1               5                   10                  15

Lys Ser Ser Asn Pro Leu Ala Phe Arg His Tyr Asn Pro Asp Glu Leu
            20                  25                  30

Val Leu Gly Lys Arg Met Glu Glu His Leu Arg Phe Ala Ala Cys Tyr
        35                  40                  45

Trp His Thr Phe Cys Trp Asn Gly Ala Asp Met Phe Gly Val Gly Ala
    50                  55                  60

Phe Asn Arg Pro Trp Gln Gln Pro Gly Glu Ala Leu Ala Leu Ala Lys
65                  70                  75                  80

Arg Lys Ala Asp Val Ala Phe Glu Phe Phe His Lys Leu His Val Pro
                85                  90                  95

Phe Tyr Cys Phe His Asp Val Asp Val Ser Pro Glu Gly Ala Ser Leu
            100                 105                 110

Lys Glu Tyr Ile Asn Asn Phe Ala Gln Met Val Asp Val Leu Ala Gly
        115                 120                 125

Lys Gln Glu Glu Ser Gly Val Lys Leu Leu Trp Gly Thr Ala Asn Cys
    130                 135                 140

Phe Thr Asn Pro Arg Tyr Gly Ala Gly Ala Ala Thr Asn Pro Asp Pro
145                 150                 155                 160

Glu Val Phe Ser Trp Ala Ala Thr Gln Val Val Thr Ala Met Glu Ala
                165                 170                 175

Thr His Lys Leu Gly Gly Glu Asn Tyr Val Leu Trp Gly Gly Arg Glu
            180                 185                 190

Gly Tyr Glu Thr Leu Leu Asn Thr Asp Leu Arg Gln Glu Arg Glu Gln
        195                 200                 205

Leu Gly Arg Phe Met Gln Met Val Val Glu His Lys His Lys Ile Gly
    210                 215                 220

Phe Gln Gly Thr Leu Leu Ile Glu Pro Lys Pro Gln Glu Pro Thr Lys
225                 230                 235                 240

His Gln Tyr Asp Tyr Asp Ala Ala Thr Val Tyr Gly Phe Leu Lys Gln
                245                 250                 255

Phe Gly Leu Glu Lys Glu Ile Lys Leu Asn Ile Glu Ala Asn His Ala
            260                 265                 270

Thr Leu Ala Gly His Ser Phe His His Glu Ile Ala Thr Ala Ile Ala
        275                 280                 285

Leu Gly Leu Phe Gly Ser Val Asp Ala Asn Arg Gly Asp Ala Gln Leu
    290                 295                 300

Gly Trp Asp Thr Asp Gln Phe Pro Asn Ser Val Glu Glu Asn Ala Leu
305                 310                 315                 320

Val Met Tyr Glu Ile Leu Lys Ala Gly Gly Phe Thr Thr Gly Gly Leu
                325                 330                 335

Asn Phe Asp Ala Lys Val Arg Arg Gln Ser Thr Asp Lys Tyr Asp Leu
```

```
                340             345                 350
Phe Tyr Gly His Ile Gly Ala Met Asp Thr Met Ala Leu Ala Leu Lys
        355                 360                 365

Ile Ala Ala Arg Met Ile Glu Asp Gly Glu Leu Asp Lys Arg Ile Ala
370                 375                 380

Gln Arg Tyr Ser Gly Trp Asn Ser Glu Leu Gly Gln Gln Ile Leu Lys
385                 390                 395                 400

Gly Gln Met Ser Leu Ala Asp Leu Ala Lys Tyr Ala Gln Glu His His
                405                 410                 415

Leu Ser Pro Val His Gln Ser Gly Arg Gln Glu Gln Leu Glu Asn Leu
            420                 425                 430

Val Asn His Tyr Leu Phe Asp Lys
            435                 440

<210> SEQ ID NO 17
<211> LENGTH: 448
<212> TYPE: PRT
<213> ORGANISM: Bacillus licheniformis
<220> FEATURE:
<223> OTHER INFORMATION: Xylose isomerase Bacillus licheniformis (strain
      DSM 13 / ATCC 14580)

<400> SEQUENCE: 17

Met Phe Phe Arg Asn Ile Gly Met Ile Glu Tyr Glu Gly Ala Asp Ser
1               5                   10                  15

Glu Asn Pro Tyr Ala Phe Lys Tyr Tyr Asn Pro Asp Glu Phe Val Gly
            20                  25                  30

Gly Lys Thr Met Lys Glu His Leu Arg Phe Ala Val Ala Tyr Trp His
        35                  40                  45

Thr Phe Asp Ala Asp Gly Lys Asp Pro Phe Gly Asp Gly Thr Met Phe
    50                  55                  60

Arg Ala Trp Asn Arg Leu Thr His Pro Leu Asp Lys Ala Lys Ala Arg
65                  70                  75                  80

Ala Glu Ala Ala Phe Glu Phe Glu Lys Leu Gly Val Pro Tyr Phe
                85                  90                  95

Cys Phe His Asp Val Asp Ile Val Asp Glu Gly Ala Thr Leu Arg Glu
            100                 105                 110

Thr Phe Thr Tyr Leu Asp Gln Met Ser Ser Phe Leu Lys Glu Met Met
        115                 120                 125

Glu Thr Ser His Val Gln Leu Leu Trp Asn Thr Ala Asn Met Phe Thr
130                 135                 140

His Pro Arg Tyr Val His Gly Ala Ala Thr Ser Cys Asn Ala Asp Val
145                 150                 155                 160

Tyr Ala Tyr Ala Ala Lys Val Lys Lys Gly Leu Asp Ile Ala Lys
                165                 170                 175

Glu Leu Gly Ala Glu Asn Tyr Val Phe Trp Gly Gly Arg Glu Gly Tyr
            180                 185                 190

Glu Thr Leu Leu Asn Thr Asp Met Lys Leu Glu Leu Glu Asn Leu Ser
        195                 200                 205

Ser Phe Tyr Arg Met Ala Val Glu Tyr Ala Arg Glu Ile Gly Phe Asp
    210                 215                 220

Gly Gln Phe Leu Ile Glu Pro Lys Pro Lys Glu Pro Thr Lys His Gln
225                 230                 235                 240

Tyr Asp Phe Asp Ala Ala Thr Thr Ile Ala Phe Leu Glu Thr Tyr Gly
                245                 250                 255
```

```
Leu Lys Asp His Phe Lys Leu Asn Leu Glu Ala Asn His Ala Thr Leu
            260                 265                 270

Ala Gly His Thr Phe Glu His Glu Leu Arg Val Ala Ala Leu His Asp
        275                 280                 285

Met Leu Gly Ser Ile Asp Ala Asn Gln Gly Asp Leu Leu Leu Gly Trp
    290                 295                 300

Asp Thr Asp Glu Phe Pro Thr Asp Leu Tyr Ser Ala Val Leu Ala Met
305                 310                 315                 320

Tyr Glu Ile Leu Lys Ala Gly Phe Lys Thr Gly Ile Asn Phe
                325                 330                 335

Asp Ala Lys Val Arg Arg Pro Ser Phe Ala Asp Glu Asp Leu Phe His
                340                 345                 350

Ala His Ile Ala Gly Met Asp Thr Tyr Ala Val Gly Leu Lys Val Ala
            355                 360                 365

Ser Arg Leu Leu Glu Asp Lys Ala Leu Asp Gln Val Ile Glu Glu Arg
        370                 375                 380

Tyr Glu Ser Tyr Thr Lys Gly Ile Gly Leu Glu Ile Lys Glu Gly Arg
385                 390                 395                 400

Thr Asp Leu Lys Lys Leu Ala Ala Tyr Ala Leu Glu Asn Asp His Ile
                405                 410                 415

Glu Asn Gln Ser Gly Arg Gln Glu Arg Leu Lys Ala Thr Val Asn Arg
            420                 425                 430

Tyr Leu Leu Asn Ala Leu Arg Glu Ala Pro Ala Gly Lys Glu Thr His
        435                 440                 445

<210> SEQ ID NO 18
<211> LENGTH: 387
<212> TYPE: PRT
<213> ORGANISM: Streptomyces olivochromogenes
<220> FEATURE:
<223> OTHER INFORMATION: Xylose isomerase Streptomyces olivochromogenes

<400> SEQUENCE: 18

Met Ser Tyr Gln Pro Thr Pro Glu Asp Arg Phe Thr Phe Gly Leu Trp
1               5                   10                  15

Thr Val Gly Trp Gln Gly Arg Asp Pro Phe Gly Asp Ala Thr Arg Pro
            20                  25                  30

Ala Leu Asp Pro Val Glu Thr Val Gln Arg Leu Ala Glu Leu Gly Ala
        35                  40                  45

His Gly Val Thr Phe His Asp Asp Leu Ile Pro Phe Gly Ser Ser
    50                  55                  60

Asp Thr Glu Arg Glu Ser His Ile Lys Arg Phe Arg Gln Ala Leu Asp
65                  70                  75                  80

Ala Thr Gly Met Thr Val Pro Met Ala Thr Thr Asn Leu Phe Thr His
                85                  90                  95

Pro Val Phe Lys Asp Gly Gly Phe Thr Ala Asn Asp Arg Asp Val Arg
            100                 105                 110

Arg Tyr Ala Leu Arg Lys Thr Ile Arg Asn Ile Asp Leu Ala Val Glu
        115                 120                 125

Leu Gly Ala Lys Thr Tyr Val Ala Trp Gly Gly Arg Glu Gly Ala Glu
    130                 135                 140

Ser Gly Ala Ala Lys Asp Val Arg Val Ala Leu Asp Arg Met Lys Glu
145                 150                 155                 160

Ala Phe Asp Leu Leu Gly Glu Tyr Val Thr Ser Gln Gly Tyr Asp Thr
                165                 170                 175
```

```
Arg Phe Ala Ile Glu Pro Lys Pro Asn Glu Pro Arg Gly Asp Ile Leu
            180                 185                 190

Leu Pro Thr Val Gly His Ala Leu Ala Phe Ile Glu Arg Leu Glu Arg
        195                 200                 205

Pro Glu Leu Tyr Gly Val Asn Pro Glu Val Gly His Glu Gln Met Ala
    210                 215                 220

Gly Leu Asn Phe Pro His Gly Ile Ala Gln Ala Leu Trp Ala Gly Lys
225                 230                 235                 240

Leu Phe His Ile Asp Leu Asn Gly Gln Ser Gly Ile Lys Tyr Asp Gln
                245                 250                 255

Asp Leu Arg Phe Gly Ala Gly Asp Leu Arg Ala Ala Phe Trp Leu Val
            260                 265                 270

Asp Leu Leu Glu Ser Ala Gly Tyr Glu Gly Pro Arg His Phe Asp Phe
        275                 280                 285

Lys Pro Pro Arg Thr Glu Asp Ile Asp Gly Val Trp Ala Ser Ala Ala
    290                 295                 300

Gly Cys Met Arg Asn Tyr Leu Ile Leu Lys Glu Arg Ala Ala Ala Phe
305                 310                 315                 320

Arg Ala Asp Pro Glu Val Gln Glu Ala Leu Arg Ala Ser Arg Leu Asp
                325                 330                 335

Glu Leu Ala Gln Pro Thr Ala Ala Asp Gly Val Gln Glu Leu Leu Ala
            340                 345                 350

Asp Arg Thr Ala Phe Glu Asp Phe Asp Val Asp Ala Ala Ala Ala Arg
        355                 360                 365

Gly Met Ala Phe Glu Arg Leu Asp Gln Leu Ala Met Asp His Leu Leu
    370                 375                 380

Gly Ala Arg
385

<210> SEQ ID NO 19
<211> LENGTH: 387
<212> TYPE: PRT
<213> ORGANISM: Thermus thermophilus
<220> FEATURE:
<223> OTHER INFORMATION: Xylose isomerase Thermus thermophilus (strain
      HB8 / ATCC 27634 / DSM 579)

<400> SEQUENCE: 19

Met Tyr Glu Pro Lys Pro Glu His Arg Phe Thr Phe Gly Leu Trp Thr
1               5                   10                  15

Val Gly Asn Val Gly Arg Asp Pro Phe Gly Asp Ala Val Arg Glu Arg
            20                  25                  30

Leu Asp Pro Val Tyr Val Val His Lys Leu Ala Glu Leu Gly Ala Tyr
        35                  40                  45

Gly Val Asn Leu His Asp Glu Asp Leu Ile Pro Arg Gly Thr Pro Pro
    50                  55                  60

Gln Glu Arg Asp Gln Ile Val Arg Arg Phe Lys Lys Ala Leu Asp Glu
65                  70                  75                  80

Thr Gly Leu Lys Val Pro Met Val Thr Ala Asn Leu Phe Ser Asp Pro
                85                  90                  95

Ala Phe Lys Asp Gly Ala Phe Thr Ser Pro Asp Pro Trp Val Arg Ala
            100                 105                 110

Tyr Ala Leu Arg Lys Ser Leu Glu Thr Met Asp Leu Gly Ala Glu Leu
        115                 120                 125

Gly Ala Glu Ile Tyr Val Val Trp Pro Gly Arg Glu Gly Ala Glu Val
    130                 135                 140
```

```
Glu Ala Thr Gly Lys Ala Arg Lys Val Trp Asp Trp Val Arg Glu Ala
145                 150                 155                 160

Leu Asn Phe Met Ala Ala Tyr Ala Glu Asp Gln Gly Tyr Gly Tyr Arg
                165                 170                 175

Phe Ala Leu Glu Pro Lys Pro Asn Glu Pro Arg Gly Asp Ile Tyr Phe
            180                 185                 190

Ala Thr Val Gly Ser Met Leu Ala Phe Ile His Thr Leu Asp Arg Pro
        195                 200                 205

Glu Arg Phe Gly Leu Asn Pro Glu Phe Ala His Glu Thr Met Ala Gly
    210                 215                 220

Leu Asn Phe Val His Ala Val Ala Gln Ala Leu Asp Ala Gly Lys Leu
225                 230                 235                 240

Phe His Ile Asp Leu Asn Asp Gln Arg Met Ser Arg Phe Asp Gln Asp
                245                 250                 255

Leu Arg Phe Gly Ser Glu Asn Leu Lys Ala Ala Phe Phe Leu Val Asp
                260                 265                 270

Leu Leu Glu Ser Ser Gly Tyr Gln Gly Pro Arg His Phe Asp Ala His
            275                 280                 285

Ala Leu Arg Thr Glu Asp Glu Glu Gly Val Trp Ala Phe Ala Arg Gly
        290                 295                 300

Cys Met Arg Thr Tyr Leu Ile Leu Lys Glu Arg Ala Glu Ala Phe Arg
305                 310                 315                 320

Glu Asp Pro Glu Val Lys Glu Leu Leu Ala Ala Tyr Tyr Gln Glu Asp
                325                 330                 335

Pro Ala Ala Leu Ala Leu Gly Pro Tyr Ser Arg Glu Lys Ala Glu
                340                 345                 350

Ala Leu Lys Arg Ala Glu Leu Pro Leu Glu Ala Lys Arg Arg Gly
            355                 360                 365

Tyr Ala Leu Glu Arg Leu Asp Gln Leu Ala Val Glu Tyr Leu Leu Gly
        370                 375                 380

Val Arg Gly
385

<210> SEQ ID NO 20
<211> LENGTH: 444
<212> TYPE: PRT
<213> ORGANISM: Candida boidinii
<220> FEATURE:
<223> OTHER INFORMATION: Xylose isomerase Candida boidinii

<400> SEQUENCE: 20

Met Glu Leu Ile Met Pro Ala Tyr Phe Asp Gln Leu Asp Arg Val Arg
1               5                   10                  15

Phe Glu Gly Thr Gln Ser Thr Asn Pro Leu Ala Phe Arg His Tyr Asn
                20                  25                  30

Pro Asp Glu Ile Val Leu Gly Lys Arg Met Glu Asp His Leu Arg Phe
            35                  40                  45

Ala Ala Cys Tyr Trp His Thr Phe Cys Trp Asn Gly Ala Asp Met Phe
        50                  55                  60

Gly Met Gly Ala Phe Asp Arg Pro Trp Gln Gln Pro Gly Glu Ala Leu
65                  70                  75                  80

Ala Leu Ala Lys Arg Lys Ala Asp Val Ala Phe Glu Phe Phe His Lys
                85                  90                  95

Leu Asn Val Pro Tyr Tyr Cys Phe His Asp Val Asp Val Ser Pro Glu
                100                 105                 110
```

```
Gly Ala Ser Leu Lys Glu Tyr Lys Asn Asn Phe Ala Gln Met Val Asp
            115                 120                 125

Val Leu Ala Ala Lys Gln Glu Gln Ser Gly Val Lys Leu Leu Trp Gly
130                 135                 140

Thr Ala Asn Cys Phe Thr Asn Pro Arg Tyr Gly Ala Gly Ala Ala Thr
145                 150                 155                 160

Asn Pro Asp Pro Glu Val Phe Ser Trp Ala Ala Thr Gln Val Val Thr
                165                 170                 175

Ala Met Asp Ala Thr His Lys Leu Gly Gly Glu Asn Tyr Val Leu Trp
            180                 185                 190

Gly Gly Arg Glu Gly Tyr Glu Thr Leu Leu Asn Thr Asp Leu Arg Gln
        195                 200                 205

Glu Arg Glu Gln Ile Gly Arg Phe Met Gln Leu Val Val Glu His Lys
210                 215                 220

His Lys Ile Gly Phe Gln Gly Thr Leu Leu Ile Glu Pro Lys Pro Gln
225                 230                 235                 240

Glu Pro Thr Lys His Gln Tyr Asp Tyr Asp Ala Ala Thr Val Tyr Gly
                245                 250                 255

Phe Leu Lys Gln Phe Gly Leu Glu Lys Glu Ile Lys Leu Asn Ile Glu
            260                 265                 270

Ala Asn Tyr Ala Thr Leu Ala Gly His Ser Phe His His Gly Ile Ala
        275                 280                 285

Thr Ala Ile Ala Leu Gly Leu Phe Gly Ser Val Asp Ala Asn Arg Gly
290                 295                 300

Asp Ala Gln Leu Gly Trp Asp Thr Asp Gln Phe Pro Asn Ser Val Glu
305                 310                 315                 320

Glu Asn Ala Leu Val Met Tyr Glu Ile Leu Lys Ala Gly Gly Phe Thr
                325                 330                 335

Thr Gly Gly Leu Asn Phe Asp Ala Lys Val Arg Arg Gln Ser Thr Asp
            340                 345                 350

Lys Tyr Asp Leu Phe Tyr Gly His Ile Gly Ala Met Asp Thr Met Ala
        355                 360                 365

Leu Ser Leu Lys Ile Ala Ala Arg Met Ile Glu Ala Gly Gly Leu Asp
370                 375                 380

Gln Arg Val Ala Lys Arg Tyr Ala Gly Trp Asn Gly Glu Leu Gly Gln
385                 390                 395                 400

Gln Ile Leu Lys Gly Gln Met Thr Leu Thr Glu Ile Ala Gln Tyr Ala
                405                 410                 415

Glu Gln His Asn Leu Ala Pro Val His Gln Ser Gly His Gln Glu Leu
            420                 425                 430

Leu Glu Asn Leu Val Asn His Tyr Leu Phe Asp Lys
        435                 440

<210> SEQ ID NO 21
<211> LENGTH: 598
<212> TYPE: PRT
<213> ORGANISM: Castellaniella defragrans

<400> SEQUENCE: 21

Met Ala Asn Asp Thr Arg Gln Val Val Gln Gly Val Gln Glu Met Thr
1               5                   10                  15

Pro Ser Glu Ala Phe Val Glu Thr Met Val Ala Asn Gly Val Thr Glu
            20                  25                  30

Ile Phe Gly Ile Met Gly Ser Ala Phe Met Asp Ala Met Asp Ile Phe
```

```
            35                  40                  45
Ala Pro Ala Gly Ile Lys Leu Ile Pro Val His Glu Gln Gly Ala
 50                  55                  60
Ala His Met Ala Asp Gly Phe Ala Arg Val Ser Gly Arg Thr Gly Val
 65                  70                  75                  80
Val Ile Gly Gln Asn Gly Pro Gly Ile Ser Asn Cys Val Thr Ala Ile
                     85                  90                  95
Ala Ala Ala Tyr Trp Ala His Thr Pro Val Val Ile Val Thr Pro Glu
                100                 105                 110
Ala Gly Thr Thr Gly Ile Gly Leu Gly Gly Phe Gln Glu Ala Arg Gln
                115                 120                 125
Leu Pro Met Phe Gln Glu Phe Thr Lys Tyr Gln Gly His Val Thr His
130                 135                 140
Pro Ala Arg Met Ala Glu Tyr Thr Ala Arg Cys Phe Ala Arg Ala Arg
145                 150                 155                 160
Asp Glu Met Gly Pro Ala Gln Leu Asn Ile Pro Arg Asp Tyr Phe Tyr
                165                 170                 175
Gly Lys Ile Lys Cys Glu Ile Pro Leu Pro Gln Pro Leu Asp Arg Gly
                180                 185                 190
Pro Gly Gly Ala Gln Ser Leu Asp Ala Ala Ala Arg Leu Leu Ala Glu
                195                 200                 205
Ala Lys Phe Pro Val Ile Ile Ser Gly Gly Val Val Met Gly Asp
210                 215                 220
Ala Val Glu Glu Cys Lys Ala Leu Ala Glu Arg Leu Gly Ala Pro Val
225                 230                 235                 240
Val Asn Ser Tyr Leu His Asn Asp Ser Phe Pro Ala Ser His Pro Leu
                245                 250                 255
Trp Cys Gly Pro Leu Gly Tyr Gln Gly Ser Lys Ala Ala Met Lys Leu
                260                 265                 270
Leu Ala Asp Ala Asp Val Val Leu Ala Leu Gly Thr Arg Leu Gly Pro
                275                 280                 285
Phe Gly Thr Leu Pro Gln His Gly Leu Asp Tyr Trp Pro Lys Asn Ala
290                 295                 300
Arg Ile Ile Gln Val Asp Ala Asp Ser Lys Met Leu Gly Leu Val Lys
305                 310                 315                 320
Lys Ile Thr Val Gly Val Cys Gly Asp Ala Lys Ala Ser Ala Ala Glu
                325                 330                 335
Ile Ser Arg Arg Ile Asp Gly Met Lys Leu Ala Cys Asp Ala Asn Lys
                340                 345                 350
Ala Glu Arg Ala Ala Arg Ile Gln Ala Glu Lys Asp Ala Trp Glu Gln
                355                 360                 365
Glu Leu Thr Asp Trp Thr His Glu Arg Asp Pro Phe Ser Leu Asp Met
                370                 375                 380
Ile Glu Glu Gln Ser Lys Glu Glu Gly Asn Trp Leu His Pro Arg Gln
385                 390                 395                 400
Val Leu Arg Glu Leu Glu Lys Ala Met Pro Glu Asp Val Met Val Ser
                405                 410                 415
Thr Asp Ile Gly Asn Ile Asn Ser Val Ala Asn Ser Tyr Leu Arg Phe
                420                 425                 430
Glu Lys Pro Arg Ser Phe Phe Ala Ala Met Ser Trp Gly Asn Cys Gly
                435                 440                 445
Tyr Ala Phe Pro Thr Ile Ile Gly Ala Lys Val Ala Ala Pro His Arg
                450                 455                 460
```

-continued

Pro Ala Val Ser Tyr Ala Gly Asp Gly Ala Trp Gly Met Ser Met Ser
465                 470                 475                 480

Glu Ile Met Thr Cys Val Arg His Asp Ile Pro Val Thr Ala Val Val
                485                 490                 495

Phe His Asn Arg Gln Trp Gly Ala Glu Lys Lys Asn Gln Val Asp Phe
            500                 505                 510

Tyr Asn Arg Arg Phe Val Ala Gly Glu Leu Glu Ser Glu Ser Phe Ala
        515                 520                 525

Gly Ile Ala Arg Ala Met Gly Ala Glu Gly Val Val Val Asp Arg Ile
530                 535                 540

Glu Asp Val Gly Pro Ala Leu Lys Lys Ala Ile Asp Ala Gln Met Asn
545                 550                 555                 560

Asp Arg Lys Thr Thr Val Ile Glu Ile Met Cys Thr Arg Glu Leu Gly
                565                 570                 575

Asp Pro Phe Arg Arg Asp Ala Leu Ser Lys Pro Val Arg Leu Leu Glu
            580                 585                 590

Lys Tyr Arg Asp Tyr Thr
            595

<210> SEQ ID NO 22
<211> LENGTH: 603
<212> TYPE: PRT
<213> ORGANISM: Achromobacter xylosoxidans

<400> SEQUENCE: 22

Met Ala Ala Thr Asp Asn Arg Lys Val Val Glu Gly Val His Lys Met
1               5                   10                  15

Thr Pro Ser Glu Ala Phe Val Glu Thr Cys Val Ala Asn Gly Val Ser
            20                  25                  30

Glu Met Phe Gly Ile Met Gly Ser Ala Phe Met Asp Ala Met Asp Ile
        35                  40                  45

Phe Ala Pro Ala Gly Ile Arg Leu Ile Pro Val Val His Glu Gln Gly
    50                  55                  60

Ala Ala His Met Ala Asp Gly Tyr Ala Arg Val Ser Gly Arg His Gly
65                  70                  75                  80

Val Val Ile Gly Gln Asn Gly Pro Gly Ile Ser Asn Cys Val Thr Gly
                85                  90                  95

Ile Ala Ala Ala Tyr Trp Ala His Ser Pro Val Val Ile Val Thr Pro
            100                 105                 110

Glu Thr Gly Thr Met Gly Met Gly Leu Gly Gly Phe Gln Glu Ala Asn
        115                 120                 125

Gln Leu Pro Met Phe Gln Glu Phe Thr Lys Tyr Gln Gly His Val Cys
    130                 135                 140

Asn Pro Lys Arg Met Ala Glu Phe Thr Gly Arg Val Phe Asp Arg Ala
145                 150                 155                 160

Met Ser Glu Met Gly Pro Thr Gln Leu Asn Ile Pro Arg Asp Tyr Phe
                165                 170                 175

Tyr Gly Glu Ile Glu Cys Glu Ile Pro Lys Pro Met Arg Val Asp Arg
            180                 185                 190

Gly His Gly Gly Glu Ala Ser Leu Gln Ala Ala Val Glu Leu Leu Lys
        195                 200                 205

Thr Ala Lys Phe Pro Val Ile Leu Ala Gly Gly Gly Val Val Met Gly
    210                 215                 220

Asp Ala Val Glu Glu Ala Lys Gln Leu Ala Glu Arg Leu Gly Ala Pro

```
            225                 230                 235                 240
Val Ala Thr Gly Tyr Leu Arg Asn Asp Ala Phe Pro Ala Lys His Pro
                245                 250                 255

Leu Trp Ala Gly Pro Leu Gly Tyr Gln Gly Ser Lys Ala Ala Met Lys
                260                 265                 270

Leu Ile Ala Gln Ala Asp Val Ile Ala Leu Gly Ser Arg Met Gly
                275                 280                 285

Pro Phe Gly Thr Leu Pro Gln His Gly Met Asp Tyr Trp Pro Lys Ala
                290                 295                 300

Ala Lys Ile Ile Gln Ile Glu Ala Asp His Thr Asn Leu Gly Leu Val
305                 310                 315                 320

Lys Lys Ile Ala Val Gly Ile Asn Gly Asp Ala Lys Ala Val Ala Ala
                325                 330                 335

Glu Leu Ser Arg Arg Leu Ala Asp Val Thr Leu Gly Cys Asp Ala Thr
                340                 345                 350

Lys Ala Ala Arg Ala Asp Thr Ile Ala Thr Glu Lys Ala Ala Trp Glu
                355                 360                 365

Lys Glu Leu Asp Gly Trp Thr His Glu Arg Asp Pro Tyr Ser Leu Asp
                370                 375                 380

Met Ile Glu Glu Ala Lys Gly Glu Arg Thr Pro Thr Gly Gly Ser Tyr
385                 390                 395                 400

Leu His Pro Arg Gln Val Leu Arg Glu Leu Lys Ala Met Pro Ala
                405                 410                 415

Arg Val Met Val Ser Thr Asp Ile Gly Asn Ile Asn Ser Val Ala Asn
                420                 425                 430

Ser Tyr Leu Arg Phe Asp Glu Pro Arg Ser Phe Phe Ala Pro Met Ser
                435                 440                 445

Phe Gly Asn Cys Gly Tyr Ala Leu Pro Thr Ile Ile Gly Ala Lys Cys
                450                 455                 460

Ala Ala Pro Asp Arg Pro Ala Ile Ala Tyr Ala Gly Asp Gly Ala Trp
465                 470                 475                 480

Gly Met Ser Met Met Glu Ile Met Thr Ala Val Arg His Asp Ile Pro
                485                 490                 495

Val Thr Ala Val Val Phe His Asn Arg Gln Trp Gly Ala Glu Lys Lys
                500                 505                 510

Asn Gln Val Asp Phe Tyr Asn Arg Arg Phe Val Ala Gly Glu Leu Glu
                515                 520                 525

Ser Glu Ser Phe Ser Asp Ile Ala Lys Ala Met Gly Ala Glu Gly Ile
                530                 535                 540

Val Val Asp His Ile Glu Asp Val Gly Pro Ala Leu Gln Lys Ala Ile
545                 550                 555                 560

Asp Met Gln Met Lys Glu Gly Lys Thr Cys Val Ile Glu Ile Met Cys
                565                 570                 575

Thr Arg Glu Leu Gly Asp Pro Phe Arg Arg Asp Ala Leu Ser Lys Pro
                580                 585                 590

Val Arg Met Leu Asp Lys Tyr Lys Asp Tyr Val
                595                 600

<210> SEQ ID NO 23
<211> LENGTH: 584
<212> TYPE: PRT
<213> ORGANISM: Desulfonispora thiosulfatigenes

<400> SEQUENCE: 23
```

```
Met Ala Lys Val Lys Met Thr Pro Ser Glu Ala Met Thr Glu Val Leu
1               5                   10                  15

Val Asn Glu Gly Val Thr His Val Thr Gly Ile Leu Gly Ser Ala Phe
            20                  25                  30

Met Asp Met Leu Asp Leu Trp Pro Thr Ala Gly Ile Glu Phe Ile Ala
        35                  40                  45

Val Arg His Glu Gln Thr Ala Gly His Met Gln Asp Ala Tyr Cys Arg
    50                  55                  60

Ile Thr Gly Lys Ala Ser Val Cys Ile Gly Gln Asn Gly Pro Gly Val
65                  70                  75                  80

Thr Asn Leu Val Thr Cys Val Ala Ala Asn Gln Ala His Thr Pro
                85                  90                  95

Met Val Val Leu Gly Pro Ser Ala Gly Thr Pro Thr Val Gly Trp Asp
            100                 105                 110

Gly Phe Gln Glu Cys Asp Gln Val Ser Ile Phe Arg Ser Ile Thr Lys
            115                 120                 125

Gln Val Leu Gln Val Pro His Pro Ser Arg Ala Gly Asp Val Leu Arg
            130                 135                 140

Thr Ala Phe Arg Ile Ala Tyr Ala Glu Arg Gly Pro Val Tyr Val Asp
145                 150                 155                 160

Ile Pro Arg Asn Tyr Phe Tyr Gly Glu Val Tyr Glu Ile Leu Arg
                165                 170                 175

Pro Asp Gln Tyr Arg Ala Met Asn Val Arg Gly Ala Gly Asp Ala Thr
            180                 185                 190

Glu Leu Ala Arg Ala Thr Glu Ile Leu Ala Ala Lys Asn Pro Val
            195                 200                 205

Ile Ile Ser Gly Arg Gly Val Val Asp Ala Asp Ala Phe Ala Glu Val
210                 215                 220

Lys Glu Ile Ala His Met Leu Thr Ala Pro Val Ala Met Ser Tyr Leu
225                 230                 235                 240

His Asn Asp Thr Tyr Pro Ala Asp Asp Glu Leu Trp Val Gly Pro Ile
                245                 250                 255

Gly Tyr Met Gly Ala Lys Ser Ala Met Tyr Ser Leu Gln Asp Ala Asp
            260                 265                 270

Val Ile Leu Ala Ile Gly Ser Arg Leu Ser Val Phe Gly Thr Leu Pro
275                 280                 285

Gln Tyr Asp Ile Asn Tyr Phe Pro Glu Asn Ala Lys Ile Ile Gln Ile
            290                 295                 300

Glu Val Asn Pro Lys Gln Ile Gly Arg Arg His Pro Val Thr Val Pro
305                 310                 315                 320

Ile Ile Gly Asp Ala Lys Leu Ala Thr Ala Glu Leu Ile Lys Leu Leu
                325                 330                 335

Lys Ala Lys Gly Asp Val Lys Pro Asn Ala Glu Arg Leu Ala Lys Ile
            340                 345                 350

Gln Glu Arg Arg Asn Asp Trp Phe Lys Glu Ile Glu Glu Met Ala Met
            355                 360                 365

Met Pro Gly Asn Pro Ile Asn Pro Arg Arg Val Leu Phe Glu Val Ala
            370                 375                 380

Lys Leu Met Pro Glu Asp Ala Ile Leu Thr Thr Asp Ile Gly Asn Val
385                 390                 395                 400

Ala Ser Thr Ala Asn Ser Tyr Phe Lys Phe Thr Lys Pro Lys Lys His
                405                 410                 415

Ile Ala Ala Leu Thr Phe Gly Asn Thr Gly Phe Ala Tyr Gln Ala Gly
```

```
                    420             425             430
Leu Gly Ala Gln Met Ala Glu Pro Asp Ser Pro Val Val Ala Ile Val
            435                 440                 445

Gly Asp Gly Ala Trp Gly Gln Ser Leu His Glu Ile Ser Thr Ala Val
            450                 455                 460

Gln Tyr Lys Leu Pro Val Ile Ala Cys Val Phe Arg Asn Met Ala Trp
465                 470                 475                 480

Cys Ala Glu Lys Lys Asn Gln Ile Asp Phe Tyr Asn Asn Arg Phe Val
                485                 490                 495

Gly Thr Glu Ile Pro Asn Pro Ile Ser Phe Ile Pro Ala Ala Glu Ala
            500                 505                 510

Phe Gly Ala Lys Gly Ile Arg Val Glu Lys Pro Glu Asp Ile Ala Asp
            515                 520                 525

Ala Phe Lys Gln Gly Leu Ala Trp Arg Ala Glu Gly His Pro Val Val
            530                 535                 540

Leu Glu Phe Val Val Asp Gly Thr Ile Leu Ala Pro Pro Phe Arg Lys
545                 550                 555                 560

Asp Ala Leu Ala Leu Pro Thr Arg Tyr Leu Pro Lys Tyr Glu His Leu
                565                 570                 575

Asp Ala Lys Tyr Phe Pro Lys Asn
            580

<210> SEQ ID NO 24
<211> LENGTH: 591
<212> TYPE: PRT
<213> ORGANISM: Rhizobium meliloti
<220> FEATURE:
<223> OTHER INFORMATION: strain 1021

<400> SEQUENCE: 24

Met Lys Met Thr Thr Glu Glu Ala Phe Val Lys Val Leu Gln Met His
1               5                   10                  15

Gly Ile Glu His Ala Phe Gly Ile Ile Gly Ser Ala Met Met Pro Val
            20                  25                  30

Ser Asp Leu Phe Pro Lys Ala Gly Ile Arg Phe Trp Asp Cys Ala His
            35                  40                  45

Glu Thr Asn Ala Gly Met Met Ala Asp Gly Phe Ser Arg Ala Thr Gly
        50                  55                  60

Thr Met Ser Met Ala Ile Gly Gln Asn Gly Pro Gly Val Thr Gly Phe
65                  70                  75                  80

Ile Thr Ala Met Lys Thr Ala Tyr Trp Asn His Thr Pro Leu Leu Met
                85                  90                  95

Val Thr Pro Gln Ala Ala Asn Lys Thr Ile Gly Gln Gly Gly Phe Gln
                100                 105                 110

Glu Val Asp Gln Met Ala Met Phe Glu Glu Met Val Cys Tyr Gln Glu
            115                 120                 125

Glu Val Arg Asp Pro Ser Arg Ile Pro Glu Val Leu Asn Arg Val Ile
            130                 135                 140

Glu Lys Ala Trp Arg Gly Cys Ala Pro Ala Gln Ile Asn Ile Pro Arg
145                 150                 155                 160

Asp Phe Trp Thr Gln Val Ile Asp Val Asp Leu Pro Arg Ile Val Arg
                165                 170                 175

Phe Glu Arg Pro Ala Gly Gly Pro Ala Ala Ile Ala Gln Ala Ala Arg
            180                 185                 190

Leu Leu Ser Glu Ala Lys Phe Pro Val Ile Leu Asn Gly Ala Gly Val
```

```
                195                 200                 205
Val Ile Gly Asn Ala Ile Gln Glu Ser Met Ala Leu Ala Glu Lys Leu
210                 215                 220

Asp Ala Pro Val Cys Cys Gly Tyr Gln His Asn Asp Ala Phe Pro Gly
225                 230                 235                 240

Ser His Arg Leu Ser Val Gly Pro Leu Gly Tyr Asn Gly Ser Lys Ala
                245                 250                 255

Ala Met Glu Leu Ile Ser Lys Ala Asp Val Val Leu Ala Leu Gly Thr
                260                 265                 270

Arg Leu Asn Pro Phe Ser Thr Leu Pro Gly Tyr Gly Ile Asp Tyr Trp
                275                 280                 285

Pro Lys Asp Ala Ala Ile Ile Gln Val Asp Ile Asn Ala Asp Arg Ile
290                 295                 300

Gly Leu Thr Lys Lys Val Thr Val Gly Ile Cys Gly Asp Ala Lys Gln
305                 310                 315                 320

Val Ala Gln Gln Ile Leu Gln Leu Ala Pro Ala Ala Gly Asp Ala
                325                 330                 335

Ser Arg Glu Glu Arg Lys Ala Leu Val His Gln Thr Arg Ser Ala Trp
                340                 345                 350

Leu Gln Gln Leu Ser Ser Met Asp His Glu Asp Asp Pro Gly Thr
                355                 360                 365

Glu Trp Asn Val Gly Ala Arg Gln Arg Glu Pro Asp Arg Met Ser Pro
370                 375                 380

Arg Gln Val Trp Arg Ala Ile Gln Ala Val Leu Pro Lys Glu Ala Ile
385                 390                 395                 400

Ile Ser Thr Asp Ile Gly Asn Asn Cys Ala Ile Gly Asn Ala Tyr Pro
                405                 410                 415

Ser Phe Glu Gln Gly Arg Lys Tyr Leu Ala Pro Gly Met Phe Gly Pro
                420                 425                 430

Cys Gly Tyr Gly Phe Pro Ser Ile Val Gly Ala Lys Ile Gly Cys Pro
                435                 440                 445

Asp Val Pro Val Val Gly Phe Ala Gly Asp Gly Ala Phe Gly Ile Ser
450                 455                 460

Met Asn Glu Met Thr Ser Ile Gly Arg Glu Gly Trp Pro Ala Ile Thr
465                 470                 475                 480

Met Val Ile Phe Arg Asn Tyr Gln Trp Gly Ala Glu Lys Arg Asn Thr
                485                 490                 495

Thr Leu Trp Tyr Asp Asn Asn Phe Val Gly Thr Glu Leu Asn Pro Asn
                500                 505                 510

Leu Ser Tyr Ala Lys Val Ala Asp Gly Cys Gly Leu Lys Gly Val Thr
                515                 520                 525

Val Asp Thr Pro Ala Ala Leu Thr Glu Ala Leu Ala Lys Ala Ile Glu
                530                 535                 540

Asp Gln Ala Lys Gly Ile Thr Thr Phe Val Glu Val Leu Asn Gln
545                 550                 555                 560

Glu Leu Gly Glu Pro Phe Arg Arg Asp Ala Met Lys Lys Pro Val Ala
                565                 570                 575

Val Ala Gly Ile Asp Arg Ala Asp Met Arg Thr Gln Arg Arg Met
                580                 585                 590

<210> SEQ ID NO 25
<211> LENGTH: 603
<212> TYPE: PRT
<213> ORGANISM: Roseovarius nubinhibens
```

<400> SEQUENCE: 25

Met Leu Phe Arg Ala Ser Gln Pro Glu Asp Lys Pro Met Lys Met Thr
1               5                   10                  15

Thr Glu Glu Ala Phe Val Lys Thr Leu Gln Met His Gly Ile Gln His
            20                  25                  30

Ala Phe Gly Ile Ile Gly Ser Ala Met Met Pro Ile Ser Asp Ile Phe
        35                  40                  45

Gly Lys Ala Gly Ile Thr Phe Trp Asp Cys Ala His Glu Gly Ser Gly
    50                  55                  60

Gly Met Met Ala Asp Gly Tyr Thr Arg Ala Thr Gly Lys Met Ser Met
65                  70                  75                  80

Met Ile Ala Gln Asn Gly Pro Gly Ile Thr Asn Phe Val Thr Ala Val
                85                  90                  95

Lys Thr Ala Tyr Trp Asn His Thr Pro Leu Leu Val Thr Pro Gln
            100                 105                 110

Ala Ala Asn Lys Thr Met Gly Gln Gly Phe Gln Glu Val Glu Gln
        115                 120                 125

Met Ala Ala Phe Lys Asp Met Val Cys Tyr Gln Glu Glu Val Arg Asp
130                 135                 140

Pro Thr Arg Met Ala Glu Val Leu Asn Arg Val Ile Leu Asn Ala Lys
145                 150                 155                 160

Arg Tyr Ser Ala Pro Ala Gln Ile Asn Val Pro Arg Asp Tyr Phe Thr
                165                 170                 175

Gln Val Ile Asp Ile Glu Leu Pro Lys Ile Val Asp Phe Glu Arg Pro
            180                 185                 190

Ser Gly Gly Glu Glu Ala Leu Asp Glu Ala Ala Lys Leu Leu Ser Glu
        195                 200                 205

Ala Lys Phe Pro Val Ile Leu Asn Gly Ala Gly Val Ile Leu Ala Gly
210                 215                 220

Ala Ile Pro Ala Thr Ala Glu Leu Ala Glu Arg Leu Asp Ala Pro Val
225                 230                 235                 240

Cys Cys Gly Tyr Gln His Asn Asp Ala Phe Pro Gly Ser His Pro Leu
                245                 250                 255

His Ala Gly Pro Leu Gly Tyr Asn Gly Ser Lys Ala Gly Met Glu Leu
            260                 265                 270

Ile Ser Lys Ala Asp Val Val Leu Ala Leu Gly Thr Arg Leu Asn Pro
        275                 280                 285

Phe Ser Thr Leu Pro Gly Tyr Gly Ile Asp Tyr Trp Pro Lys Asp Ala
    290                 295                 300

Lys Ile Ile Gln Val Asp Val Lys Pro Glu Arg Ile Gly Leu Thr Lys
305                 310                 315                 320

Pro Val Ala Val Gly Ile Val Gly Asp Ala Lys Lys Val Ala Lys Thr
                325                 330                 335

Ile Leu Ala Lys Leu Ser Asp Thr Ala Gly Asp Ala Arg Glu Glu
            340                 345                 350

Arg Lys Ala Thr Ile Ala Lys Thr Lys Ser Ala Trp Ala Gln Glu Leu
        355                 360                 365

Ser Ser Met Asp His Glu Gln Asp Asp Pro Gly Thr Thr Trp Asn Glu
    370                 375                 380

Arg Ala Arg Gly Ala Lys Pro Asp Trp Met Ser Pro Arg Met Ala Trp
385                 390                 395                 400

Arg Ala Ile Gln Ala Ala Leu Pro Lys Glu Ala Ile Ile Ser Ser Asp

```
                405                 410                 415
Ile Gly Asn Asn Cys Ala Ile Gly Asn Ala Tyr Pro Ser Phe Glu Glu
            420                 425                 430

Gly Arg Lys Tyr Leu Ala Pro Gly Leu Phe Gly Pro Cys Gly Tyr Gly
            435                 440                 445

Leu Pro Ala Val Val Gly Ala Lys Ile Gly Cys Pro Asp Thr Pro Val
450                 455                 460

Val Gly Phe Ser Gly Asp Gly Ala Phe Gly Ile Ala Val Asn Glu Leu
465                 470                 475                 480

Thr Ala Ile Gly Arg Gly Glu Trp Pro Ala Val Thr His Val Phe
                485                 490                 495

Arg Asn Tyr Gln Trp Gly Ala Glu Lys Arg Asn Ser Thr Leu Trp Phe
            500                 505                 510

Asp Asp Asn Phe Val Gly Thr Glu Leu Asp Gln Val Ser Tyr Ala
            515                 520                 525

Gly Ile Ala Lys Ala Cys Gly Leu Lys Gly Val Val Ala Arg Thr Met
            530                 535                 540

Asp Glu Leu Thr Asp Ala Leu Asp Gln Ala Ile Lys Asp Gln Lys Ala
545                 550                 555                 560

Gly Thr Thr Thr Leu Ile Glu Ala Met Ile Asn Gln Glu Leu Gly Glu
                565                 570                 575

Pro Phe Arg Arg Asp Ala Met Lys Lys Pro Val Ala Val Ala Gly Ile
            580                 585                 590

Asp Pro Ala Asp Met Arg Glu Gln Gln Val Asp
            595                 600

<210> SEQ ID NO 26
<211> LENGTH: 364
<212> TYPE: PRT
<213> ORGANISM: Oryctolagus cuniculus
<220> FEATURE:
<223> OTHER INFORMATION: Fructose-bisphosphate aldolase A Oryctolagus
      cuniculus

<400> SEQUENCE: 26

Met Pro His Ser His Pro Ala Leu Thr Pro Glu Gln Lys Lys Glu Leu
1               5                   10                  15

Ser Asp Ile Ala His Arg Ile Val Ala Pro Gly Lys Gly Ile Leu Ala
            20                  25                  30

Ala Asp Glu Ser Thr Gly Ser Ile Ala Lys Arg Leu Gln Ser Ile Gly
        35                  40                  45

Thr Glu Asn Thr Glu Glu Asn Arg Arg Phe Tyr Arg Gln Leu Leu Leu
    50                  55                  60

Thr Ala Asp Asp Arg Val Asn Pro Cys Ile Gly Gly Val Ile Leu Phe
65                  70                  75                  80

His Glu Thr Leu Tyr Gln Lys Ala Asp Asp Gly Arg Pro Phe Pro Gln
                85                  90                  95

Val Ile Lys Ser Lys Gly Gly Val Val Gly Ile Lys Val Asp Lys Gly
            100                 105                 110

Val Val Pro Leu Ala Gly Thr Asn Gly Glu Thr Thr Thr Gln Gly Leu
        115                 120                 125

Asp Gly Leu Ser Glu Arg Cys Ala Gln Tyr Lys Lys Asp Gly Ala Asp
    130                 135                 140

Phe Ala Lys Trp Arg Cys Val Leu Lys Ile Gly Glu His Thr Pro Ser
145                 150                 155                 160
```

```
Ala Leu Ala Ile Met Glu Asn Ala Asn Val Leu Ala Arg Tyr Ala Ser
            165                 170                 175

Ile Cys Gln Gln Asn Gly Ile Val Pro Ile Val Glu Pro Glu Ile Leu
        180                 185                 190

Pro Asp Gly Asp His Asp Leu Lys Arg Cys Gln Tyr Val Thr Glu Lys
        195                 200                 205

Val Leu Ala Ala Val Tyr Lys Ala Leu Ser Asp His His Ile Tyr Leu
    210                 215                 220

Glu Gly Thr Leu Leu Lys Pro Asn Met Val Thr Pro Gly His Ala Cys
225                 230                 235                 240

Thr Gln Lys Tyr Ser His Glu Glu Ile Ala Met Ala Thr Val Thr Ala
                245                 250                 255

Leu Arg Arg Thr Val Pro Pro Ala Val Thr Gly Val Thr Phe Leu Ser
                260                 265                 270

Gly Gly Gln Ser Glu Glu Glu Ala Ser Ile Asn Leu Asn Ala Ile Asn
                275                 280                 285

Lys Cys Pro Leu Leu Lys Pro Trp Ala Leu Thr Phe Ser Tyr Gly Arg
            290                 295                 300

Ala Leu Gln Ala Ser Ala Leu Lys Ala Trp Gly Gly Lys Lys Glu Asn
305                 310                 315                 320

Leu Lys Ala Ala Gln Glu Glu Tyr Val Lys Arg Ala Leu Ala Asn Ser
                325                 330                 335

Leu Ala Cys Gln Gly Lys Tyr Thr Pro Ser Gly Gln Ala Gly Ala Ala
                340                 345                 350

Ala Ser Glu Ser Leu Phe Ile Ser Asn His Ala Tyr
                355                 360

<210> SEQ ID NO 27
<211> LENGTH: 359
<212> TYPE: PRT
<213> ORGANISM: Escherichia coli
<220> FEATURE:
<223> OTHER INFORMATION: Fructose-bisphosphate aldolase class 2
      Escherichia coli (strain K12)

<400> SEQUENCE: 27

Met Ser Lys Ile Phe Asp Phe Val Lys Pro Gly Val Ile Thr Gly Asp
1               5                   10                  15

Asp Val Gln Lys Val Phe Gln Val Ala Lys Glu Asn Asn Phe Ala Leu
            20                  25                  30

Pro Ala Val Asn Cys Val Gly Thr Asp Ser Ile Asn Ala Val Leu Glu
        35                  40                  45

Thr Ala Ala Lys Val Lys Ala Pro Val Ile Val Gln Phe Ser Asn Gly
    50                  55                  60

Gly Ala Ser Phe Ile Ala Gly Lys Gly Val Lys Ser Asp Val Pro Gln
65                  70                  75                  80

Gly Ala Ala Ile Leu Gly Ala Ile Ser Gly Ala His His Val His Gln
                85                  90                  95

Met Ala Glu His Tyr Gly Val Pro Val Ile Leu His Thr Asp His Cys
            100                 105                 110

Ala Lys Lys Leu Leu Pro Trp Ile Asp Gly Leu Leu Asp Ala Gly Glu
        115                 120                 125

Lys His Phe Ala Ala Thr Gly Lys Pro Leu Phe Ser Ser His Met Ile
    130                 135                 140

Asp Leu Ser Glu Glu Ser Leu Gln Glu Asn Ile Glu Ile Cys Ser Lys
145                 150                 155                 160
```

```
Tyr Leu Glu Arg Met Ser Lys Ile Gly Met Thr Leu Glu Ile Glu Leu
            165                 170                 175

Gly Cys Thr Gly Gly Glu Asp Gly Val Asp Asn Ser His Met Asp
        180                 185                 190

Ala Ser Ala Leu Tyr Thr Gln Pro Glu Asp Val Asp Tyr Ala Tyr Thr
        195                 200                 205

Glu Leu Ser Lys Ile Ser Pro Arg Phe Thr Ile Ala Ala Ser Phe Gly
        210                 215                 220

Asn Val His Gly Val Tyr Lys Pro Gly Asn Val Val Leu Thr Pro Thr
225                 230                 235                 240

Ile Leu Arg Asp Ser Gln Glu Tyr Val Ser Lys Lys His Asn Leu Pro
                245                 250                 255

His Asn Ser Leu Asn Phe Val Phe His Gly Gly Ser Gly Ser Thr Ala
            260                 265                 270

Gln Glu Ile Lys Asp Ser Val Ser Tyr Gly Val Val Lys Met Asn Ile
        275                 280                 285

Asp Thr Asp Thr Gln Trp Ala Thr Trp Glu Gly Val Leu Asn Tyr Tyr
        290                 295                 300

Lys Ala Asn Glu Ala Tyr Leu Gln Gly Gln Leu Gly Asn Pro Lys Gly
305                 310                 315                 320

Glu Asp Gln Pro Asn Lys Lys Tyr Tyr Asp Pro Arg Val Trp Leu Arg
                325                 330                 335

Ala Gly Gln Thr Ser Met Ile Ala Arg Leu Glu Lys Ala Phe Gln Glu
            340                 345                 350

Leu Asn Ala Ile Asp Val Leu
        355

<210> SEQ ID NO 28
<211> LENGTH: 359
<212> TYPE: PRT
<213> ORGANISM: Saccharomyces cerevisiae
<220> FEATURE:
<223> OTHER INFORMATION: Fructose-bisphosphate aldolase Saccharomyces
      cerevisiae (strain ATCC 204508 / S288c)

<400> SEQUENCE: 28

Met Gly Val Glu Gln Ile Leu Lys Arg Lys Thr Gly Val Ile Val Gly
1               5                   10                  15

Glu Asp Val His Asn Leu Phe Thr Tyr Ala Lys Glu His Lys Phe Ala
            20                  25                  30

Ile Pro Ala Ile Asn Val Thr Ser Ser Thr Ala Val Ala Ala Leu
        35                  40                  45

Glu Ala Ala Arg Asp Ser Lys Ser Pro Ile Ile Leu Gln Thr Ser Asn
    50                  55                  60

Gly Gly Ala Ala Tyr Phe Ala Gly Lys Gly Ile Ser Asn Glu Gly Gln
65                  70                  75                  80

Asn Ala Ser Ile Lys Gly Ala Ile Ala Ala His Tyr Ile Arg Ser
            85                  90                  95

Ile Ala Pro Ala Tyr Gly Ile Pro Val Val Leu His Ser Asp His Cys
        100                 105                 110

Ala Lys Lys Leu Leu Pro Trp Phe Asp Gly Met Leu Glu Ala Asp Glu
        115                 120                 125

Ala Tyr Phe Lys Glu His Gly Glu Pro Leu Phe Ser Ser His Met Leu
        130                 135                 140

Asp Leu Ser Glu Glu Thr Asp Glu Glu Asn Ile Ser Thr Cys Val Lys
```

```
                145                 150                 155                 160
Tyr Phe Lys Arg Met Ala Ala Met Asp Gln Trp Leu Glu Met Glu Ile
                    165                 170                 175
Gly Ile Thr Gly Gly Glu Glu Asp Gly Val Asn Asn Glu Asn Ala Asp
                    180                 185                 190
Lys Glu Asp Leu Tyr Thr Lys Pro Glu Gln Val Tyr Asn Val Tyr Lys
                    195                 200                 205
Ala Leu His Pro Ile Ser Pro Asn Phe Ser Ile Ala Ala Ala Phe Gly
                    210                 215                 220
Asn Cys His Gly Leu Tyr Ala Gly Asp Ile Ala Leu Arg Pro Glu Ile
225                 230                 235                 240
Leu Ala Glu His Gln Lys Tyr Thr Arg Glu Gln Val Gly Cys Lys Glu
                    245                 250                 255
Glu Lys Pro Leu Phe Leu Val Phe His Gly Gly Ser Gly Ser Thr Val
                    260                 265                 270
Gln Glu Phe His Thr Gly Ile Asp Asn Gly Val Val Lys Val Asn Leu
                    275                 280                 285
Asp Thr Asp Cys Gln Tyr Ala Tyr Leu Thr Gly Ile Arg Asp Tyr Val
                    290                 295                 300
Leu Asn Lys Lys Asp Tyr Ile Met Ser Pro Val Gly Asn Pro Glu Gly
305                 310                 315                 320
Pro Glu Lys Pro Asn Lys Phe Phe Asp Pro Arg Val Trp Val Arg
                    325                 330                 335
Glu Gly Glu Lys Thr Met Gly Ala Lys Ile Thr Lys Ser Leu Glu Thr
                    340                 345                 350
Phe Arg Thr Thr Asn Thr Leu
                    355

<210> SEQ ID NO 29
<211> LENGTH: 305
<212> TYPE: PRT
<213> ORGANISM: Thermus aquaticus
<220> FEATURE:
<223> OTHER INFORMATION: Fructose-1,6-bisphosphate aldolase Thermus
      aquaticus

<400> SEQUENCE: 29

Met Leu Val Thr Gly Leu Glu Ile Leu Lys Lys Ala Arg Glu Gly
1               5                   10                  15

Tyr Gly Val Gly Ala Phe Asn Val Asn Asn Met Glu Phe Leu Gln Ala
                    20                  25                  30

Val Leu Glu Ala Ala Glu Glu Gln Arg Ser Pro Val Ile Leu Ala Leu
                35                  40                  45

Ser Glu Gly Ala Met Lys Tyr Gly Gly Arg Ala Leu Thr Leu Met Ala
            50                  55                  60

Val Glu Leu Ala Lys Glu Ala Arg Val Pro Val Ala Val His Leu Asp
65                  70                  75                  80

His Gly Ser Ser Tyr Glu Ser Val Leu Arg Ala Leu Arg Ala Gly Phe
                    85                  90                  95

Thr Ser Val Met Ile Asp Lys Ser His Glu Asp Phe Glu Thr Asn Val
                    100                 105                 110

Arg Glu Thr Arg Arg Val Val Glu Ala Ala His Ala Val Gly Val Thr
                115                 120                 125

Val Glu Ala Glu Leu Gly Arg Leu Ala Gly Ile Glu Glu His Val Ala
            130                 135                 140
```

```
Val Asp Glu Lys Asp Ala Leu Leu Thr Asn Pro Glu Glu Ala Arg Ile
145                 150                 155                 160

Phe Met Glu Arg Thr Gly Ala Asp Tyr Leu Ala Val Ala Ile Gly Thr
                165                 170                 175

Ser His Gly Ala Tyr Lys Gly Lys Gly Arg Pro Phe Ile Asp His Ala
            180                 185                 190

Arg Leu Glu Arg Ile Ala Arg Leu Val Pro Ala Pro Leu Val Leu His
        195                 200                 205

Gly Ala Ser Ala Val Pro Pro Glu Leu Val Glu Arg Phe Arg Ala Ser
    210                 215                 220

Gly Gly Glu Ile Gly Glu Ala Ala Gly Ile His Pro Glu Asp Ile Lys
225                 230                 235                 240

Lys Ala Ile Ser Leu Gly Ile Ala Lys Ile Asn Thr Asp Thr Asp Leu
                245                 250                 255

Arg Leu Ala Phe Thr Ala Leu Ile Arg Glu Ala Leu Asn Lys Asn Pro
                260                 265                 270

Lys Glu Phe Asp Pro Arg Lys Tyr Leu Gly Pro Ala Arg Glu Ala Val
            275                 280                 285

Lys Glu Val Val Lys Ser Arg Met Glu Leu Phe Gly Ser Val Gly Arg
    290                 295                 300

Ala
305

<210> SEQ ID NO 30
<211> LENGTH: 344
<212> TYPE: PRT
<213> ORGANISM: Mycobacterium tuberculosis
<220> FEATURE:
<223> OTHER INFORMATION: Fructose-bisphosphate aldolase Mycobacterium
      tuberculosis

<400> SEQUENCE: 30

Met Pro Ile Ala Thr Pro Glu Val Tyr Ala Glu Met Leu Gly Gln Ala
1               5                   10                  15

Lys Gln Asn Ser Tyr Ala Phe Pro Ala Ile Asn Cys Thr Ser Ser Glu
            20                  25                  30

Thr Val Asn Ala Ala Ile Lys Gly Phe Ala Asp Ala Gly Ser Asp Gly
        35                  40                  45

Ile Ile Gln Phe Ser Thr Gly Gly Ala Glu Phe Gly Ser Gly Leu Gly
    50                  55                  60

Val Lys Asp Met Val Thr Gly Ala Val Ala Leu Ala Glu Phe Thr His
65                  70                  75                  80

Val Ile Ala Ala Lys Tyr Pro Val Asn Val Ala Leu His Thr Asp His
                85                  90                  95

Cys Pro Lys Asp Lys Leu Asp Ser Tyr Val Arg Pro Leu Leu Ala Ile
            100                 105                 110

Ser Ala Gln Arg Val Ser Lys Gly Gly Asn Pro Leu Phe Gln Ser His
        115                 120                 125

Met Trp Asp Gly Ser Ala Val Pro Ile Asp Glu Asn Leu Ala Ile Ala
    130                 135                 140

Gln Glu Leu Leu Lys Ala Ala Ala Ala Lys Ile Ile Leu Glu Ile
145                 150                 155                 160

Glu Ile Gly Val Val Gly Gly Glu Glu Asp Gly Val Ala Asn Glu Ile
                165                 170                 175

Asn Glu Lys Leu Tyr Thr Ser Pro Glu Asp Phe Glu Lys Thr Ile Glu
            180                 185                 190
```

```
Ala Leu Gly Ala Gly Glu His Gly Lys Tyr Leu Leu Ala Ala Thr Phe
            195                 200                 205

Gly Asn Val His Gly Val Tyr Lys Pro Gly Asn Val Lys Leu Arg Pro
        210                 215                 220

Asp Ile Leu Ala Gln Gly Gln Val Ala Ala Lys Leu Gly Leu
225                 230                 235                 240

Pro Ala Asp Ala Lys Pro Phe Asp Phe Val Phe His Gly Gly Ser Gly
                245                 250                 255

Ser Leu Lys Ser Glu Ile Glu Glu Ala Leu Arg Tyr Gly Val Val Lys
                260                 265                 270

Met Asn Val Asp Thr Asp Thr Gln Tyr Ala Phe Thr Arg Pro Ile Ala
            275                 280                 285

Gly His Met Phe Thr Asn Tyr Asp Gly Val Leu Lys Val Asp Gly Glu
        290                 295                 300

Val Gly Val Lys Lys Val Tyr Asp Pro Arg Ser Tyr Leu Lys Lys Ala
305                 310                 315                 320

Glu Ala Ser Met Ser Gln Arg Val Val Gln Ala Cys Asn Asp Leu His
                325                 330                 335

Cys Ala Gly Lys Ser Leu Thr His
            340

<210> SEQ ID NO 31
<211> LENGTH: 354
<212> TYPE: PRT
<213> ORGANISM: Methylococcus capsulatus
<220> FEATURE:
<223> OTHER INFORMATION: Fructose-bisphosphate aldolase, class II
      OS=Methylococcus capsulatus (strain ATCC 33009 / NCIMB 11132 /
      Bath) GN=fbaA-2 PE=4 SV=1

<400> SEQUENCE: 31

Met Ala Leu Ile Ser Leu Arg Gln Leu Leu Asp His Ala Ala Glu His
1               5                   10                  15

Gly Tyr Gly Leu Pro Ala Phe Asn Val Asn Asn Met Glu Gln Ile Lys
            20                  25                  30

Ala Ile Met Glu Ala Ala Ser Ala Val Asp Ala Pro Val Ile Leu Gln
        35                  40                  45

Gly Ser Ala Gly Ala Arg Thr Tyr Ala Gly Glu Pro Phe Leu Arg His
    50                  55                  60

Leu Val Arg Ala Ala Ile Glu Met Tyr Pro His Ile Pro Val Cys Met
65                  70                  75                  80

His Gln Asp His Gly Ala Ser Pro Ala Val Cys Ile Arg Ser Ile Gln
                85                  90                  95

Ser Gly Phe Ser Ser Val Met Met Asp Gly Ser Leu Leu Glu Asp Met
            100                 105                 110

Lys Thr Pro Ala Ser Tyr Ala Tyr Asn Val Glu Thr Thr Arg Lys Val
        115                 120                 125

Val Glu Met Ala His Ala Cys Gly Val Ser Val Glu Gly Glu Leu Gly
    130                 135                 140

Cys Leu Gly Ser Leu Glu Thr Gly Arg Ala Gly Lys Glu Asp Gly His
145                 150                 155                 160

Gly Ala Glu Gly Glu Leu Asp His Ser Leu Leu Leu Thr Asp Pro Asp
                165                 170                 175

Glu Ala Ala Asp Phe Val Arg Gln Thr Gln Val Asp Ala Leu Ala Ile
            180                 185                 190
```

```
Ala Ile Gly Thr Ser His Gly Ala Tyr Lys Phe Thr Arg Lys Pro Thr
            195                 200                 205

Gly Gln Val Leu Arg Ile Asp Arg Val Lys Ala Ile His Gln Arg Ile
        210                 215                 220

Pro Thr Ile His Leu Val Met His Gly Ser Ser Val Pro Glu Glu
225                 230                 235                 240

Trp Ala Gln Met Ile Asn Asp Tyr Gly Gly Asp Ile Gly Gln Thr Tyr
                245                 250                 255

Gly Val Pro Val Glu Glu Ile Val Gly Ile Arg His Gly Val Arg
            260                 265                 270

Lys Val Asn Ile Asp Thr Asp Leu Arg Ile Ala Ser Tyr Gly Ala Met
            275                 280                 285

Arg Arg Phe Met Val Glu Asp Arg Lys Asn Phe Asp Pro Arg Lys Leu
        290                 295                 300

Tyr Lys Ala Ala Gln Thr Ala Met Thr Ala Ile Cys Arg Ala Arg Tyr
305                 310                 315                 320

Glu Ala Phe Gly Ala Ala Gly Gln Ala Lys Ile Lys Pro Leu Arg
                325                 330                 335

Leu Glu Asp Met Ser Leu Ala Tyr Ala Gln Gly Lys Leu Asp Pro Ile
                340                 345                 350

Val Arg

<210> SEQ ID NO 32
<211> LENGTH: 239
<212> TYPE: PRT
<213> ORGANISM: Acetobacterium woodii
<220> FEATURE:
<223> OTHER INFORMATION: Deoxyribose-phosphate aldolase Acetobacterium
      woodii (strain ATCC 29683 / DSM 1030 / JCM 2381 / KCTC 1655)

<400> SEQUENCE: 32

Met Leu Val Leu Asn Gly Lys Glu Ile Asn Lys Ala Ser Leu Ala Lys
1               5                   10                  15

Met Ile Asp Gly Ser Leu Leu Asn Pro Phe Thr Thr Thr Gln Glu Ile
            20                  25                  30

Asp Glu Leu Val Lys Ile Ser Leu Asp Tyr Asn Thr Asn Ser Val Cys
        35                  40                  45

Val Asn Pro Asn Tyr Leu Glu Arg Val Val Lys Gln Leu Lys Gly Thr
    50                  55                  60

Asp Val Lys Ala Cys Val Val Ile Asp Tyr Pro Phe Gly Thr Gly Ser
65                  70                  75                  80

Ile Glu Asp Lys Val Asn Gln Ala Lys Val Ala Ile Glu His Gly Val
                85                  90                  95

Glu Ile Ile Asp Phe Val Ile Asp Tyr Gly His Leu Lys Ser Gly Asn
            100                 105                 110

Lys Asp His Leu Leu Lys Glu Ile Lys Ala Cys Val Ala Ala Ala Asn
        115                 120                 125

Gly Arg Glu Thr Arg Phe Ile Ile Glu Val Cys Tyr Leu Thr Pro Glu
    130                 135                 140

Glu Ile Val Thr Ala Cys Glu Cys Val Ile Asp Gly Gly Asp Phe
145                 150                 155                 160

Val Lys Thr Ser Thr Gly Arg Phe Gly Gly Pro Asp Met Glu Ile Ile
                165                 170                 175

Asp Leu Leu Val Lys Thr Cys Lys Gly Arg Cys Lys Leu Lys Val Ala
            180                 185                 190
```

```
Gly Thr Gly Gln Phe Trp Thr Ala Asn Ile Ala Leu Met Cys Ile Ala
        195                 200                 205

Ala Gly Val Asp Ile Ile Gly Thr Arg Ser Ala Lys Lys Ile Val Asp
    210                 215                 220

Ala Leu Glu Ile Phe Glu Arg Phe Ala Lys Gly Ile Glu Val Lys
225                 230                 235
```